United States Patent
Takada et al.

(10) Patent No.: US 11,230,521 B2
(45) Date of Patent: Jan. 25, 2022

(54) MONOAMINE COMPOUND AND ORGANIC ELECTROLUMINESCENCE DEVICE INCLUDING THE SAME

(71) Applicant: SAMSUNG DISPLAY CO., LTD., Yongin-si (KR)

(72) Inventors: Ichinori Takada, Yokohama (JP); Takuya Uno, Yokohama (JP); Xiulan Jin, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 326 days.

(21) Appl. No.: 15/921,936

(22) Filed: Mar. 15, 2018

(65) Prior Publication Data

US 2019/0039996 A1  Feb. 7, 2019

(30) Foreign Application Priority Data

Aug. 1, 2017  (KR) .......................... 10-2017-0097827

(51) Int. Cl.
  *C07C 211/54* (2006.01)
  *H01L 51/00* (2006.01)
  (Continued)

(52) U.S. Cl.
  CPC .......... *C07C 211/54* (2013.01); *C07D 307/91* (2013.01); *C07D 333/76* (2013.01);
  (Continued)

(58) Field of Classification Search
  CPC .................................................. C07C 211/54
  See application file for complete search history.

(56) References Cited

U.S. PATENT DOCUMENTS 8,293,921 B2  10/2012  Nomura et al.
8,334,061 B2  12/2012  Nomura et al.
(Continued)

FOREIGN PATENT DOCUMENTS

JP  2005320277 A  * 11/2005
JP  2009010364 A2 † 1/2009
(Continued)

OTHER PUBLICATIONS

English machine translation of Matsunami et al. JP 2009-010364A (Year: 2009).*

(Continued)

*Primary Examiner* — Peter F Godenschwager
(74) *Attorney, Agent, or Firm* — Lewis Roca Rothgerber Christie LLP

(57) ABSTRACT

An monoamine compound and an organic electroluminescence device including the monoamine compound, the monoamine compound being represented by the following Formula 1:

[Formula 1]

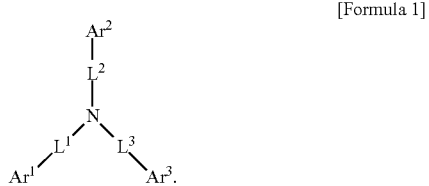

20 Claims, 1 Drawing Sheet

(51) Int. Cl.
*H01L 51/50* (2006.01)
*C09K 11/06* (2006.01)
*C07D 333/76* (2006.01)
*C07F 7/08* (2006.01)
*C07D 307/91* (2006.01)

(52) U.S. Cl.
CPC ............ *C07F 7/0805* (2013.01); *C09K 11/06* (2013.01); *H01L 51/006* (2013.01); *H01L 51/0059* (2013.01); *H01L 51/0061* (2013.01); *H01L 51/0072* (2013.01); *H01L 51/0073* (2013.01); *H01L 51/0074* (2013.01); *H01L 51/0094* (2013.01); *H01L 51/5056* (2013.01); *H01L 51/5072* (2013.01); *C07C 2603/26* (2017.05); *C09K 2211/1007* (2013.01); *C09K 2211/1011* (2013.01); *C09K 2211/1088* (2013.01); *C09K 2211/1092* (2013.01)

(56) References Cited

U.S. PATENT DOCUMENTS

| 8,343,639 | B2 | | 1/2013 | Seo et al. | |
|---|---|---|---|---|---|
| 2016/0126467 | A1 | * | 5/2016 | Fuchiwaki | H01L 51/0073 257/40 |
| 2017/0125689 | A1 | * | 5/2017 | Lee | C07D 333/76 |
| 2017/0179398 | A1 | | 6/2017 | Yokoyama et al. | |

FOREIGN PATENT DOCUMENTS

| JP | 4587703 | B2 | 11/2010 |
|---|---|---|---|
| JP | 5564305 | B2 | 7/2014 |
| JP | 5577132 | B2 | 8/2014 |
| JP | 2017-22194 | A | 1/2017 |
| JP | 2017-41647 | A | 2/2017 |
| KR | 10-1529062 | B1 | 6/2015 |
| KR | 10-2017-0028406 | A | 3/2017 |
| WO | WO 2016/006629 | A1 | 1/2016 |

OTHER PUBLICATIONS

Allen et al. "The Nitration of Terphenyls" Journal of Organic Chemistry, 1949, 14, 175-178 (Year: 1949).*

IUPAC. Compendium of Chemical Terminology, 2nd ed. (the "Gold Book"). Compiled by A. D. McNaught and A. Wilkinson. Blackwell Scientific Publications, Oxford (1997). Online version (2019-) created by S. J. Chalk. ISBN 0-9678550-9-8. https://doi.org/10.1351/goldbook. (accessed Oct. 26, 2020) (Year: 2020).*

English machine translation of Kido et al. JP-2005320277-A (Year: 2005).*

* cited by examiner
† cited by third party

MONOAMINE COMPOUND AND ORGANIC ELECTROLUMINESCENCE DEVICE INCLUDING THE SAME

CROSS-REFERENCE TO RELATED APPLICATIONS

Korean Patent Application No. 10-2017-0097827, filed on Aug. 1, 2017, and entitled: "Monoamine Compound and Organic Electroluminescence Device Including the Same," is incorporated by reference herein in its entirety.

BACKGROUND

1. Field

Embodiments relate to a monoamine compound and an organic electroluminescence device including the same.

2. Description of the Related Art

Development on an organic electroluminescence display as an image display is being actively conducted. An organic electroluminescence display is different from a liquid crystal display and is a self-luminescent display, which accomplishes display by recombining holes and electrons injected from a first electrode and a second electrode in an emission layer and emitting light from a luminescent material which includes an organic compound in the emission layer.

As an organic electroluminescence device, e.g., an organic electroluminescence device may include a first electrode, a hole transport layer disposed on the first electrode, an emission layer disposed on the hole transport layer, an electron transport layer disposed on the emission layer, and a second electrode disposed on the electron transport layer. Holes are injected from the first electrode, and the injected holes move via the hole transport layer to be injected into the emission layer. Meanwhile, electrons are injected from the second electrode, and the injected electrons move via the electron transport layer to be injected into the emission layer. By recombining the holes and electrons injected into the emission layer, excitons are generated in the emission layer. The organic electroluminescence device emits light by radiation deactivation of the excitons. In addition, various modifications to the configuration of an organic electroluminescence device may be possible.

SUMMARY

Embodiments are directed to a monoamine compound and an organic electroluminescence device including the same.

The embodiments may be realized by providing a monoamine compound represented by the following Formula 1:

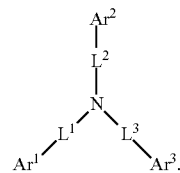

[Formula 1]

wherein, in Formula 1, $Ar^1$ is a group represented by the following Formula 2, $Ar^2$ and $Ar^3$ are each independently a group represented by the following Formula 2, a hydrogen atom, a deuterium atom, a halogen atom, a cyano group, a substituted or unsubstituted silyl group, a substituted or unsubstituted aryl group having 6 to 30 ring carbon atoms, or a substituted or unsubstituted heteroaryl group having 2 to 30 ring carbon atoms, $L^1$ to $L^3$ are each independently a direct linkage, a substituted or unsubstituted arylene group having 6 to 30 ring carbon atoms, or a substituted or unsubstituted heteroarylene group having 2 to 30 ring carbon atoms,

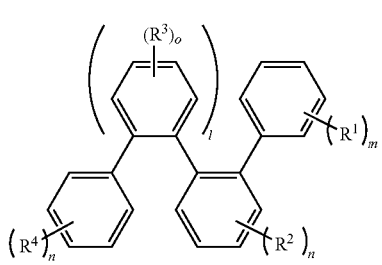

[Formula 2]

wherein, in Formula 2, $R^1$ to $R^4$ are each independently a hydrogen atom, a deuterium atom, a halogen atom, a cyano group, a substituted or unsubstituted silyl group, a substituted or unsubstituted alkyl group having 1 to 10 carbon atoms, a substituted or unsubstituted alkoxy group having 1 to 10 carbon atoms, a substituted or unsubstituted arylthio group having 1 to 10 carbon atoms, or a substituted or unsubstituted aryl group having 6 to 30 ring carbon atoms, $R^1$ to $R^4$ are separate or form a ring by combining adjacent groups with each other, l is 0 or 1, m, n, and o are each independently an integer of 0 to 4, and p is an integer of 0 to 5.

The compound represented Formula 1 may be represented by the following Formula 1-1, 1-2, or 1-6:

[Formula 1-1]
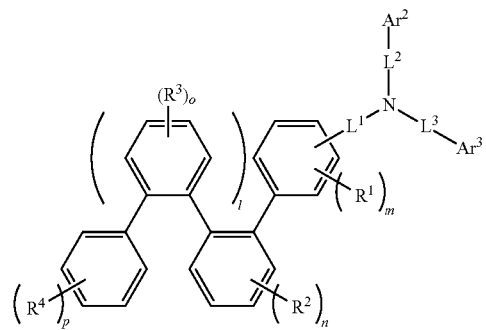
[Formula 1-2]
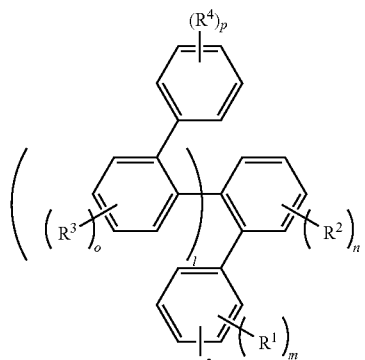
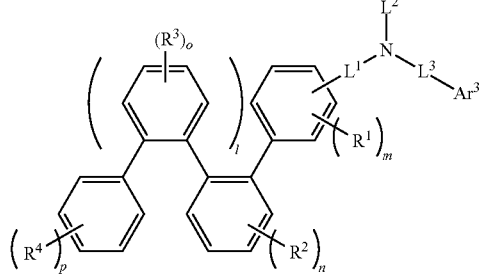
[Formula 1-6]
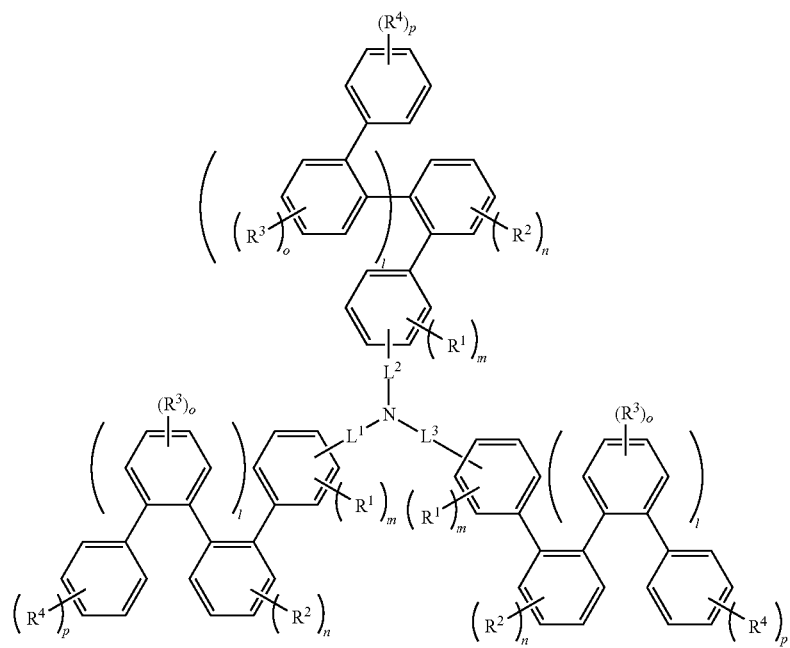

wherein, in Formulae 1-1, 1-2 and 1-6, $Ar^2$, $Ar^3$, $L^1$ to $L^3$, $R^1$ to $R^4$, and l to p may be defined the same as those of Formula 1.

The compound represented Formula 1 may be represented by one of the following Formulae 1-3 to 1-5:

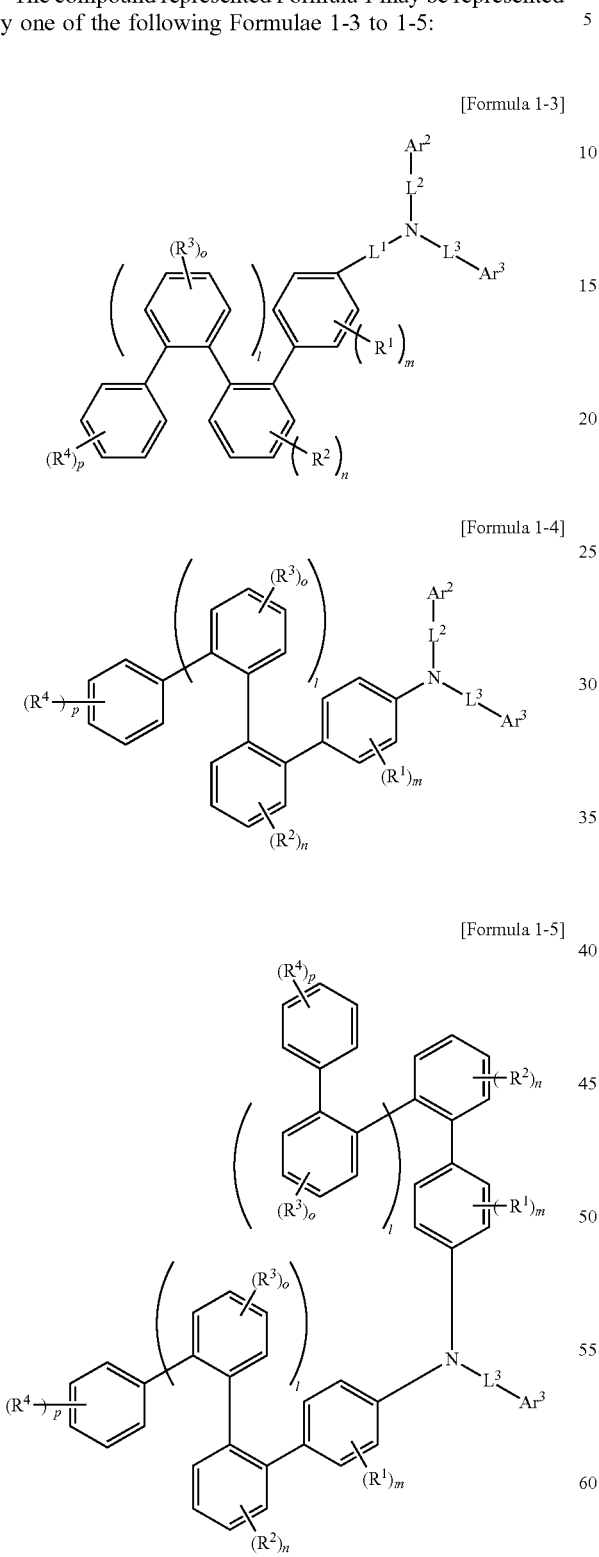

wherein, in Formulae 1-3 to 1-5, $Ar^2$, $Ar^3$, $L^1$ to $L^3$, $R^1$ to $R^4$, and l to p may be defined the same as those of Formula 1.

The group represented by Formula 2 may be a group represented by one of the following Ar-1 to Ar-10, in which * is a bonding location:

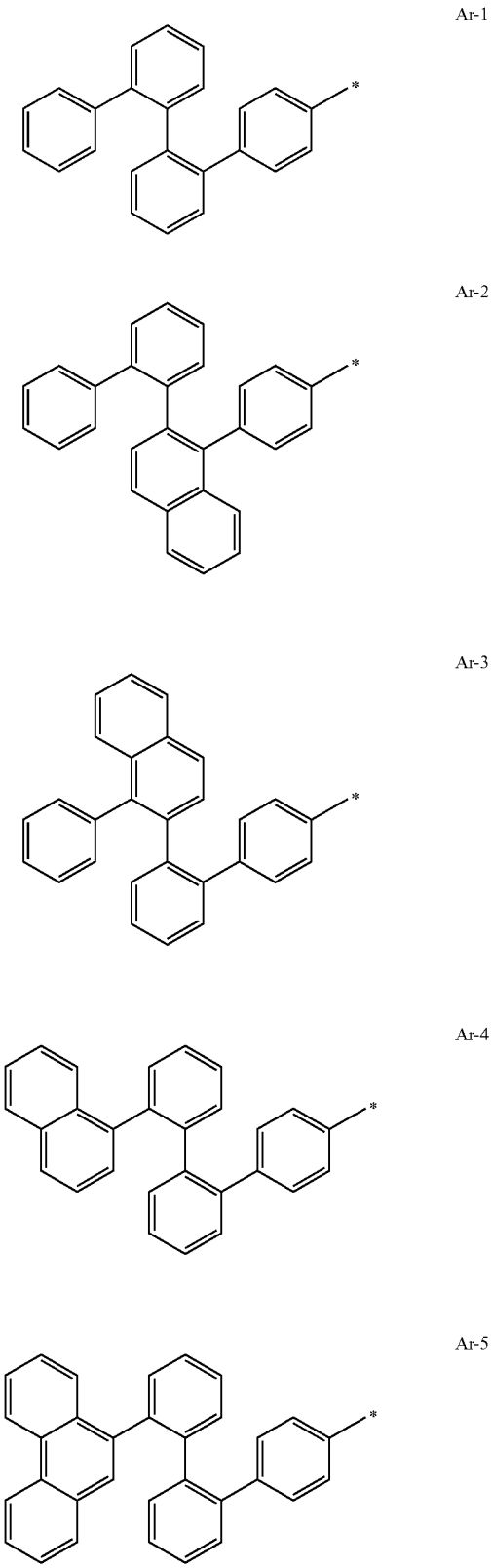

-continued

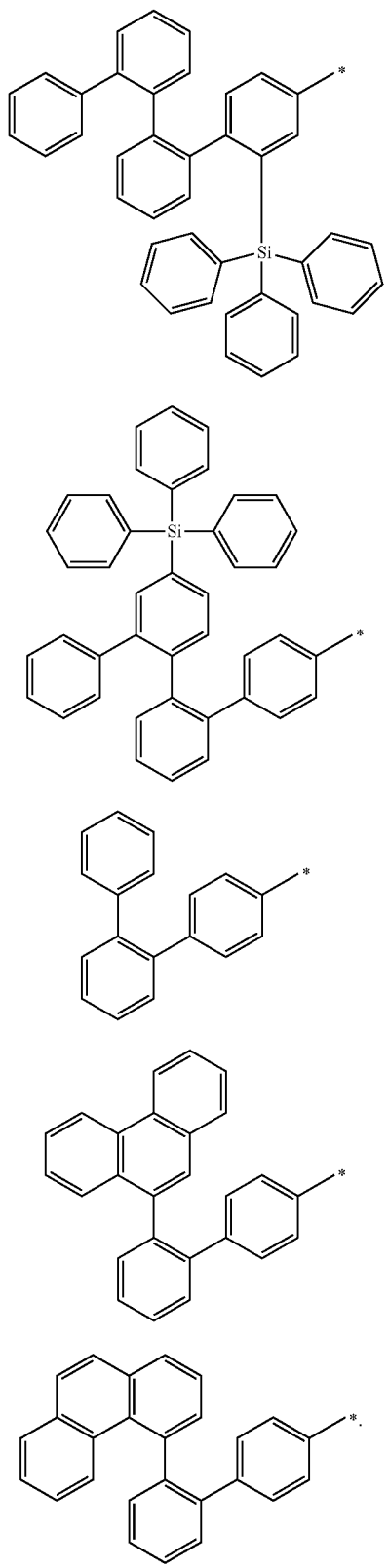

Ar² and Ar³ may each independently be a substituted or unsubstituted phenyl group, a substituted or unsubstituted biphenyl group, a substituted or unsubstituted terphenyl group, a substituted or unsubstituted naphthyl group, or a substituted or unsubstituted phenanthryl group.

Ar² and Ar³ may each independently be a group represented by one of the following Ar-11 to Ar-16, in which * is a bonding location:

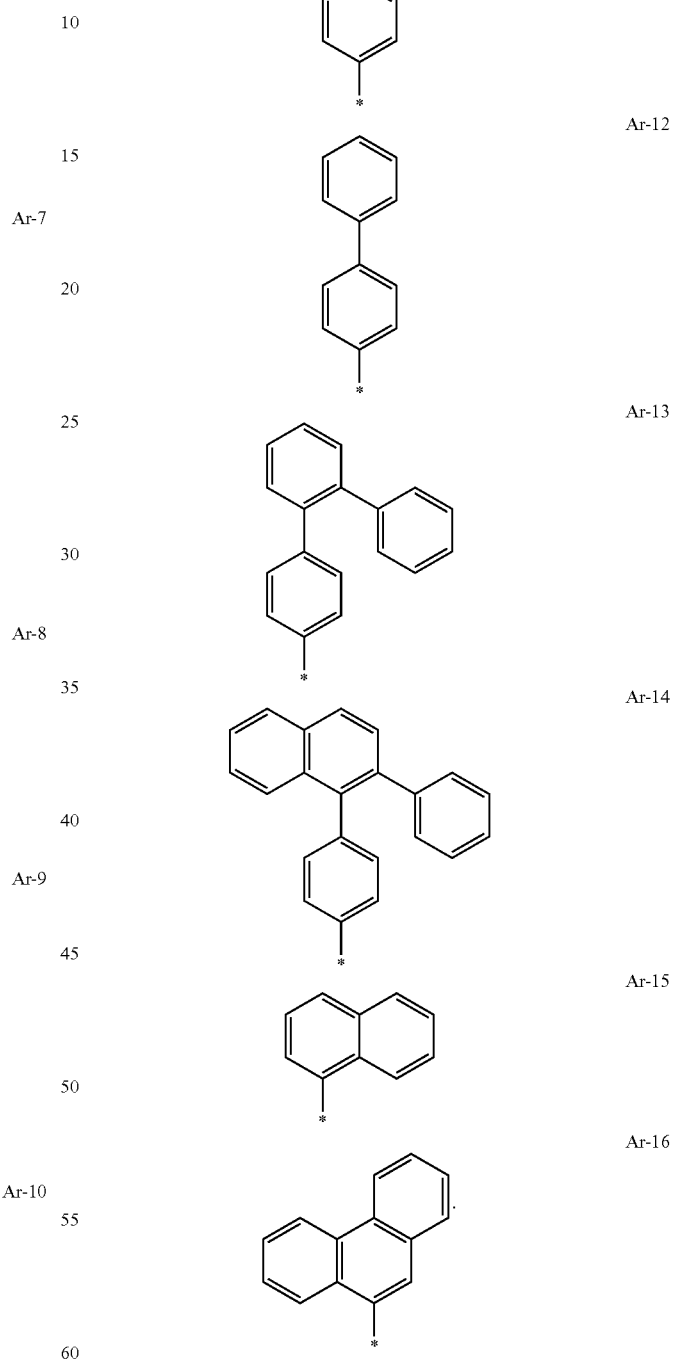

Ar² and Ar³ may each independently be a substituted or unsubstituted heteroaryl group that includes O or S as a heteroatom.

Ar² and Ar³ may each independently be a group represented by the following Ar-17 or Ar-18, which * is a bonding location:

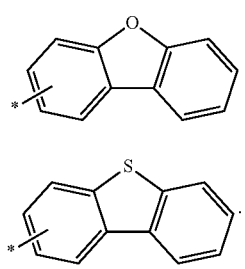
Ar² and Ar³ may each independently be a substituted or unsubstituted triphenylsilyl group.
L¹ to L³ may each independently be a direct linkage or a substituted or unsubstituted phenylene group.
The monoamine compound represented by Formula 1 may be a compound of the following Compound Group 1:
[Compound Group 1]
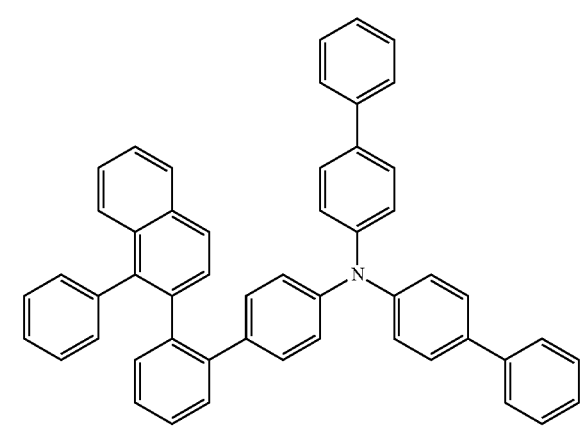
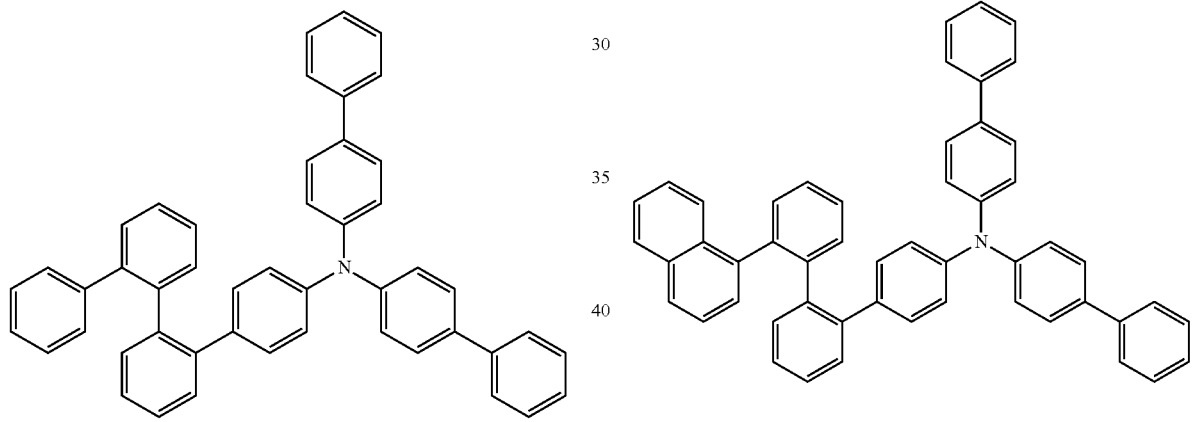
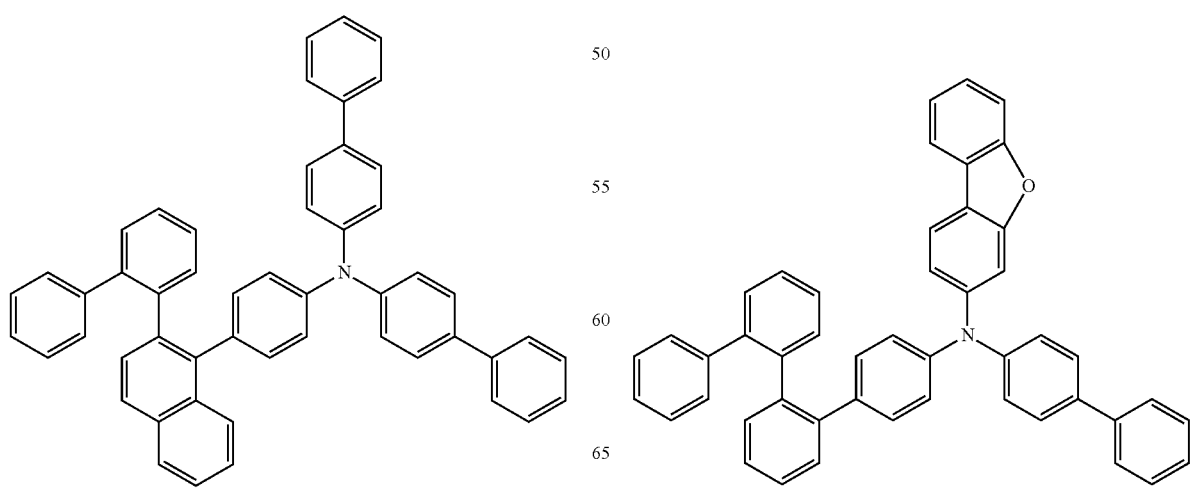

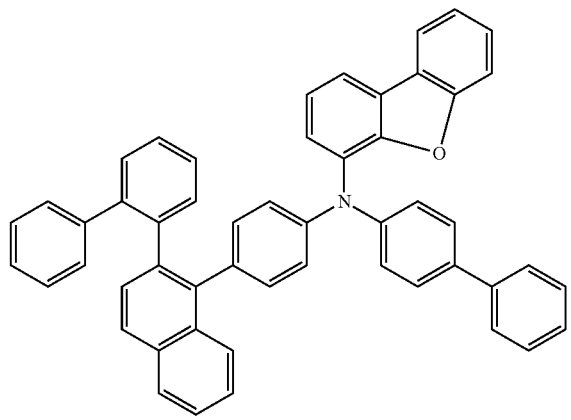
6
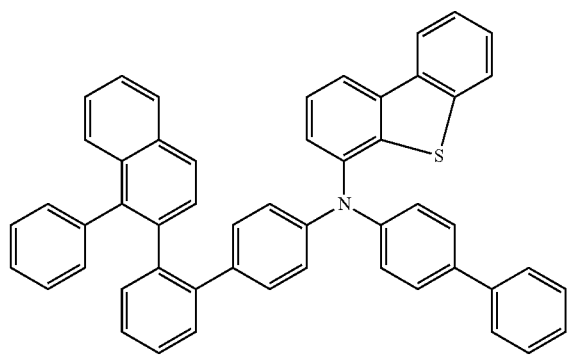
7
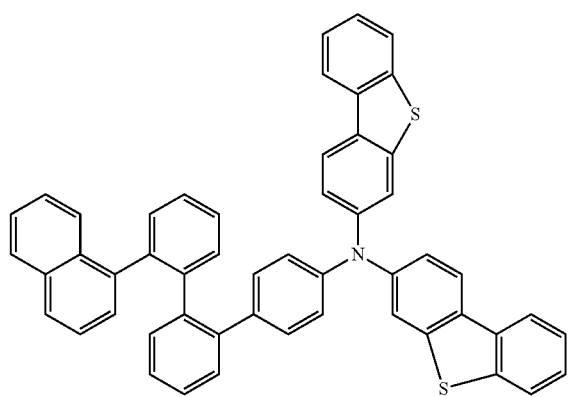
8
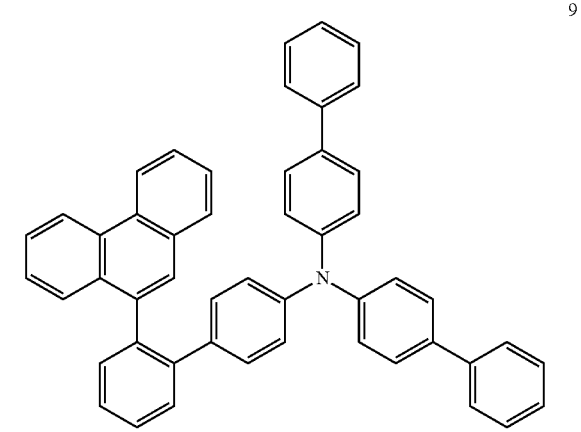
9
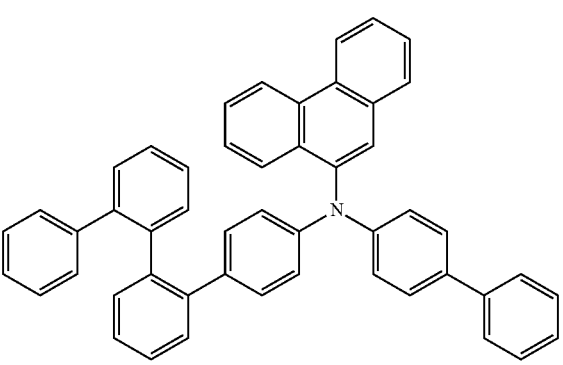
10
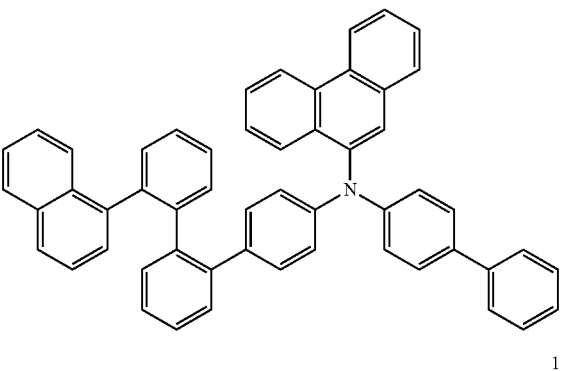
11
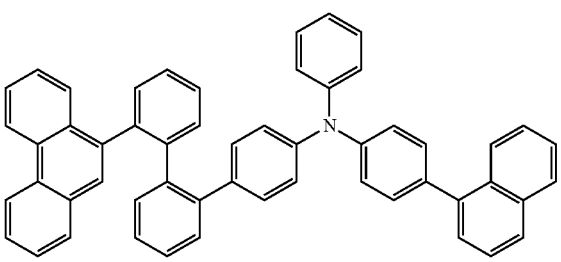
12
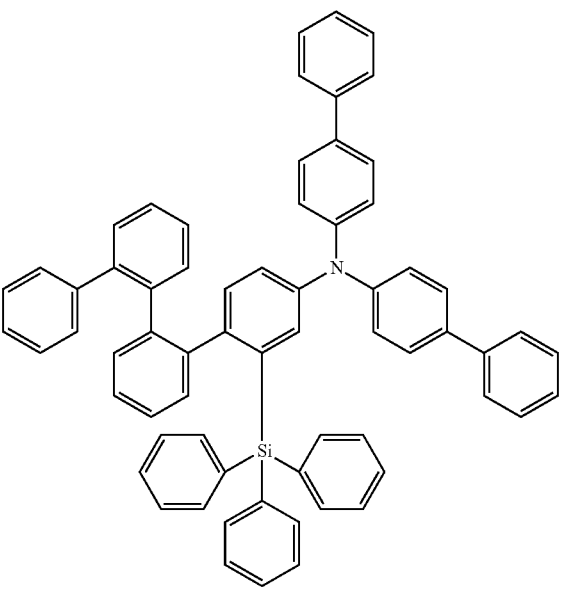
13

14
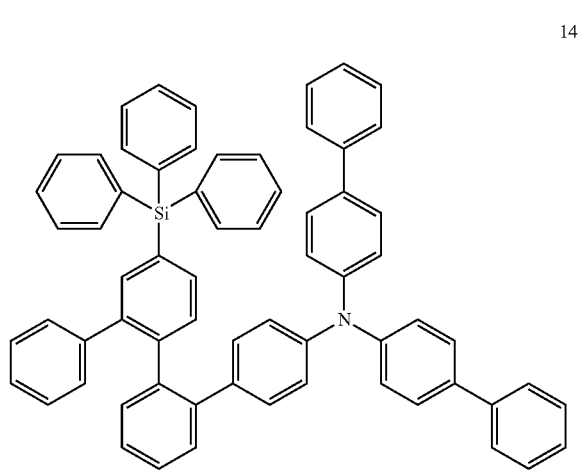
15
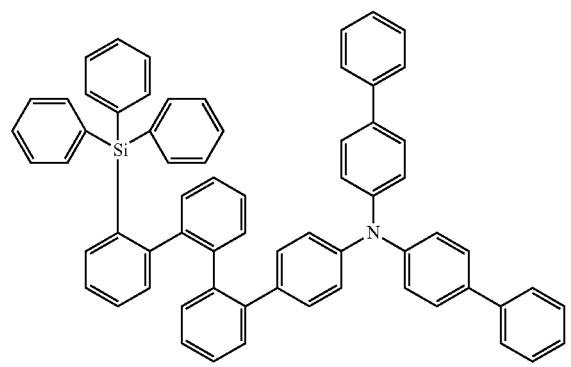
16
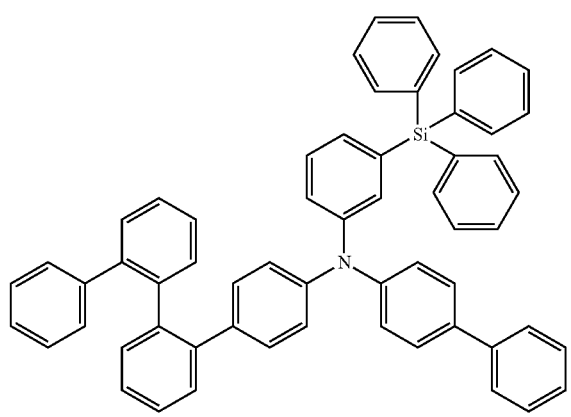
17
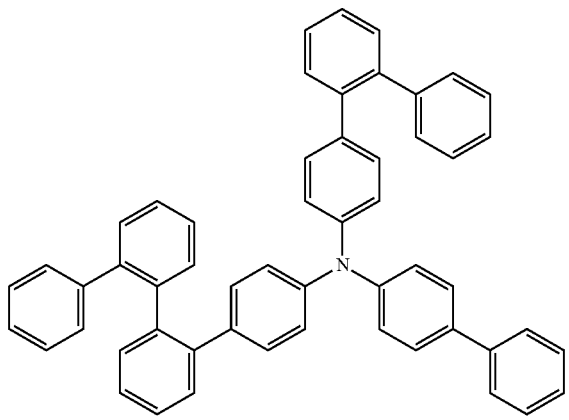
18
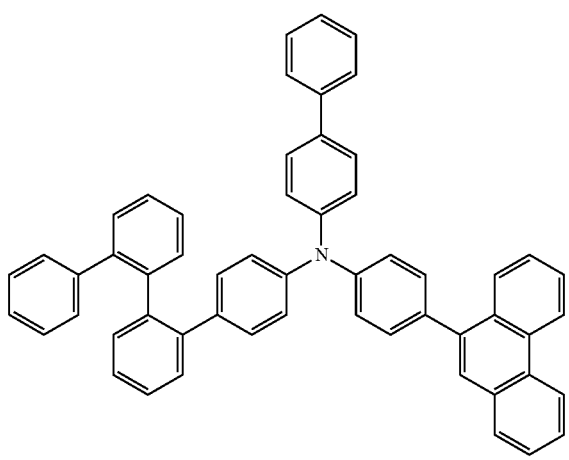
19
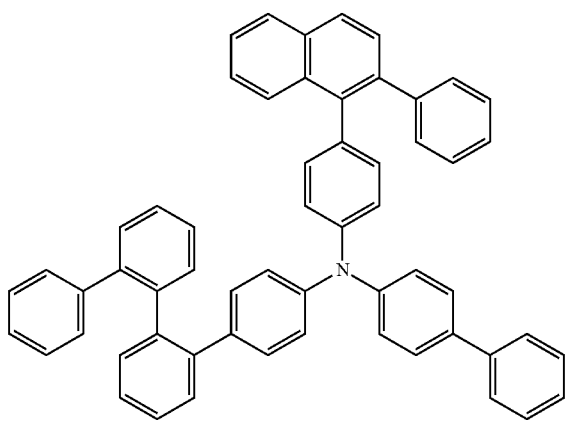

20

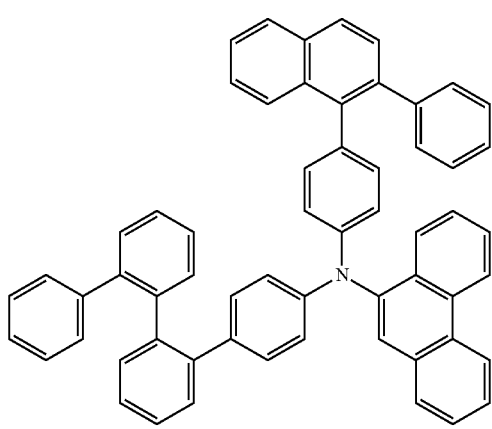

21

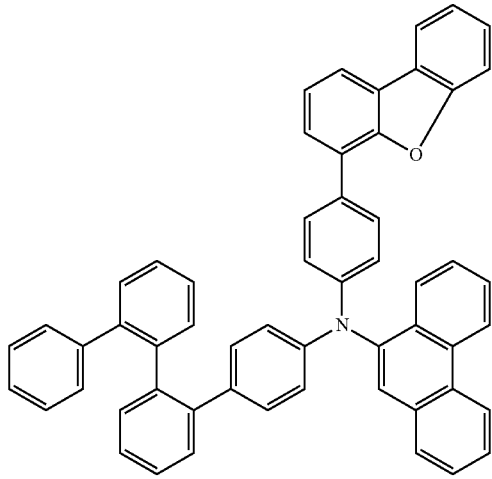

22

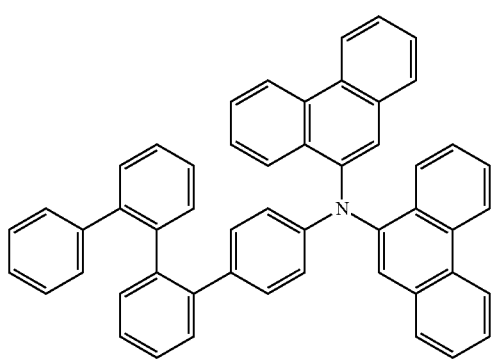

23

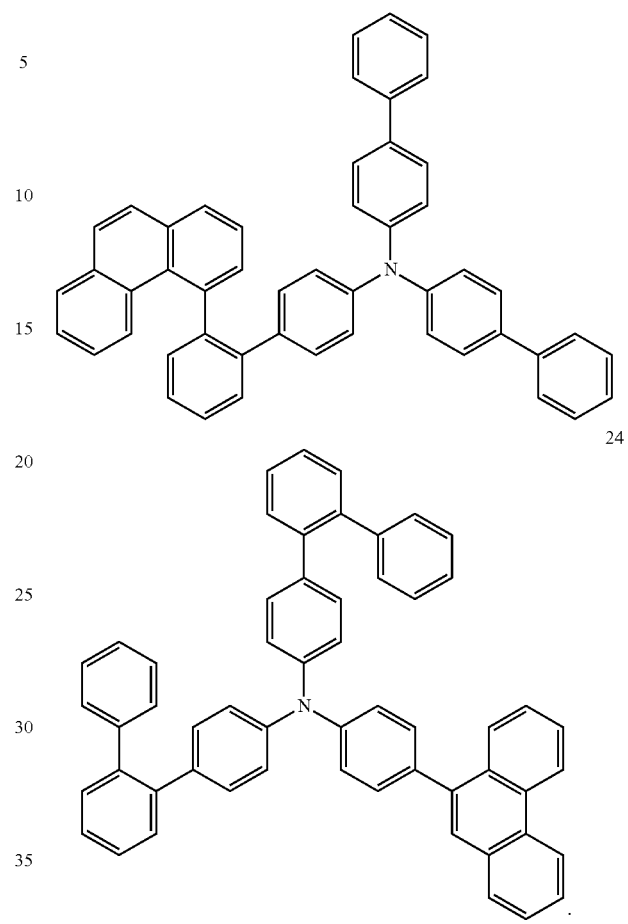

24

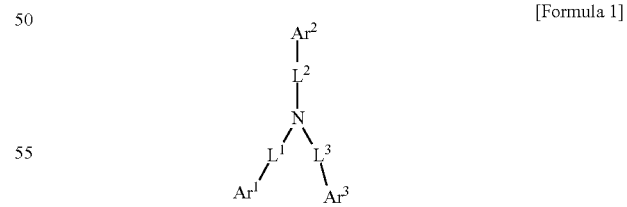

The embodiments may be realized by providing an organic electroluminescence device including a first electrode; an organic layer on the first electrode, the organic layer including a hole transport region, an emission layer, and an electron transport region; and a second electrode on the organic layer, wherein the organic layer includes an monoamine compound represented by the following Formula 1:

[Formula 1]

wherein, in Formula 1, $Ar^1$ is a group represented by the following Formula 2, $Ar^2$ and $Ar^3$ are each independently a group represented by the following Formula 2, a hydrogen atom, a deuterium atom, a halogen atom, a cyano group, a substituted or unsubstituted silyl group, a substituted or unsubstituted aryl group having 6 to 30 ring carbon atoms, or a substituted or unsubstituted heteroaryl group having 2 to 30 ring carbon atoms, $L^1$ to $L^3$ are each independently a direct linkage, a substituted or unsubstituted arylene group having 6 to 30 ring carbon atoms, or a substituted or unsubstituted heteroarylene group having 2 to 30 ring carbon atoms,

[Formula 2]

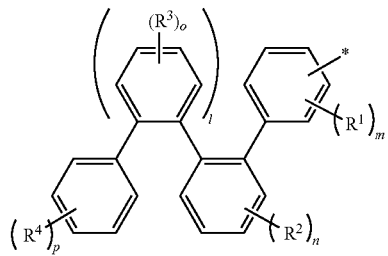

wherein, in Formula 2, $R^1$ to $R^4$ are each independently a hydrogen atom, a deuterium atom, a halogen atom, a cyano group, a substituted or unsubstituted silyl group, a substituted or unsubstituted alkyl group having 1 to 10 carbon atoms, a substituted or unsubstituted alkoxy group having 1 to 10 carbon atoms, a substituted or unsubstituted arylthio group having 1 to 10 carbon atoms, or a substituted or unsubstituted aryl group having 6 to 30 ring carbon atoms, $R^1$ to $R^4$ are separate or form a ring by combining adjacent groups with each other, l is 0 or 1, m, n, and o are each independently an integer of 0 to 4, and p is an integer of 0 to 5.

The hole transport region may include the monoamine compound represented by Formula 1.

The emission layer may emit blue light.

The compound represented Formula 1 may be represented by the following Formula 1-1, 1-2, or 1-6:

[Formula 1-1]

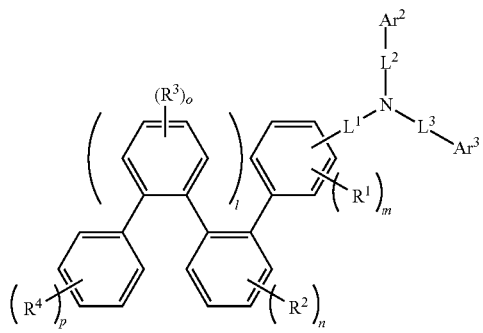

[Formula 1-2]

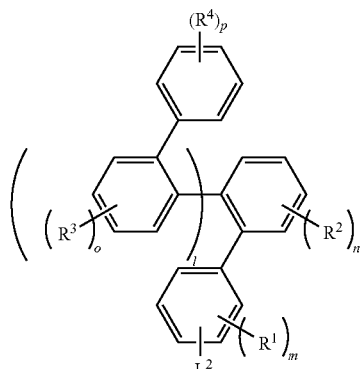

[Formula 1-6]

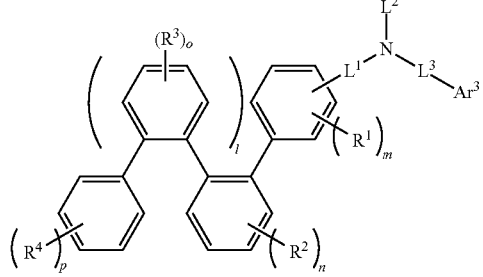

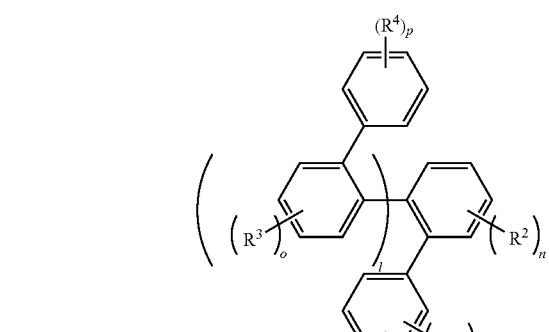

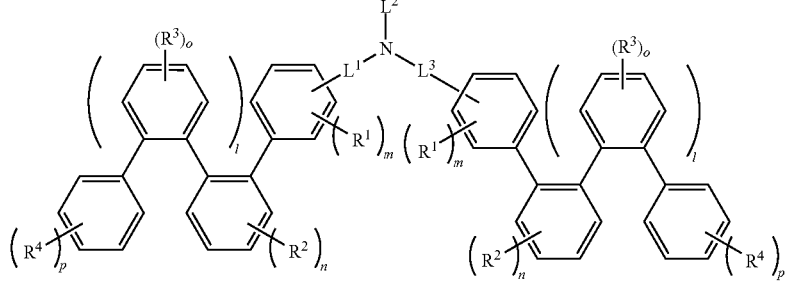

wherein, in Formulae 1-1, 1-2 and 1-6, Ar², Ar³, L¹ to L³, R¹ to R⁴, and l to p may be defined the same as those of Formula 1.

The compound represented Formula 1 may be represented by one of the following Formulae 1-3 to 1-5:

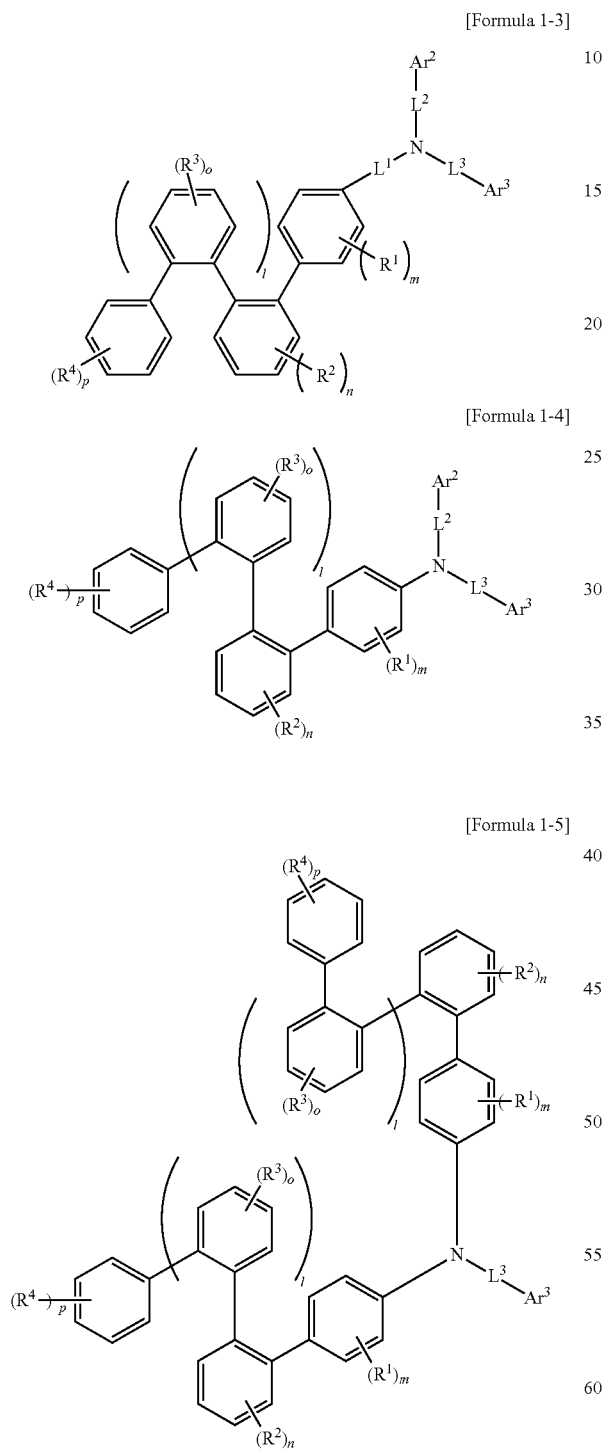

[Formula 1-3]

[Formula 1-4]

[Formula 1-5]

wherein, in Formulae 1-3 to 1-5, Ar², Ar³, L¹ to L³, R¹ to R⁴, and l to p may be defined the same as those of Formula 1.

The group represented by Formula 2 may be a group represented by one of the following Ar-1 to Ar-10, in which * is a bonding location:

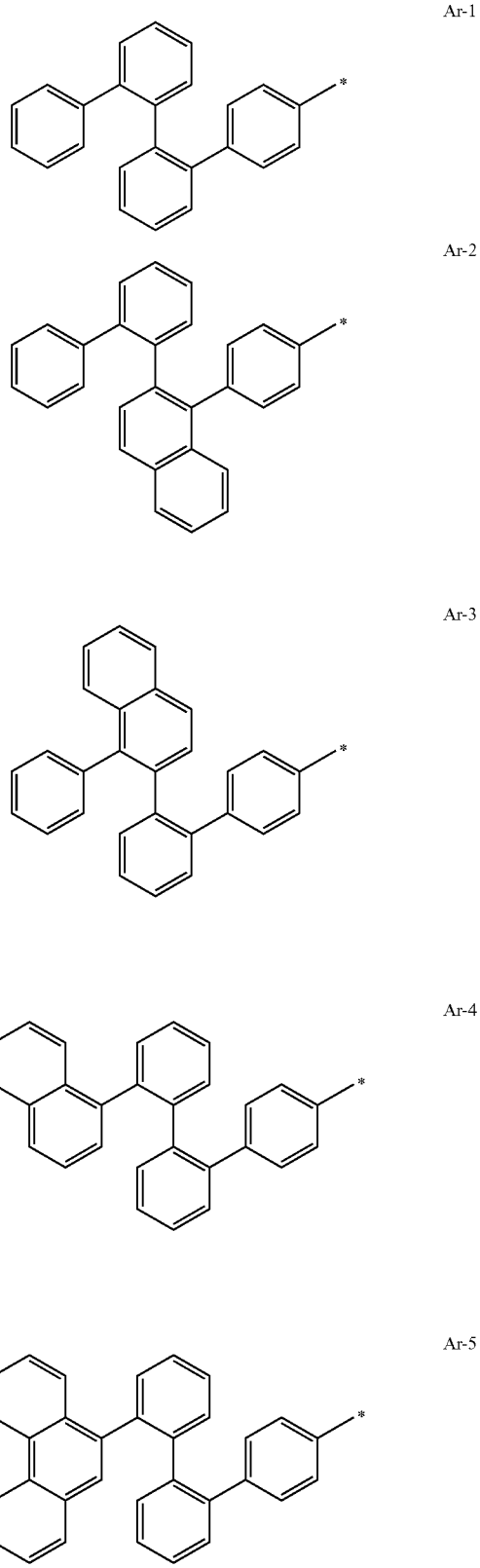

Ar-1

Ar-2

Ar-3

Ar-4

Ar-5

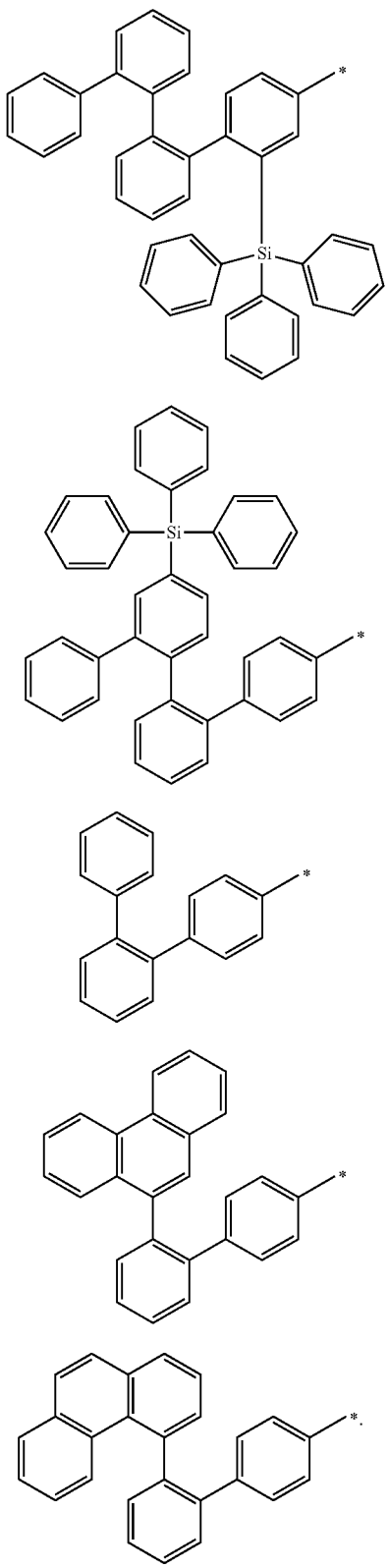

Ar² and Ar³ may each independently be a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, or a substituted or unsubstituted heteroaryl group that includes O or S as a heteroatom.

$L^1$ to $L^3$ may each independently be a direct linkage or a substituted or unsubstituted phenylene group.

The hole transport region may include the monoamine compound represented by Formula 1, and the monoamine compound represented by Formula 1 may be a compound of the following Compound Group 1:

[Compound Group 1]

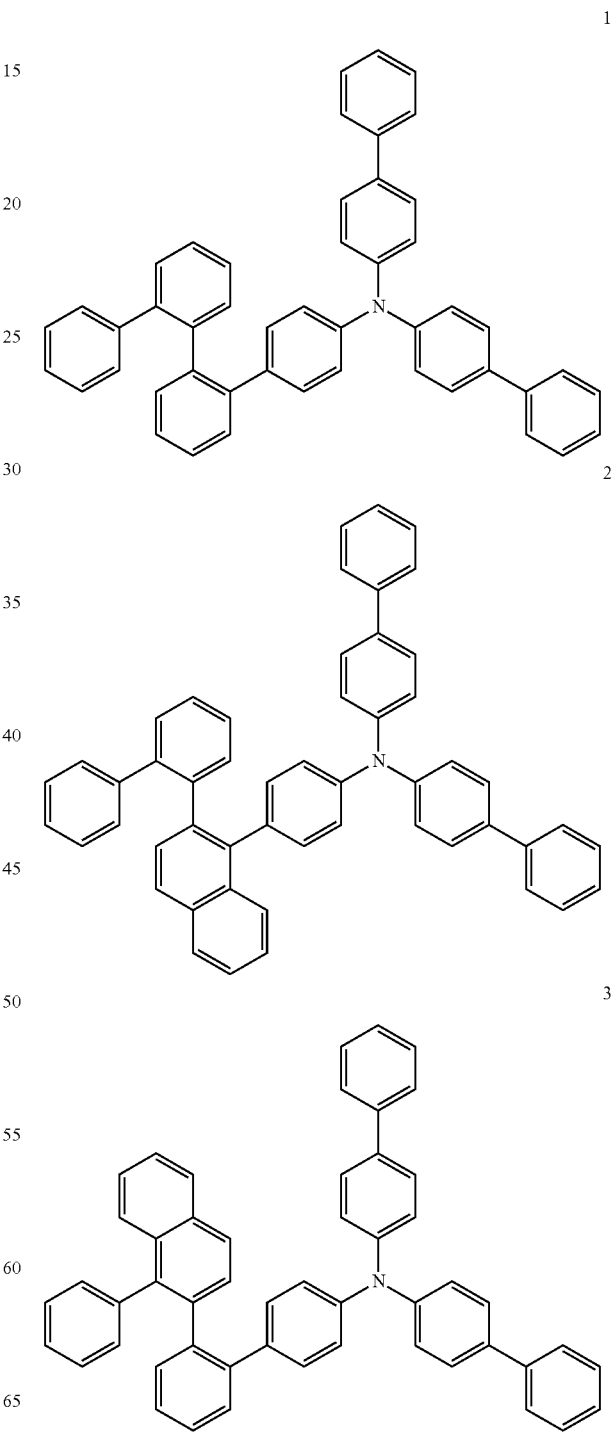

4
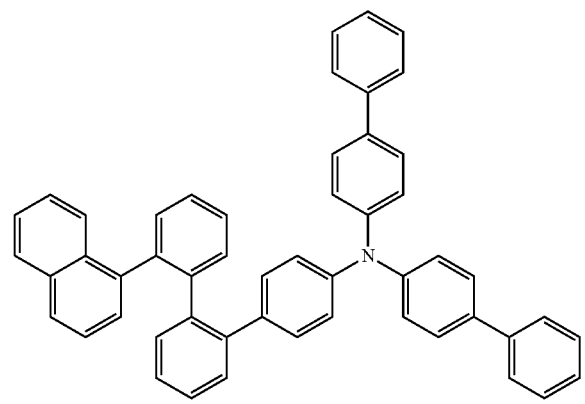
5
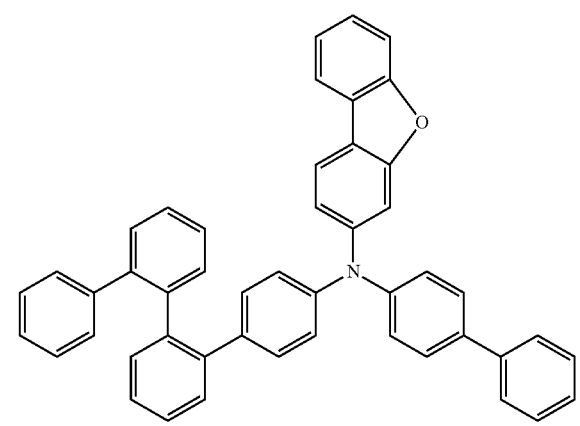
6
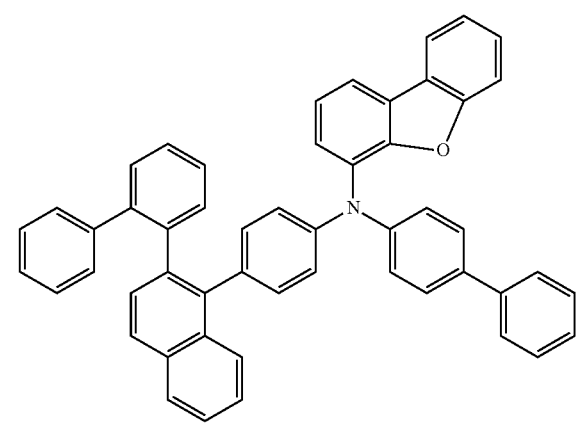
7
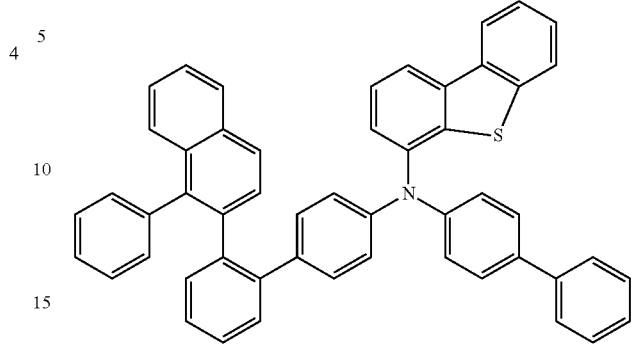
8
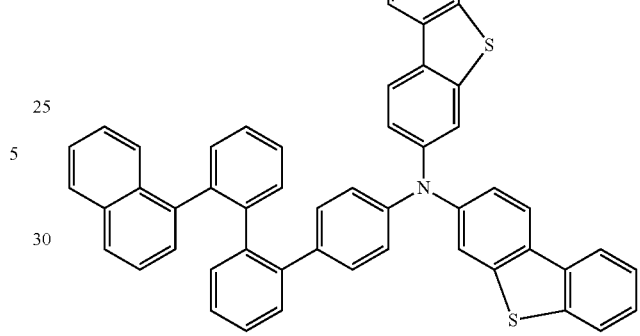
9
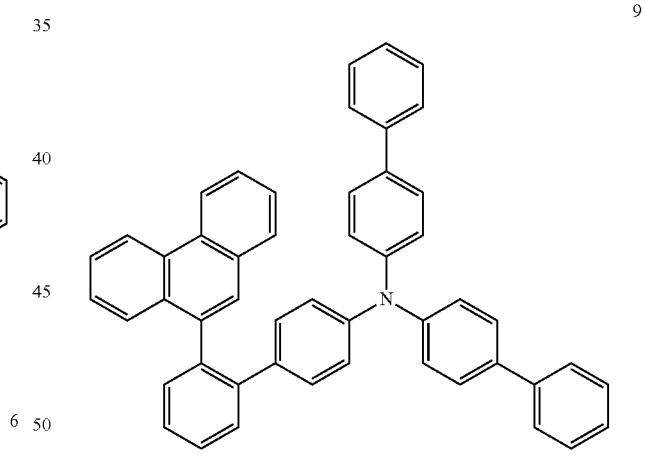
10
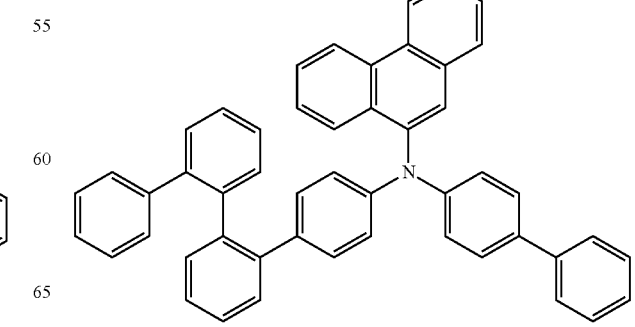

11
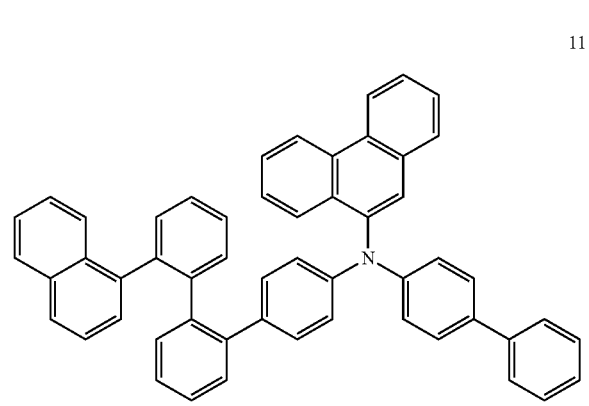
14
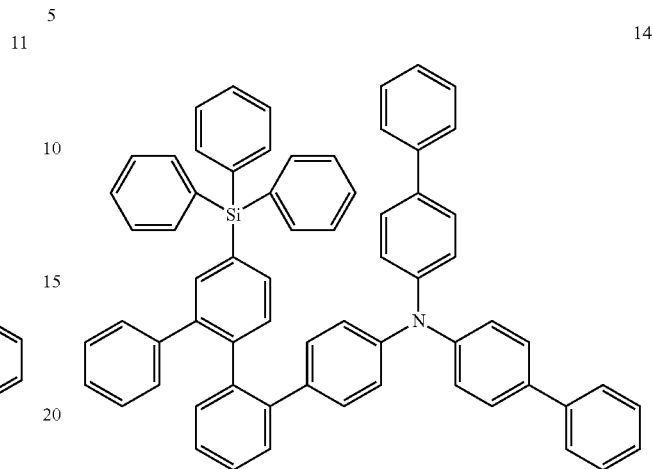
12
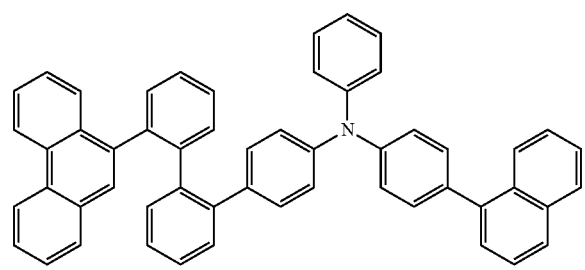
15
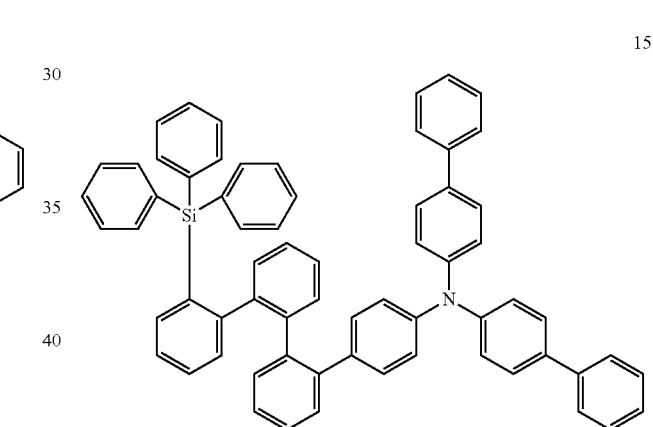
13
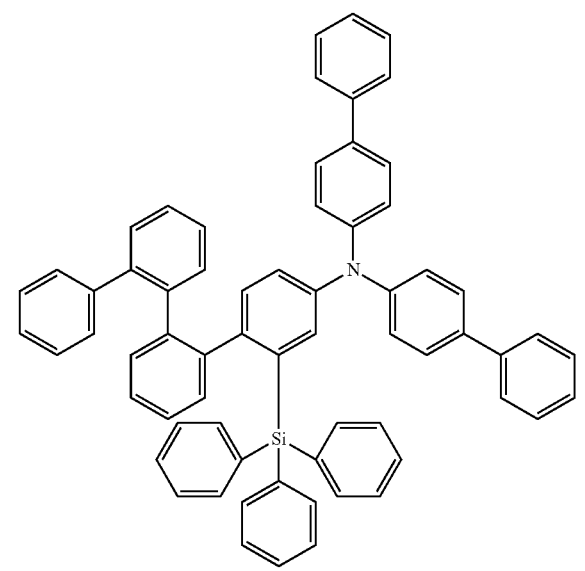
16
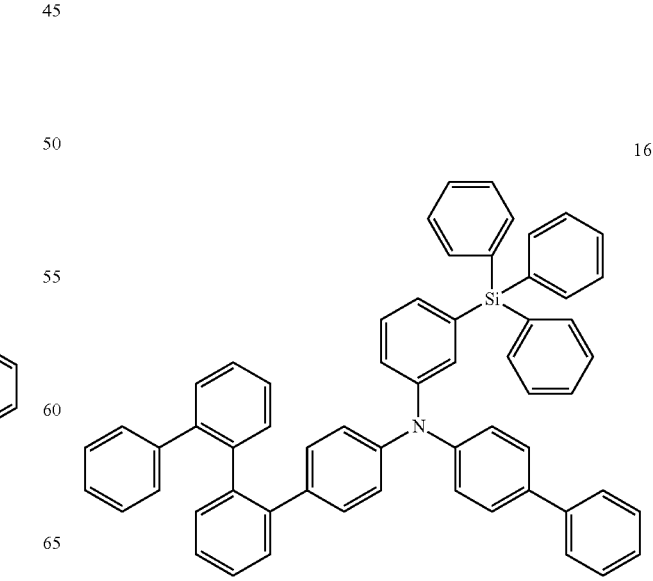

17
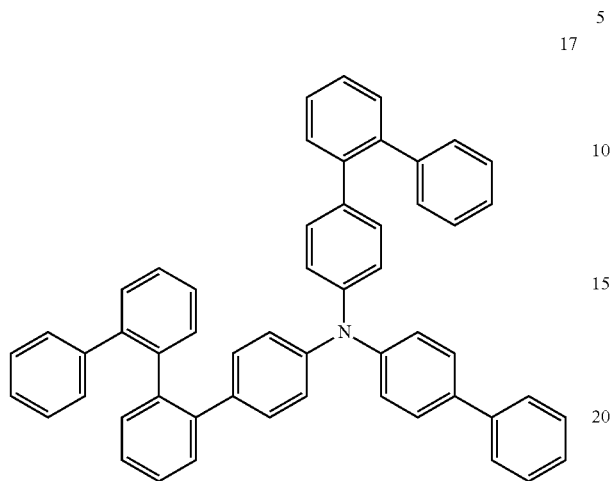
18
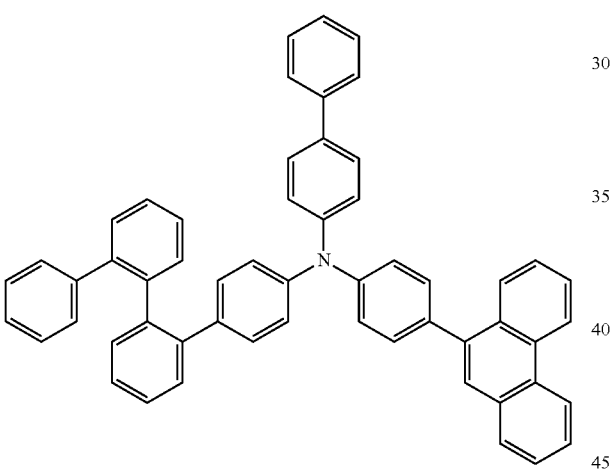
19
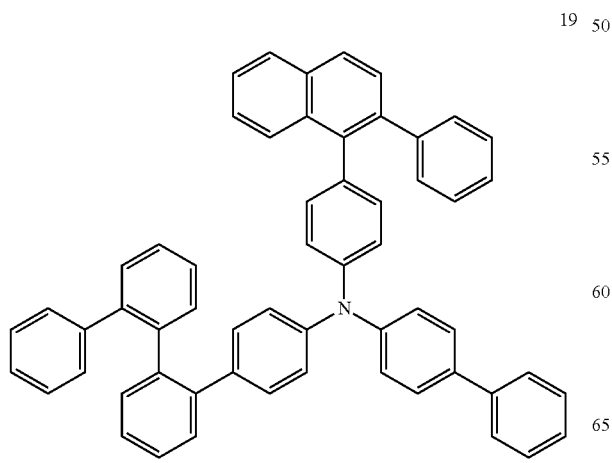
20
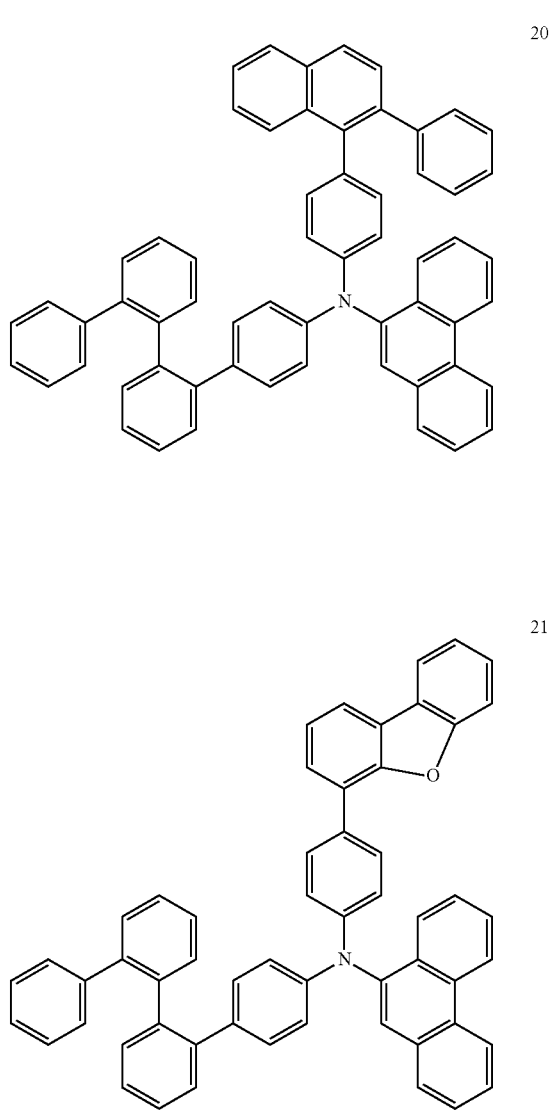
21
22
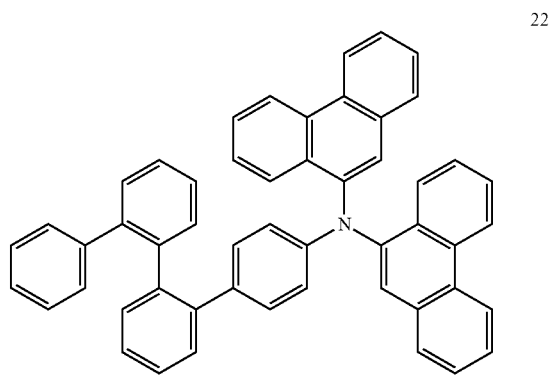

-continued

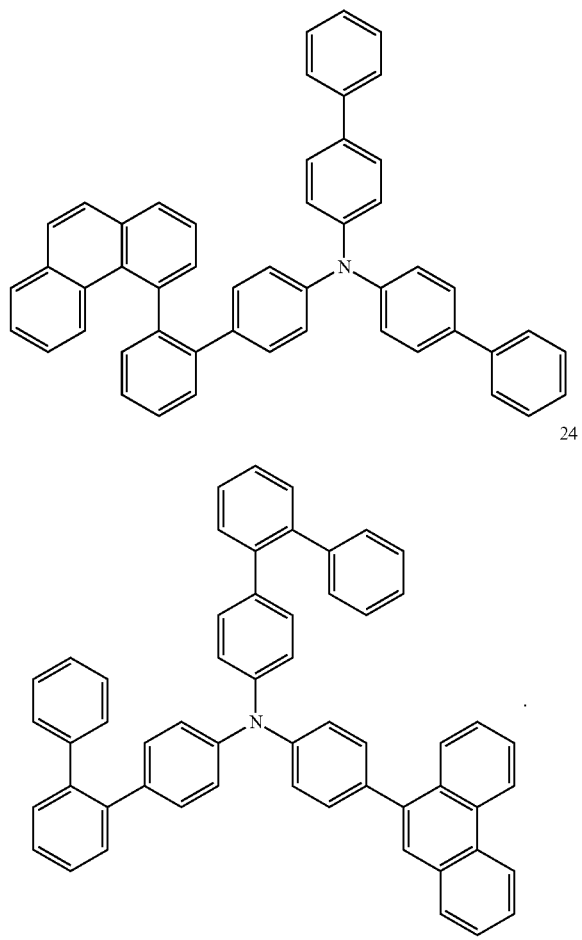

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
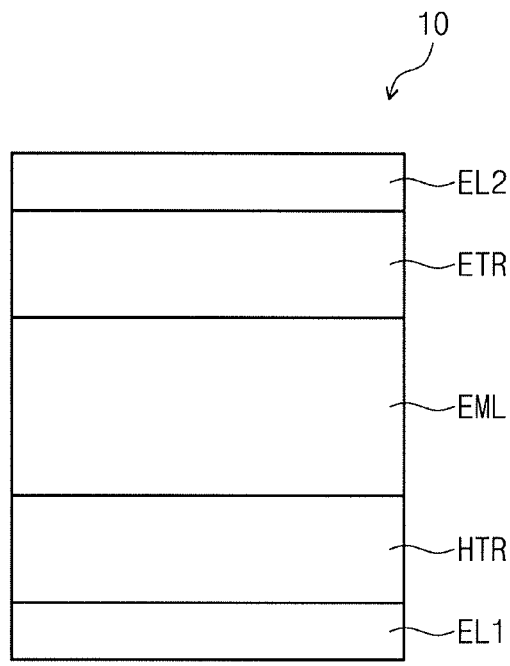
FIG. 1 illustrates a schematic cross-sectional view of an organic electroluminescence device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other layer or element, or intervening layers may also be present. In addition, it will also be understood that when a layer is referred to as being "between" two layers, it can be the only layer between the two layers, or one or more intervening layers may also be present.

Like reference numerals refer to like elements for explaining each drawing. It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise.

It will be further understood that the terms "includes," "including," "comprises" or "comprising," when used in this specification, specify the presence of stated features, numerals, steps, operations, elements, parts, or a combination thereof, but do not preclude the presence or addition of one or more other features, numerals, steps, operations, elements, parts, or a combination thereof.

In the present disclosure, ——* means a position to be connected, e.g., a bonding location.

In the present disclosure, "substituted or unsubstituted" may mean unsubstituted or substituted with at least one substituent selected from the group consisting of deuterium, halogen, nitro, amino, silyl, boron, phosphine oxide, phosphine sulfide, alkyl, alkenyl, alkynyl, aryl and heterocyclic group. In addition, each of the substituent illustrated above may be substituted or unsubstituted. For example, biphenyl may be interpreted as aryl, or phenyl substituted with phenyl.

In the present disclosure, the description of forming a ring by combining adjacent groups with each other may mean forming a substituted or unsubstituted hydrocarbon ring or a substituted or unsubstituted heterocycle by combining adjacent groups with each other. The hydrocarbon ring includes an aliphatic hydrocarbon ring and an aromatic hydrocarbon ring. The heterocycle includes an aliphatic heterocycle and an aromatic heterocycle. The hydrocarbon ring and heterocycle may be a monocycle or polycycle. In addition, the ring formed by combining adjacent groups with each other may be connected with another ring to form a spiro structure.

In the present disclosure, "an adjacent group" may mean a substituent at an atom which is directly connected with another atom at which a corresponding substituent is substituted, another substituent at an atom at which a corresponding substituent is substituted, or a substituent stereoscopically disposed at the nearest position to a corresponding substituent. For example, two methyl groups in 1,2-dimethylbenzene may be interpreted as "adjacent groups", and two ethyl groups in 1,1-diethylcyclopentene may be interpreted as "adjacent groups".

In the present disclosure, examples of a halogen atom are a fluorine atom, a chlorine atom, a bromine atom, or an iodine atom.

In the present disclosure, the alkyl group may have a linear, branched or cyclic form. The carbon number of the alkyl group may be 1 to 50, 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2- dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl group means any functional group or substituent derived from an aromatic hydrocarbon ring. The aryl group may be monocyclic aryl or polycyclic aryl. The carbon number of the aryl group for forming a ring may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylene, pyrenyl, benzofluoranthenyl, chrysenyl, etc., without limitation.

In the present disclosure, the fluorenyl group may be substituted, and two substituents may be combined with each other to form a spiro structure.

In the present disclosure, the heteroaryl group may include at least one of O, N, P, Si, or S as a heteroatom. The carbon number of the heteroaryl group for forming a ring may be 2 to 30, or 2 to 20. The heteroaryl group may be monocyclic heteroaryl or polycyclic heteroaryl. Polycyclic heteroaryl may have bicyclic or tricyclic structure, for example. Examples of the heteroaryl may include thiophene, furane, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroaryl carbazole, N-alkyl carbazole, benzoxazole, benzoimidazole, benzothiazole, benzocarbazole, benzothiophene, dibenzothiophenyl, thienothiophene, benzofuranyl, phenanthroline, thiazolyl, isoxazolyl, oxadiazolyl, thiadiazolyl, benzothiazolyl, phenothiazinyl, dibenzosilole, dibenzofuranyl, etc., without limitation.

The above explanation on the aryl group may be applied to the arylene group, except that the arylene group is divalent.

The above explanation on the heteroaryl group may be applied to the heteroarylene group, except that the heteroarylene group is divalent.

Hereinafter, the monoamine compound according to an embodiment will be explained.

The monoamine compound according to an embodiment may be represented by the following Formula 1.

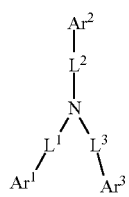

[Formula 1]

In Formula 1, $Ar^1$ may be, e.g., a group represented by the following Formula 2.

In Formula 1, $Ar^2$ and $Ar^3$ may each independently be or include, e.g., a group represented by the following Formula 2, a hydrogen atom, a deuterium atom, a halogen atom, a cyano group, a substituted or unsubstituted silyl group, a substituted or unsubstituted aryl group having 6 to 30 ring carbon atoms, or a substituted or unsubstituted heteroaryl group having 2 to 30 ring carbon atoms.

In Formula 1, $L^1$ to $L^3$ may each independently be or include, e.g., a direct linkage, a substituted or unsubstituted arylene group having 6 to 30 ring carbon atoms, or a substituted or unsubstituted heteroarylene group having 2 to 30 ring carbon atoms.

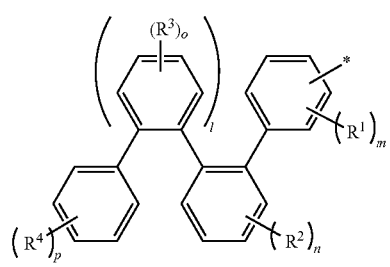

[Formula 2]

In Formula 2, $R^1$ to $R^4$ may each independently be or include, e.g., a hydrogen atom, a deuterium atom, a halogen atom, a cyano group, a substituted or unsubstituted silyl group, a substituted or unsubstituted alkyl group having 1 to 10 carbon atoms, a substituted or unsubstituted alkoxy group having 1 to 10 carbon atoms, a substituted or unsubstituted arylthio group having 1 to 10 carbon atoms, or a substituted or unsubstituted aryl group having 6 to 30 ring carbon atoms. In an implementation, $R^1$ to $R^4$ may be separate or may form a ring by combining adjacent groups with each other. In an implementation, $R^1$ to $R^4$ may not all be a heteroaryl group, e.g., such a compound is excluded. In an implementation, $R^1$ to $R^4$ may each independently be or include, e.g., a hydrogen atom, a substituted or unsubstituted phenyl group, or a substituted or unsubstituted silyl group.

In Formula 2, l may be 0 or 1, m, n and o may be each independently an integer of 0 to 4, and p may be an integer of 0 to 5. For example, it will be understood that m being 1 and $R^1$ being hydrogen is the same as m being 0, etc.

In Formula 1, $Ar^1$ may be, e.g., a group represented by Formula 2, and $Ar^2$ and $Ar^3$ may each independently be or include, e.g., a substituted or unsubstituted phenyl group, a substituted or unsubstituted biphenyl group, a substituted or unsubstituted terphenyl group, a substituted or unsubstituted naphthyl group, or a substituted or unsubstituted phenanthryl group, a substituted or unsubstituted triphenylsilyl group, or a substituted or unsubstituted heteroaryl group including O or S as a heteroatom.

In Formula 2, when m, n, o, or p is an integer of 2 or more, a plurality of $R^1$, $R^2$, $R^3$, or $R^4$ may be the same or different from each other. For example, when m is 2, two $R^1$s may be the same or different from each other. Furthermore, when m is 3, three $R^1$s may be different from each other, two $R^1$s may be the same each other and one $R^1$ may be different, or three $R^1$s may be the same each other.

In an implementation, a case where n, o, or p is an integer of 2 or more, may be equally applied as described above. For example, a plurality of substituents may be the same or different from each other.

In an implementation, in Formula 1, among $Ar^1$ to $Ar^3$, only $Ar^1$ may be represented by Formula 2, $Ar^1$ and $Ar^2$ may be represented by Formula 2, or all of $Ar^1$ to $Ar^3$ may be represented by Formula 2.

For example, the monoamine compound represented by Formula 1 may be represented by one of the following Formula 1-1, 1-2, or 1-6.

In Formulae 1-1, 1-2 and 1-6, $Ar^2$, $Ar^3$, L to $L^3$, $R^1$ to $R^4$, and l to p may be defined the same as those of Formulae 1 and 2.

Formula 1-1 represents the monoamine compound of Formula 1 in which $Ar^1$ is represented by Formula 2, and Formula 1-2 represents the monoamine compound of Formula 1 in which $Ar^1$ and $Ar^2$ are represented by Formula 2.

[Formula 1-1]

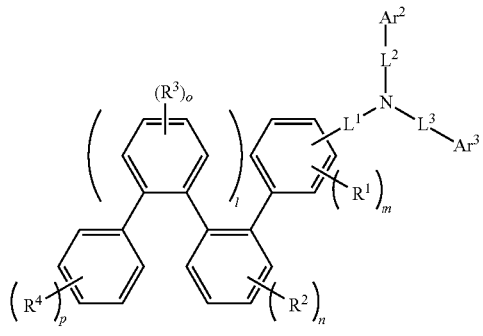

[Formula 1-2]

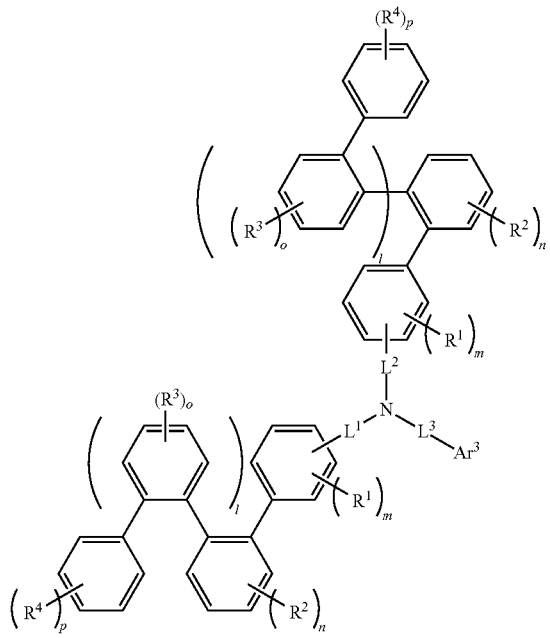

[Formula 1-6]

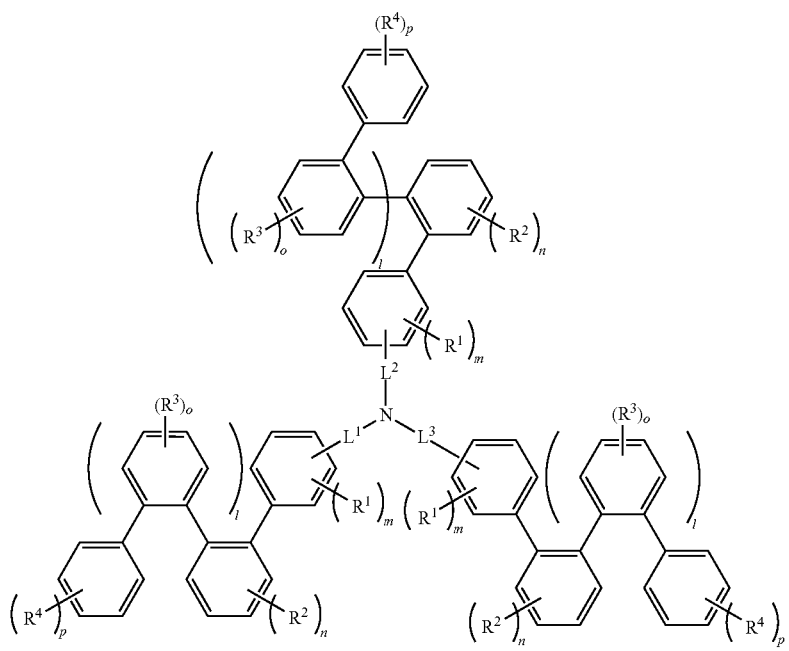

As in the monoamine compound of Formula 1-6, all of $Ar^1$ to $Ar^3$ may be represented by Formula 2. In Formulae 1-1, 1-2 and 1-6, $R^1$ to $R^4$ may each independently be or include, e.g., a hydrogen atom, a substituted or unsubstituted phenyl group, or a substituted or unsubstituted silyl group.

In an implementation, the compound represented by Formula 1 may be represented by one of the following Formulae 1-3 to 1-5.

In Formulae 1-3 to 1-5, $R^1$ to $R^4$, and l to p may be defined the same as those of Formulae 1 and 2.

In an implementation, $L^1$ to $L^3$ may each independently be or include, e.g., a direct linkage or a substituted or unsubstituted phenylene group.

In an implementation, $Ar^2$ and $Ar^3$ may each independently be or include, e.g., a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted triphenylsilyl group, or a substituted or unsubstituted heteroaryl group including O or S as a heteroatom.

$R^1$ to $R^4$ may each independently be or include, e.g., a hydrogen atom, a substituted or unsubstituted phenyl group, or a substituted or unsubstituted silyl group.

In an implementation, in Formula 1, $Ar^1$ (e.g., the group represented by Formula 2) may be a group represented by one of the following Ar-1 to Ar-10.

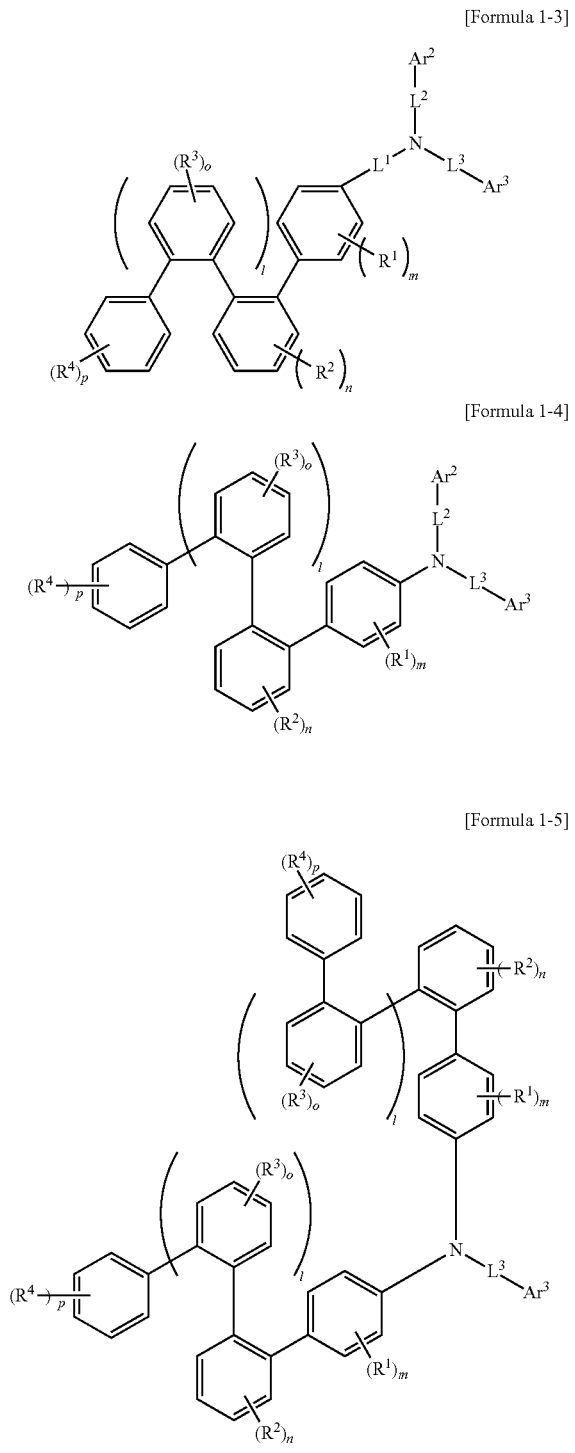
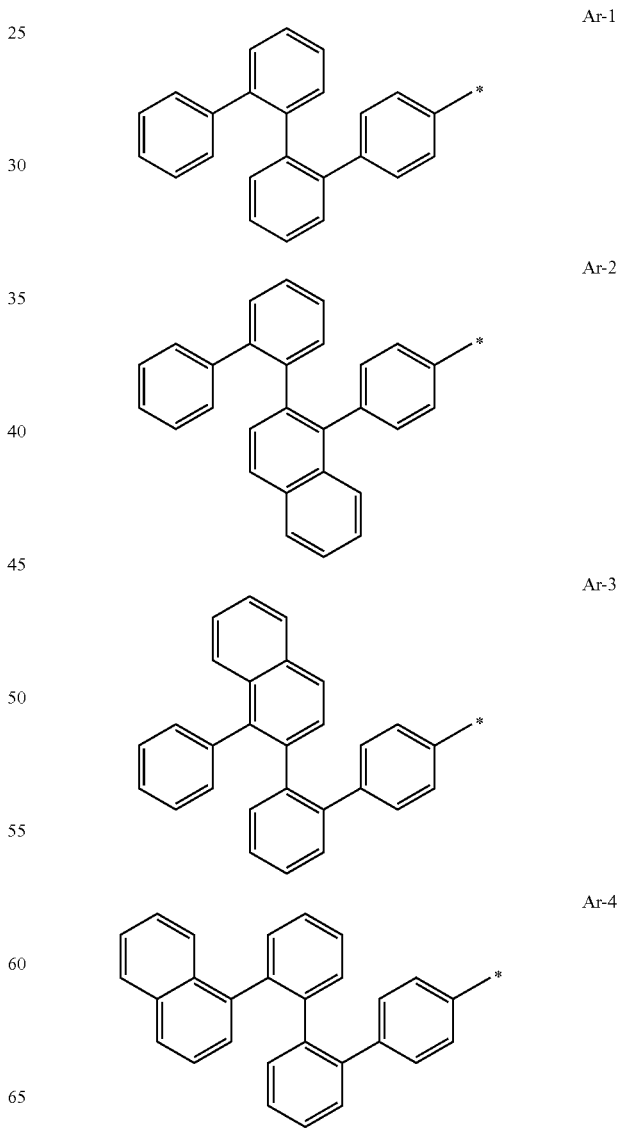

Ar-5
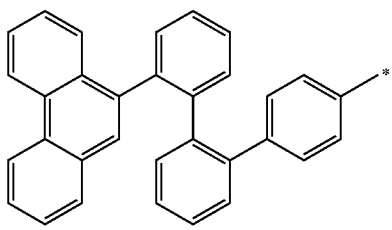

Ar-6
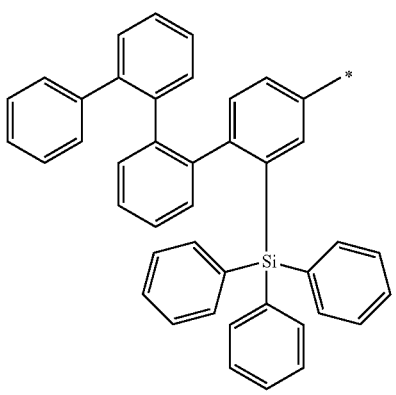

Ar-7
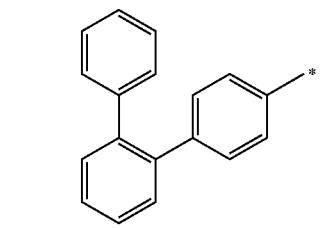

Ar-8
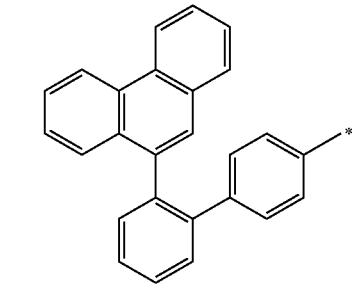

Ar-9
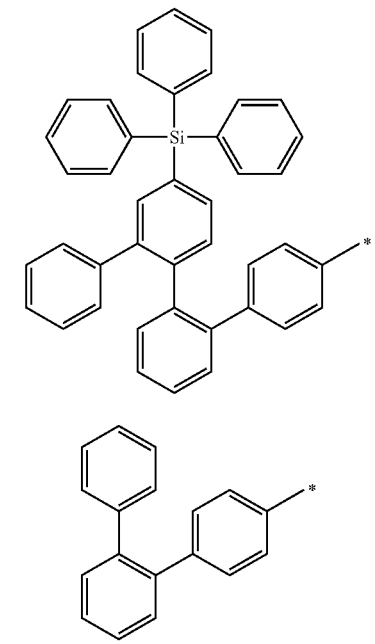

Ar-10
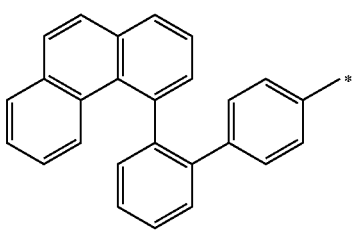

In Formula 1, $L^1$ may be a direct linkage, and $Ar^1$ may be a group represented by one of Ar-1 to Ar-10.

In an implementation, in Formula 1, $Ar^2$ and $Ar^3$ may each independently be or include, e.g., a substituted or unsubstituted phenyl group, a substituted or unsubstituted biphenyl group, a substituted or unsubstituted terphenyl group, a substituted or unsubstituted naphthyl group, or a substituted or unsubstituted phenanthryl group. Furthermore, Ar2 and Ar3 may be each independently an unsubstituted phenyl group, an unsubstituted biphenyl group, a substituted or unsubstituted terphenyl group, an unsubstituted naphthyl group, or an unsubstituted phenanthryl group.

In an implementation, $Ar^2$ and $Ar^3$ may each independently be, e.g., a group represented by one of the following Ar-11 to Ar-16.

Ar-11
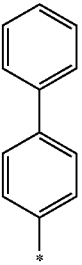

Ar-12

Ar-13
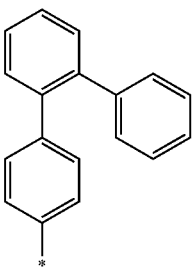

Ar-14
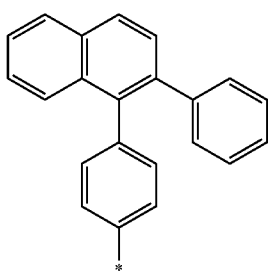

Ar-15
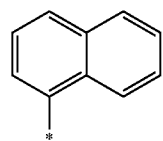

Ar-16
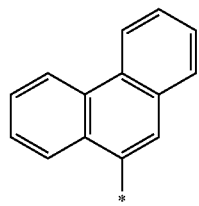

In an implementation, in the monoamine compound represented by Formula 1, $L^2$ and $L^3$ may both be a direct linkage, and $Ar^2$ and $Ar^3$ may each independently be a group represented by one of Ar-11 to Ar-16.

In an implementation, $Ar^2$ and $Ar^3$ may each independently be or include, e.g., a substituted or unsubstituted heteroaryl group including O or S as a heteroatom. In an implementation, $Ar^2$ and $Ar^3$ may each independently be or include, e.g., a dibenzofuranyl group or a dibenzothiophenyl group. In an implementation, $Ar^2$ and $Ar^3$ may each independently be or include, e.g., a heteroarylene group represented by the following Ar-17 or Ar-18:

Ar-17
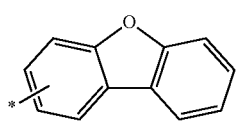

Ar-18
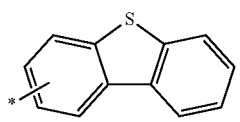

In an implementation, $Ar^2$ and $Ar^3$ may each independently be or include, e.g., a substituted or unsubstituted triarylsilyl group. In an implementation, $Ar^2$ and $Ar^3$ may each independently be or include, e.g., a triphenylsilyl group.

In an implementation, $L^1$ to $L^3$ may each independently be or include, e.g., a direct linkage or a substituted or unsubstituted phenylene group. In an implementation, $L^1$ to $L^3$ may each independently be a direct linkage or an unsubstituted phenylene group.

In an implementation, the monoamine compound represented by Formula 1 may be, e.g., a compound of the following Compound Group 1.

[Compound Group 1]

1
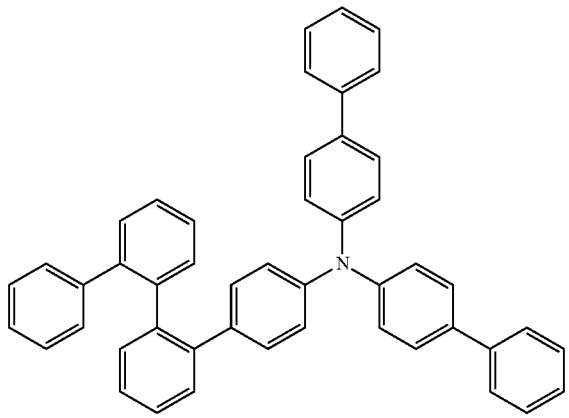

2
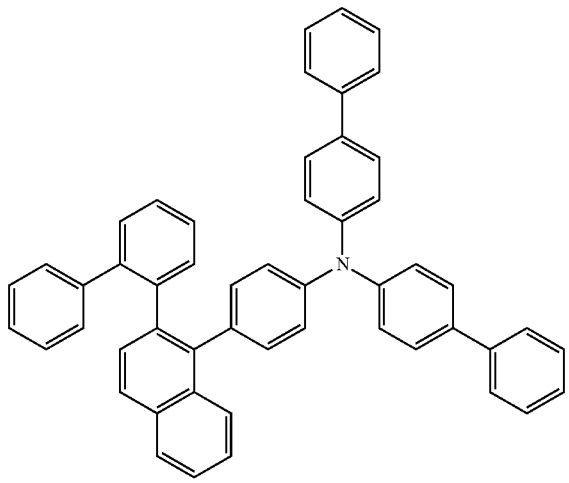

3
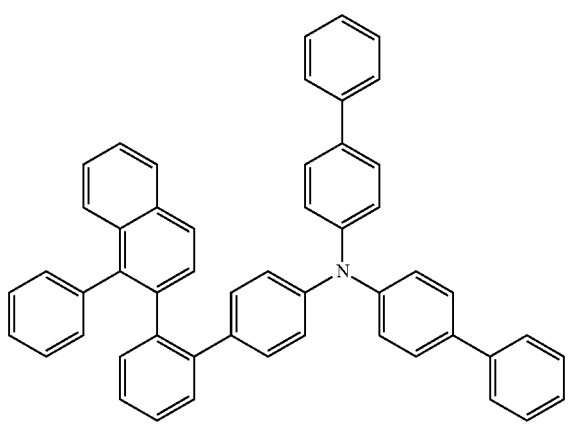

41
-continued
4
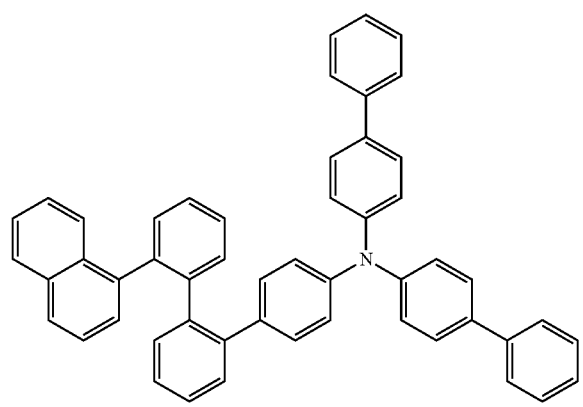
5
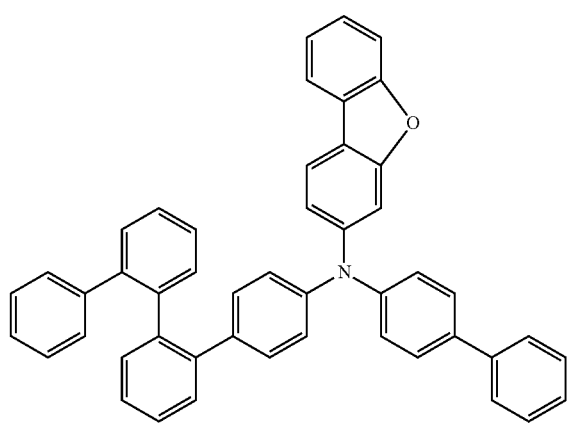
6
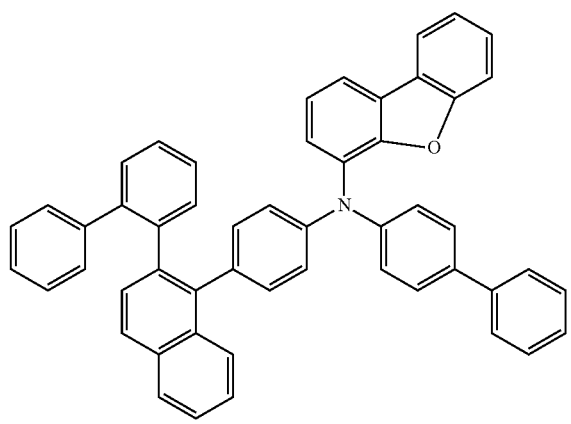
42
-continued
7
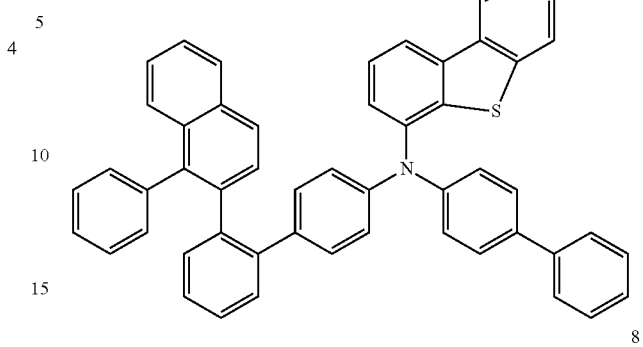
8
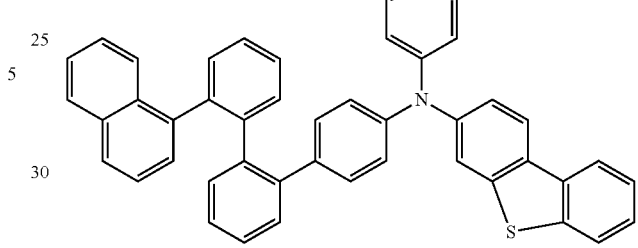
9
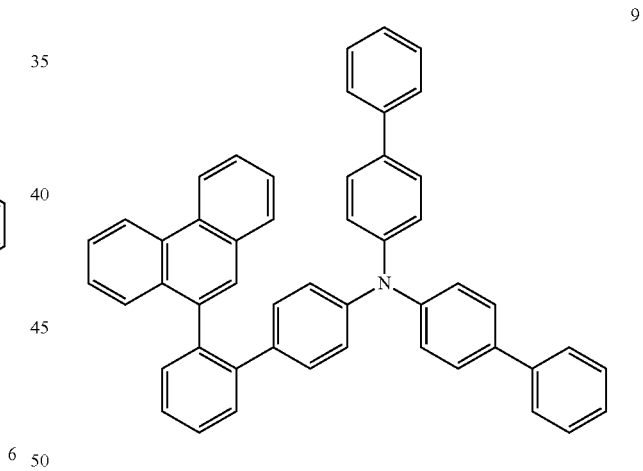
10
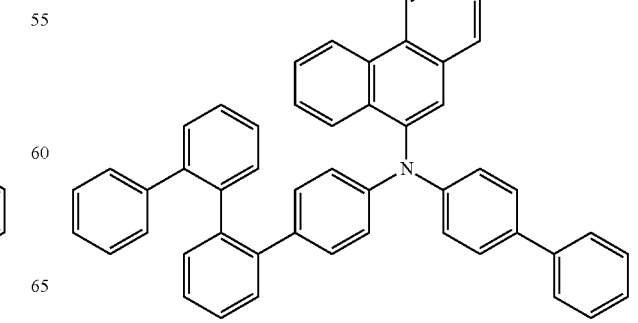

11
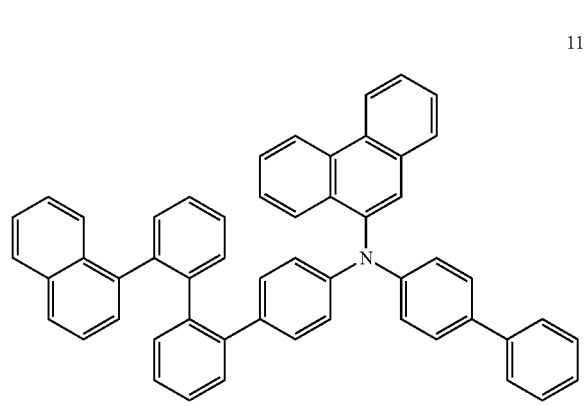
12
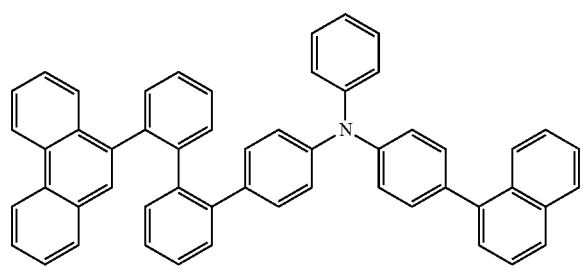
13
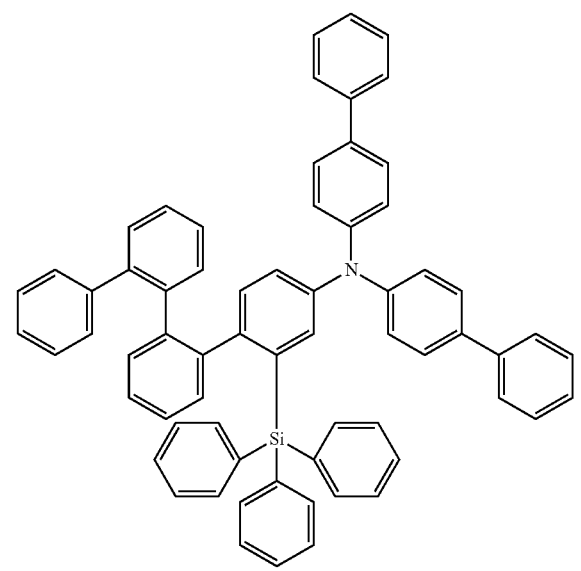
14
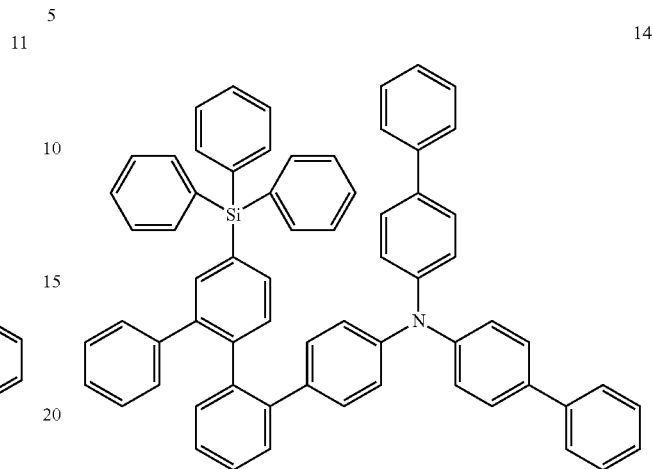
15
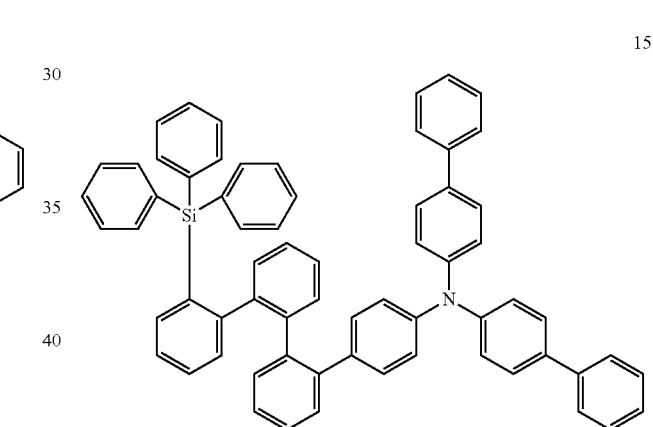
16
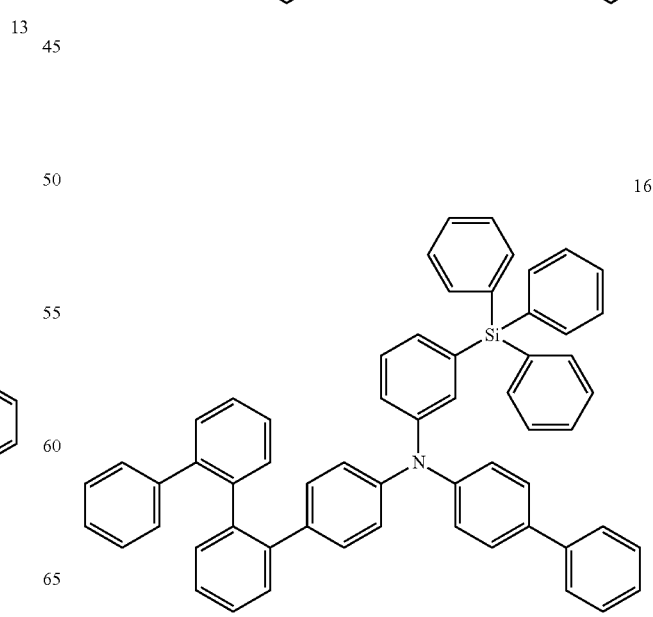

17
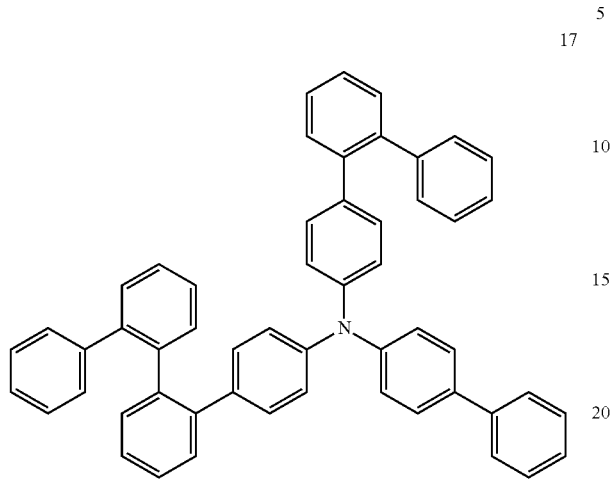
18
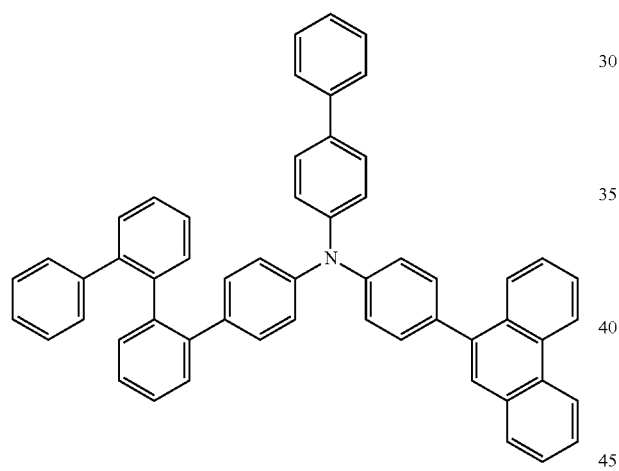
19
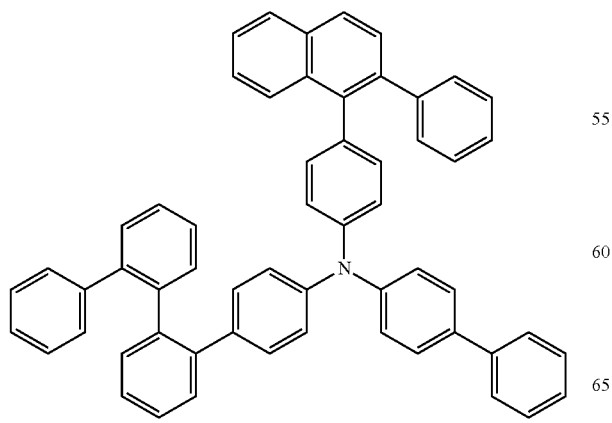
20
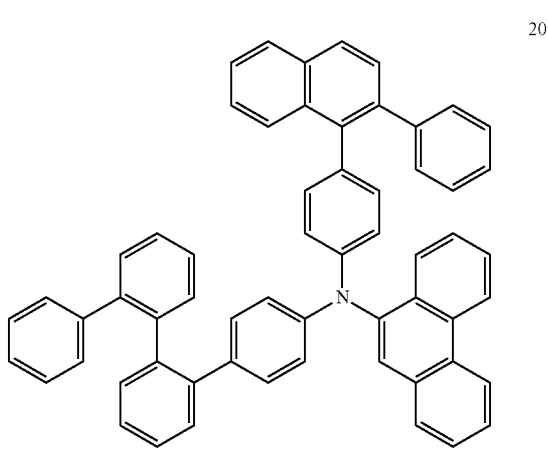
21
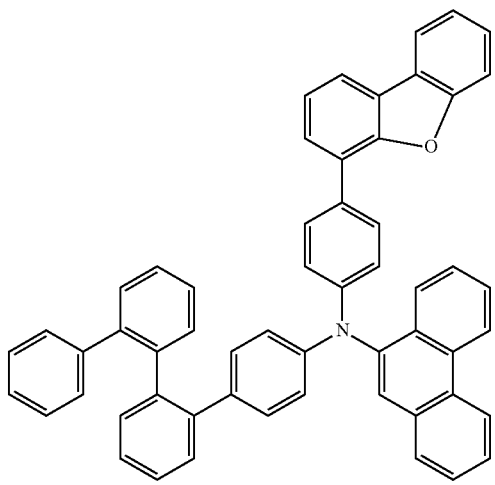
22
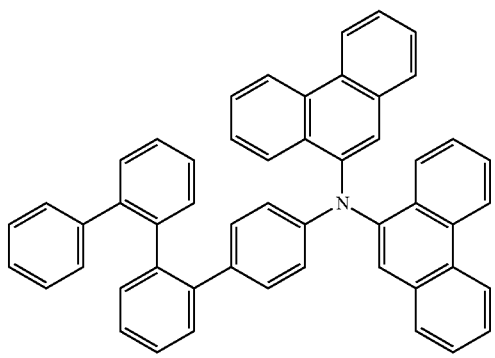

-continued

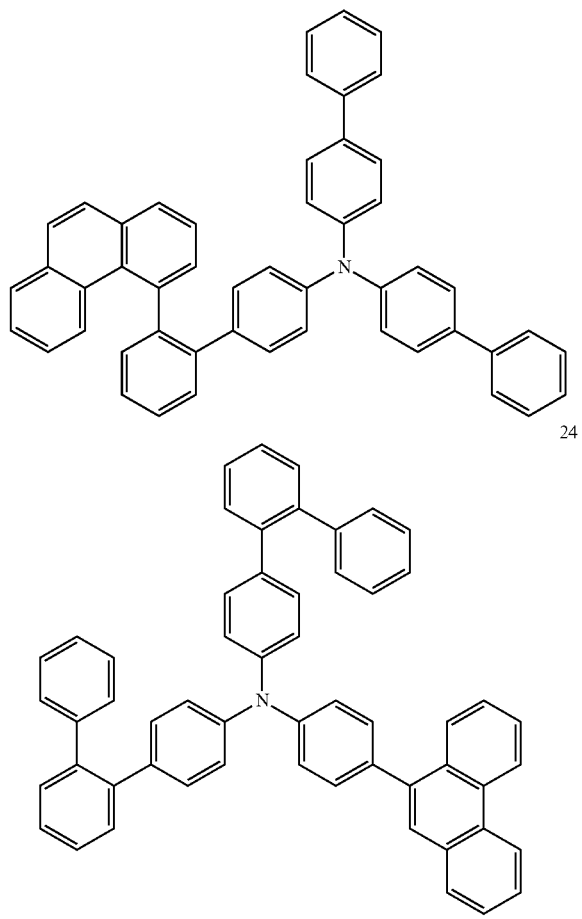

The above-described monoamine compound according to an embodiment may be used as a material for an organic electroluminescence device to help improve emission efficiency of the organic electroluminescence device. The monoamine compound according to an embodiment may have a high level of the lowest triplet excitation energy (T1). The monoamine compound according to an embodiment may have a high level of the lowest triplet excitation energy, and the diffusion of triplet excitons generated in the emission layer into the hole transport region may be inhibited, thereby improving emission efficiency of the organic electroluminescence device.

Hereinafter, an organic electroluminescence device according to an embodiment will be explained. The explanation on the above-described monoamine compound according to an embodiment will not be given further, and unexplained parts will follow the above-description on the monoamine compound according to an embodiment.

Figure 2:
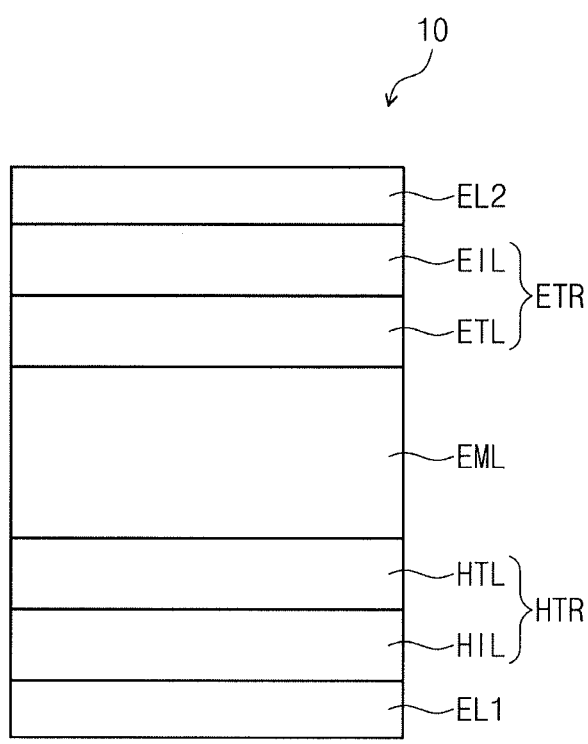
FIG. 2 illustrates a schematic cross-sectional view of an organic electroluminescence device according to an embodiment.

Each of FIGS. 1 and 2 illustrates a schematic cross-sectional view of an organic electroluminescence device according to an embodiment. Referring to FIGS. 1 and 2, an organic electroluminescence device 10 according to an embodiment may include a first electrode EL1, a hole transport region HTR, an emission layer EML, an electron transport region ETR, and a second electrode EL2, laminated in order. Comparing with FIG. 1, FIG. 2 shows a schematic cross-sectional view illustrating an organic electroluminescence device according to an embodiment, in which a hole transport region HTR includes a hole injection layer HIL and a hole transport layer HTL, and an electron transport layer ETR includes an electron injection layer EIL and an electron transport layer ETL.

The first electrode EL1 and the second electrode EL2 are disposed oppositely, and a plurality of organic layers may be disposed between the first electrode EL1 and the second electrode EL2. The plurality of organic layers may include a hole transport region HTR, an emission layer EML and an electron transport region ETR.

In an implementation, the organic electroluminescence device 10 according to an embodiment may include the monoamine compound in a hole transport region HTR.

The first electrode EL1 has conductivity. The first electrode EL1 may be formed by a metal alloy or a conductive compound. The first electrode EL1 may be an anode.

The first electrode EL1 may be a transmissive electrode, a transflective electrode, or a reflective electrode. In case the first electrode EL1 is the transmissive electrode, the first electrode EL1 may be made of a transparent metal oxide such as indium tin oxide (ITO), indium zinc oxide (IZO), zinc oxide (ZnO), indium tin zinc oxide (ITZO), etc. In case the first electrode EL1 is the transflective electrode or reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). Also, the first electrode EL1 may have a structure including a plurality of layers including a reflective layer or transflective layer formed using the above materials, and a transparent conductive layer formed using ITO, IZO, ZnO, ITZO, etc.

Hereinafter, a case where the above-described monoamine compound is included in the hole transport region HTR, will be explained. In an implementation, the monoamine compound according to an embodiment may be included in at least one layer of one or more organic layers disposed between the first electrode EL1 and the second electrode EL2. In an implementation, the monoamine compound according to an embodiment may be included in the emission layer EML.

The organic electroluminescence device 10 according to an embodiment may include the above-described monoamine compound in the hole transport region HTR. For example, the organic electroluminescence device 10 according to an embodiment may include the monoamine compound represented by the following Formula 1 in the hole transport region HTR:

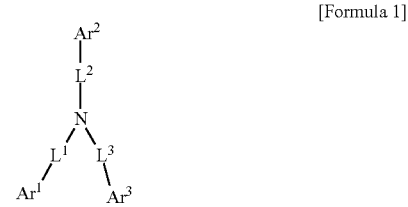

[Formula 1]

In Formula 1, $Ar^1$ may be, e.g., a group represented by the following Formula 2.

$Ar^2$ and $Ar^3$ may each independently be or include, e.g., a substituent represented by the following Formula 2, a hydrogen atom, a deuterium atom, a halogen atom, a cyano group, a substituted or unsubstituted silyl group, a substituted or unsubstituted aryl group having 6 to 30 ring carbon atoms, or a substituted or unsubstituted heteroaryl group having 2 to 30 ring carbon atoms.

$L^1$ to $L^3$ may each independently be or include, e.g., a direct linkage, a substituted or unsubstituted arylene group having 6 to 30 ring carbon atoms, or a substituted or unsubstituted heteroarylene group having 2 to 30 ring carbon atoms.

[Formula 2]

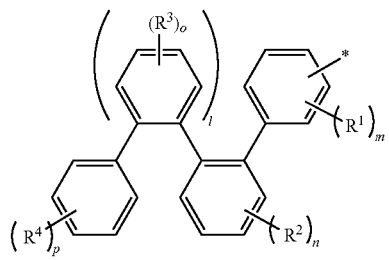

In Formula 2, $R^1$ to $R^4$ may each independently be or include, e.g., a hydrogen atom, a deuterium atom, a halogen atom, a cyano group, a substituted or unsubstituted silyl group, a substituted or unsubstituted alkyl group having 1 to 10 carbon atoms, a substituted or unsubstituted alkoxy group having 1 to 10 carbon atoms, a substituted or unsubstituted arylthio group having 1 to 10 carbon atoms, or a substituted or unsubstituted aryl group having 6 to 30 ring carbon atoms. In an implementation, $R^1$ to $R^4$ may be separate or may form a ring by combining adjacent groups with each other.

l may be 0 or 1, m, n and o may be each independently an integer of 0 to 4, and p may be an integer of 0 to 5.

In Formulae 1 and 2, particular explanation on the monoamine compound according to an embodiment of the inventive concept as described above may be applied to $Ar^1$ to $Ar^3$, $L^1$ to $L^3$, $R^1$ to $R^4$, and l to p.

The monoamine compound represented by Formula 1 may have a high level of the lowest triplet excitation energy (T1). For example, the monoamine compound represented by Formula 1 may have the lowest triplet excitation energy of about 3.2 eV or higher.

The hole transport region HTR is disposed on the first electrode EL1. The hole transport region HTR may include at least one of a hole injection layer HIL, a hole transport layer HTL, a hole buffer layer, or an electron blocking layer EBL. The thickness of the hole transport region HTR may be, for example, from about 1,000 Å to about 1,500 Å.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of a hole injection layer HIL or a hole transport layer HTL, or may have a single layer structure formed using a hole injection material and a hole transport material. In an implementation, the hole transport region HTR may have a single layer structure formed using a plurality of different materials, or a laminated structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, laminated in order from the first electrode EL1.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole transport region HTR may include the above-described monoamine compound according to an embodiment. The hole transport region HTR may include the above-described monoamine compound according to an embodiment as a hole transport material.

The layer including the above-described monoamine compound according to an embodiment may be a layer adjacent to the emission layer EML. As shown in FIG. 2, when the hole transport layer HTL in the hole transport region HTR is adjacent to the emission layer EML, the hole transport layer HTL may include the monoamine compound according to an embodiment.

The hole transport layer HTL may include one or more of the monoamine compound represented by Formula 1. The hole transport layer HTL may further include a suitable material in addition to the monoamine compound represented by Formula 1.

In case the hole transport layer HTL includes the monoamine compound, the hole injection layer HIL may include a suitable hole injection material. In an implementation, the suitable hole injection material included in the hole injection layer HIL may include, e.g., triphenylamine-containing polyether ketone (TPAPEK), 4-isopropyl-4'-methyldiphenyliodiumtetrakis(pentafluorophenyl)borate (PPBI), N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4"-tris(3-methylphenylphenylamino)triphenylamine (m-MTDATA), N,N'-di(1-naphthyl)-N,N'-diphenylbenzidine (NPB), 4,4',4"-tris(N,N-diphenylamino)triphenylamine (TDATA), 4,4',4"-tris {N,N'-2-naphthylphenylamino}-triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonic acid (PANI/CSA), polyaniline/poly(4-styrenesulfonate) (PANI/PSS), etc.

In an implementation, in case the hole transport layer HTL does not include the monoamine compound, and the emission layer EML includes the monoamine compound, the hole transport layer HTL may include, e.g., 1,1-bis[(di-4-tolylamino)phenyl]cyclohexane (TAPC), carbazole derivatives such as N-phenyl carbazole and polyvinyl carbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), N,N'-di(1-naphthyl)-N,N'-diphenylbenzidine (NPB), etc.

The thickness of the hole transport region HTR may be from about 100 Å to about 10,000 Å, for example, from about 100 Å to about 1,000 Å. In case the hole transport region HTR includes both of the hole injection layer HIL and the hole transport layer HTL, the thickness of the hole injection layer HIL may be from about 100 Å to about 10,000 Å, for example, from about 100 Å to about 1,000 Å, and the thickness of the hole transport layer HTL may be from about 30 Å to about 1,000 Å. In case the thicknesses of the hole transport region HTR, the hole injection layer HIL and the hole transport layer HTL satisfy the above-described ranges, satisfactory hole transport properties may be obtained without the substantial increase of a driving voltage.

The hole transport region HTR may further include a charge generating material in addition to the above-described materials to improve conductivity. The charge generating material may be dispersed in the hole transport region HTR uniformly or non-uniformly. The charge generating material may be, for example, a p-dopant. In an implementation, the p-dopant may be one of quinone derivatives, metal oxides, or cyano group-containing compounds. In an implementation, the p-dopant may include quinone derivatives such as tetracyanoquinodimethane (TCNQ) and 2,3,5,6-tetrafluoro-tetracyanoquinodimethane (F4-TCNQ), metal oxides such as tungsten oxide and molybdenum oxide.

The hole transport region HTR may further include at least one of the hole buffer layer or the electron blocking layer EBL in addition to the hole injection layer HIL and the hole transport layer HTL, as described above. The hole buffer layer may compensate an optical resonance distance according to the wavelength of light emitted from the emission layer EML and increase light emission efficiency. Materials included in the hole transport region HTR may be used as materials included in the hole buffer layer. The electron blocking layer EBL is a layer preventing electron injection from the electron transport region ETR into the hole transport region HTR.

In an implementation, the hole transport region HTR may include the hole injection layer HIL, the hole transport layer HTL and the electron blocking layer EBL. In an implementation, the monoamine compound represented by Formula 1 may be included in the hole transport layer HTL.

The hole transport region HTR of the organic electroluminescence device 10 according to an embodiment may include one or more of the monoamine compound represented by Formula 1. For example, the organic electroluminescence device 10 according to an embodiment may include a compound of the following Compound Group 1 in the hole transport region HTR.

[Compound Group 1]

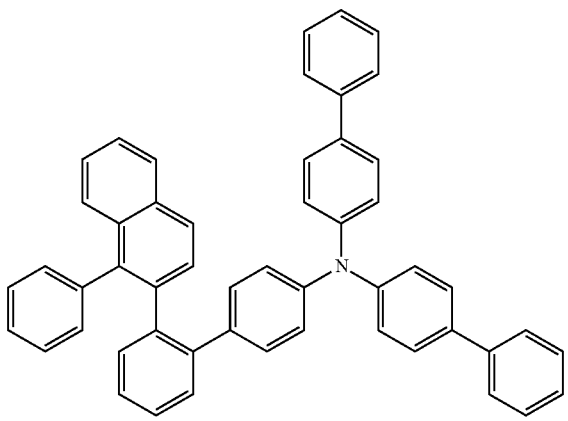

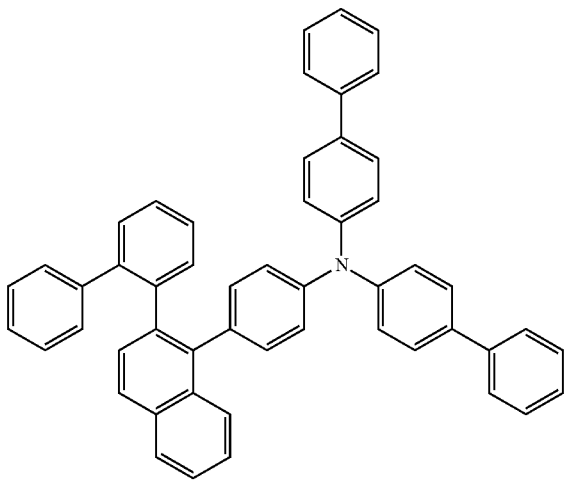

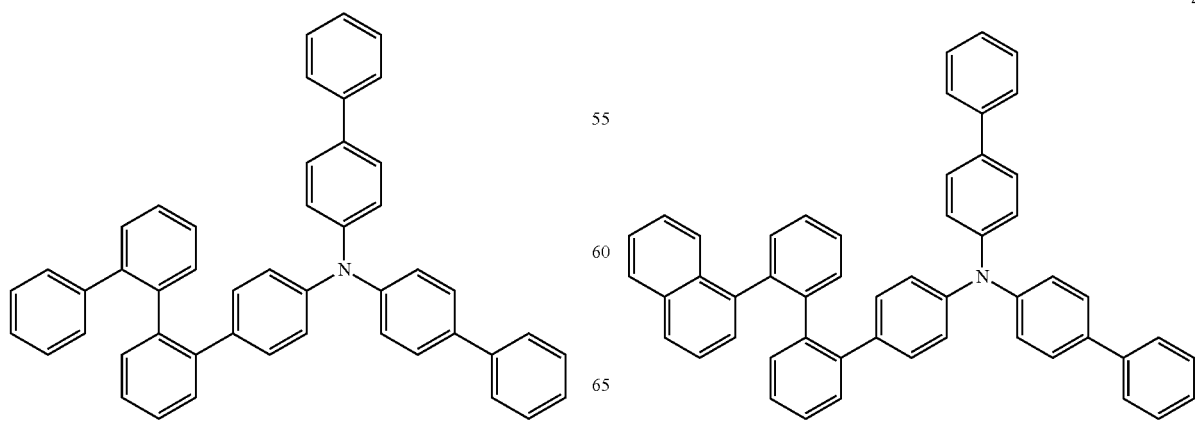

5
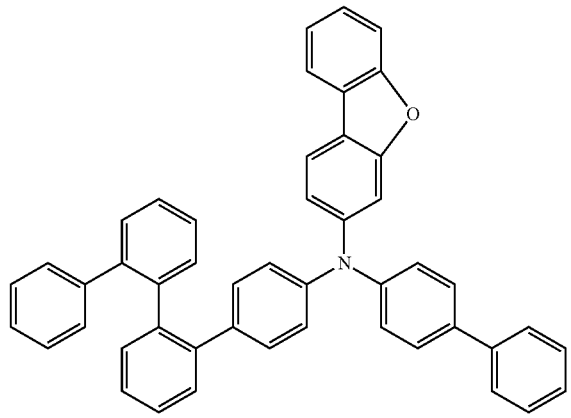
6
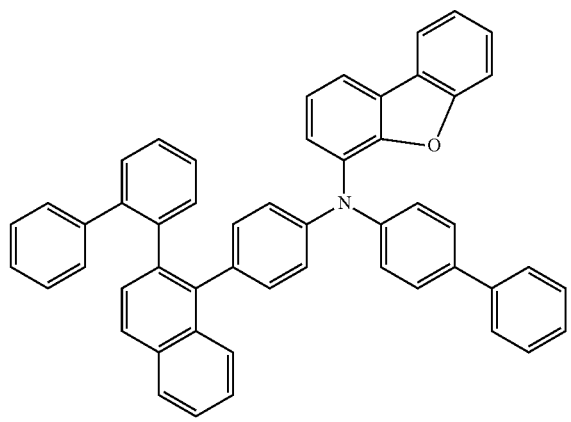
7
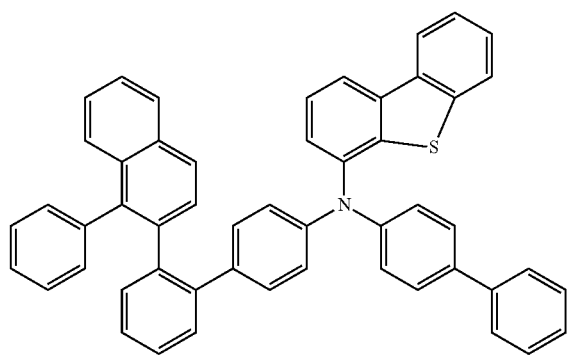
8
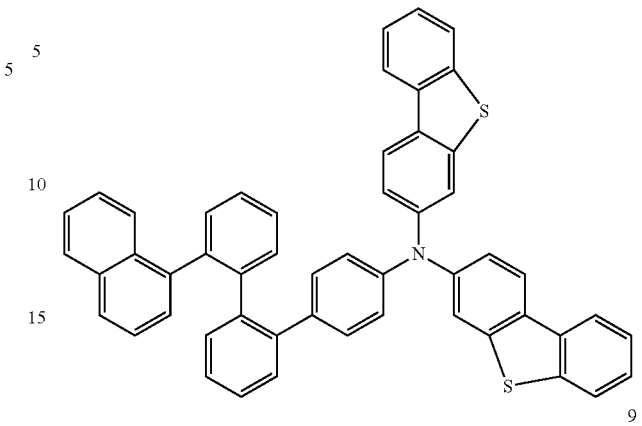
9
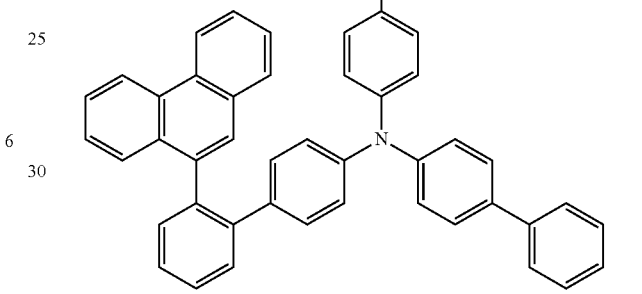
10
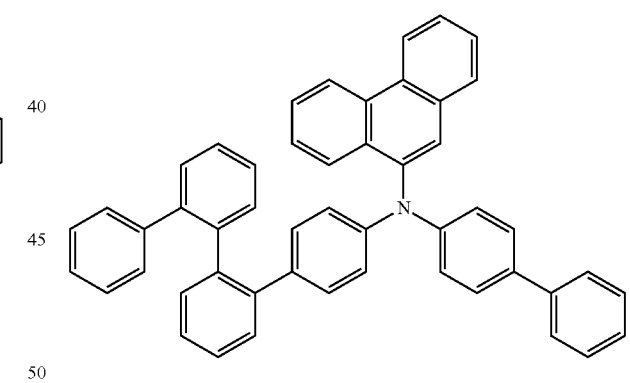
11
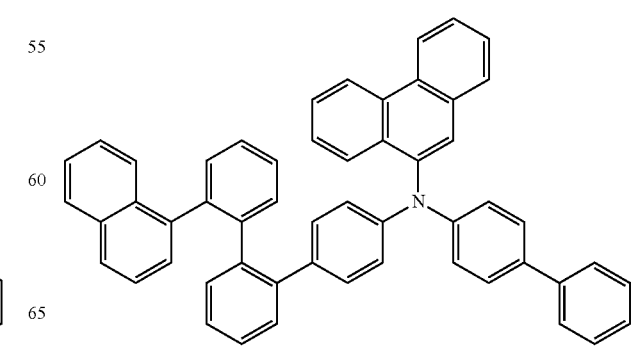

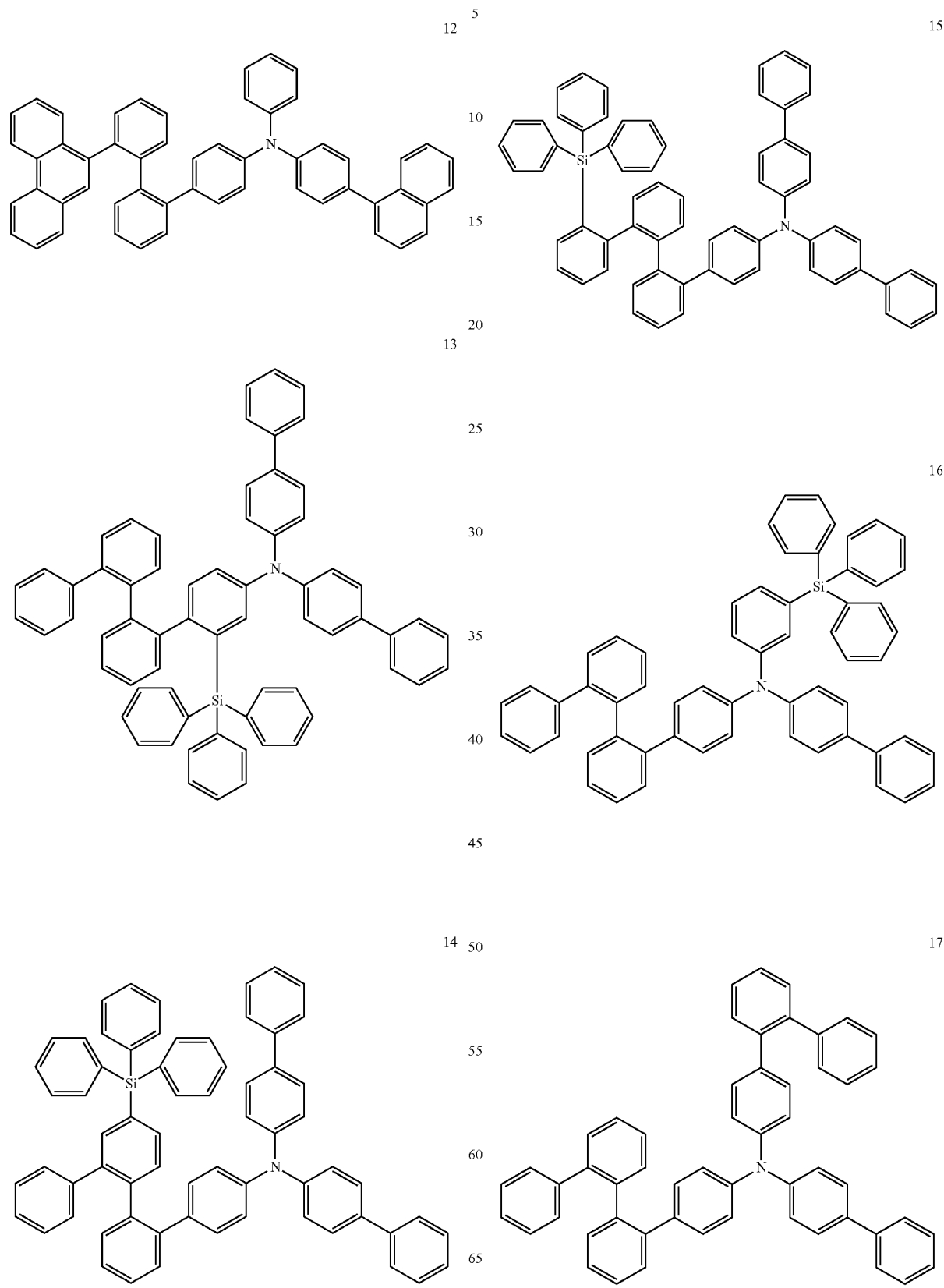

18
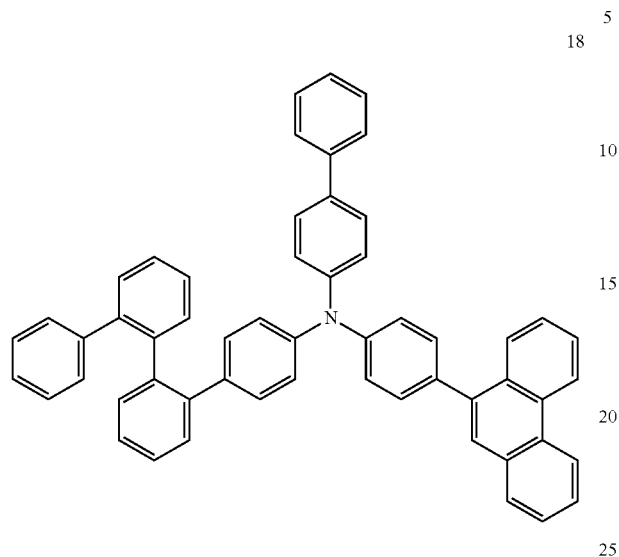
19
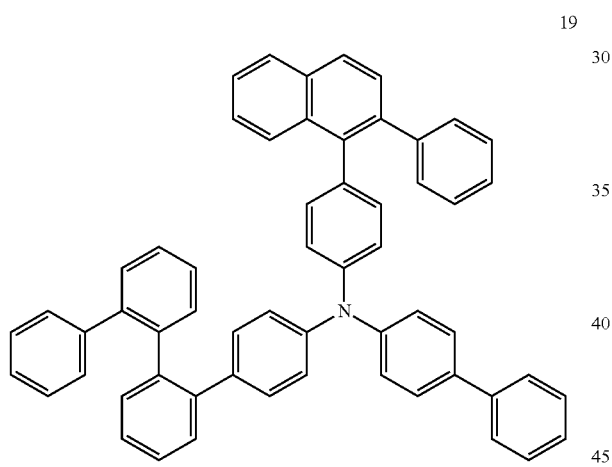
20
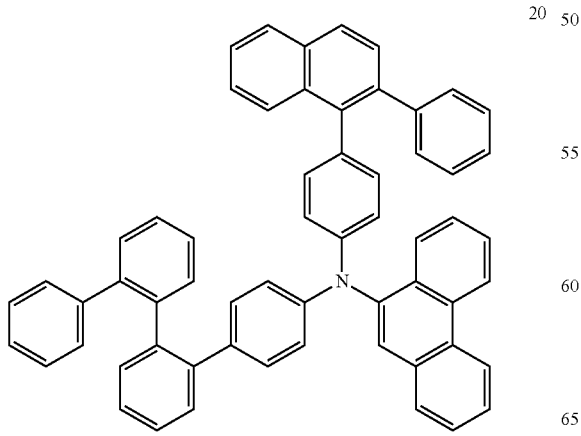
21
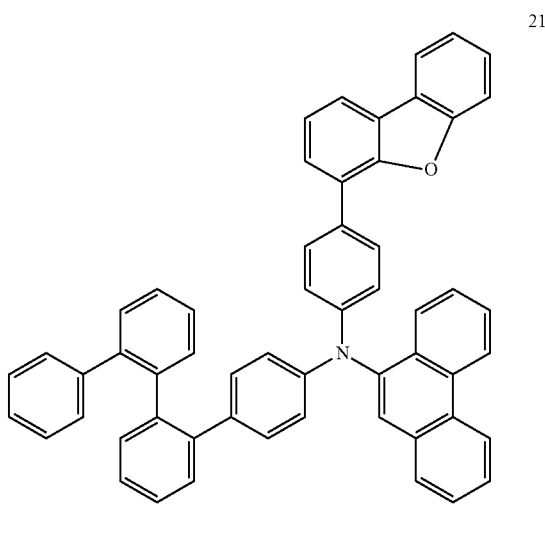
22
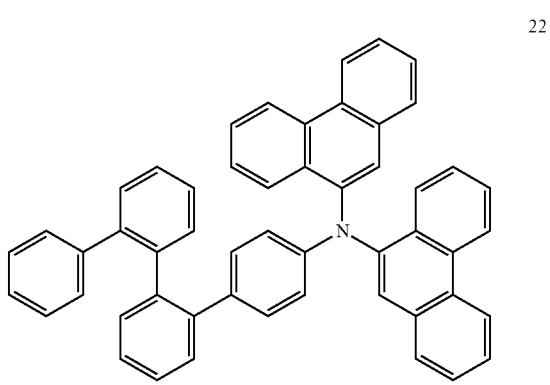
23
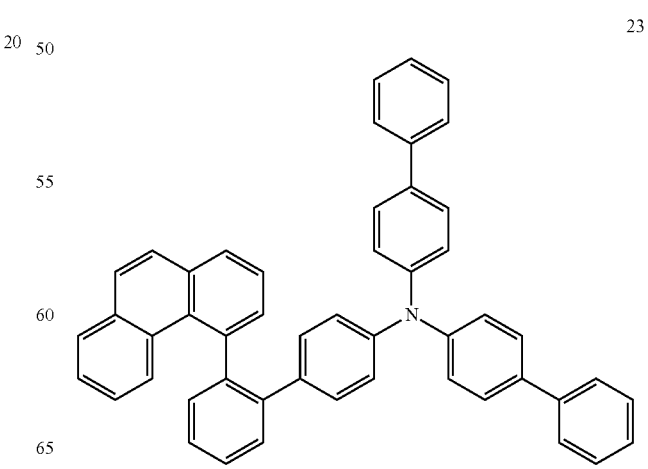

-continued

24

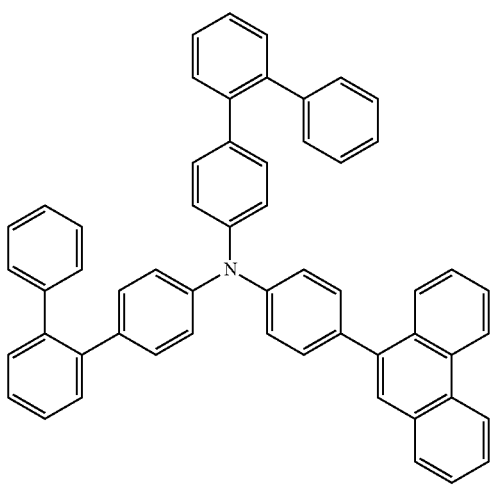

The organic electroluminescence device 10 according to an embodiment may have improved emission efficiency by including the monoamine compounds represented by Formula 1 in the hole transport region HTR. Furthermore, the organic electroluminescence device 10 according to an embodiment may have improved external quantum efficiency by including the monoamine compounds represented by Formula 1 in the hole transport region HTR.

The emission layer EML is disposed on the hole transport region HTR. The thickness of the emission layer EML may be, for example, from about 100 Å to about 600 Å. The emission layer EML may have a single layer formed using a single material, a single layer formed using a plurality of different materials, or a multilayer structure having a plurality of layers formed using a plurality of different materials.

The emission layer EML may emit one of red light, green light, blue light, white light, yellow light, or cyan light. For example, the emission layer EML of the organic electroluminescence device according to an embodiment may emit blue light.

The emission layer EML may include a fluorescent material or a phosphorescent material. The emission layer EML may include a host and a dopant.

The emission layer EML may include a host. The host may be a suitable material, e.g., tris(8-hydroxyquinolino) aluminum (Alq3), 4,4'-bis(N-carbazolyl)-1,1'-biphenyl (CBP), poly(N-vinylcarbazole) (PVK), 9,10-di(naphthalen-2-yl)anthracene (ADN), 4,4',4''-tris(carbazol-9-yl)-triphenylamine (TCTA), 1,3,5-tris(N-phenylbenzimidazol-2-yl) benzene (TPBi), 3-tert-butyl-9,10-di(naphth-2-yl) anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis(triphenylsilyl)benzene (UGH2), hexaphenylcyclotrisiloxane (DPSiO$_3$), octaphenylcyclotetrasiloxane (DPSiO$_4$), 2,8-bis(diphenylphosphoryl)dibenzofuran (PPF), etc.

The dopant may include, e.g., styryl derivatives (for example, 1,4-bis[2-(3-N-ethylcarbazolyl)vinyl]benzene (BCzVB), 4-(di-p-tolylamino)-4'-[(di-p-tolylamino)styryl] stilbene (DPAVB), N-(4-((E)-2-(6-((E)-4-(diphenylamino) styryl)naphthalen-2-yl)vinyl)phenyl)-N-phenylbenzenamine (N-BDAVBi)), perylene and the derivatives thereof (for example, 2,5,8,11-tetra-t-butylperylene (TBP)), pyrene and the derivatives thereof (for example, 1,1-dipyrene, 1,4-dipyrenylbenzene, 1,4-bis(N,N-diphenylamino)pyrene), etc.

When the emission layer EML emits red light, the emission layer EML may further include, e.g., tris(dibenzoylmethanato)phenanthroline europium (PBD:Eu(DBM)$_3$ (Phen)), or a fluorescent material including perylene. In case the emission layer EML emits red light, the dopant included in the emission layer EML may be selected from, for example, a metal complex or an organometallic complex such as bis(1-phenylisoquinoline)acetylacetonate iridium (PIQIr(acac)), bis(1-phenylquinoline)acetylacetonate iridium (PQIr(acac), tris(1-phenylquinoline)iridium (PQIr), and octaethylporphyrin platinum (PtOEP), rubrene and the derivatives thereof, and 4-dicyanomethylene-2-(p-dimethylaminostyryl)-6-methyl-4H-pyran (DCM) and the derivatives thereof.

When the emission layer EML emits green light, the emission layer EML may further include a fluorescent material including, e.g., tris(8-hydroxyquinolino)aluminum (Alq3). In case the emission layer EML emits green light, the dopant included in the emission layer EML may be selected from, e.g., a metal complex or an organometallic complex such as fac-tris(2-phenylpyridine)iridium (Ir(ppy)$_3$), and coumarin and the derivatives thereof.

When the emission layer EML emits blue light, the emission layer EML may further include a fluorescent material including any one selected from the group consisting of, for example, spiro-DPVBi, spiro-6P, distyryl-benzene (DSB), distyrylarylene (DSA), a polyfluorene (PFO)-based polymer, and a poly(p-phenylene vinylene) (PPV)-based polymer. In case the emission layer EML emits blue light, the dopant included in the emission layer EML may be selected from a metal complex or an organometallic complexes such as (4,6-F$_2$ppy)$_2$Irpic, perylene and the derivatives thereof.

The electron transport region ETR is disposed on the emission layer EML. In an implementation, the electron transport region ETR may include at least one of a hole blocking layer, an electron transport layer ETL or an electron injection layer EIL.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of the electron injection layer EIL or the electron transport layer ETL, or a single layer structure formed using an electron injection material and an electron transport material. In an implementation, the electron transport region ETR may have a single layer structure having a plurality of different materials, or a laminated structure of electron transport layer ETL/electron injection layer EIL, or hole blocking layer/electron transport layer ETL/electron injection layer EIL, laminated in order from the emission layer EML. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

In case the electron transport region ETR includes the electron transport layer ETL, the electron transport region ETR may include a suitable material. In an implementation, the electron transport region ETR may include, e.g., tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate (Bebq2), 9,10-di(naphthalen-2-yl)anthracene (ADN), or a mixture thereof.

When the electron transport region ETR includes the electron transport layer ETL, the thickness of the electron transport layer ETL may be from about 100 Å to about 1,000 Å, for example, from about 150 Å to about 500 Å. If the thickness of the electron transport layer ETL satisfies the above-described range, satisfactory electron transport properties may be obtained without substantial increase of a driving voltage.

When the electron transport region ETR includes the electron injection layer EIL, it may include a suitable material. In an implementation, the electron transport region ETR may include, e.g., LiF, lithium quinolate (Liq), $Li_2O$, BaO, NaCl, CsF, a metal in lanthanides such as Yb, or a metal halide such as RbCl and RbI. The electron injection layer EIL also may be formed using a mixture material of an electron transport material and an insulating organo metal salt. The organo metal salt may be a material having an energy band gap of about 4 eV or more. In an implementation, the organo metal salt may include, e.g., a metal acetate, a metal benzoate, a metal acetoacetate, a metal acetylacetonate, or a metal stearate.

When the electron transport region ETR includes the electron injection layer EIL, the thickness of the electron injection layer EIL may be from about 1 Å to about 100 Å, for example, from about 3 Å to about 90 Å. In case the thickness of the electron injection layer EIL satisfies the above described range, satisfactory electron injection properties may be obtained without inducing the substantial increase of a driving voltage.

The electron transport region ETR may include a hole blocking layer, as described above. In an implementation, the hole blocking layer may include, e.g., at least one of 2,9-dimethyl-4,7-diphenyl-1,10-phenanthroline (BCP) or 4,7-diphenyl-1,10-phenanthroline (Bphen).

The second electrode EL2 is disposed on the electron transport region ETR. The second electrode EL2 has conductivity. The second electrode EL2 may be formed using a metal alloy or a conductive compound. The second electrode EL2 may be a cathode. The second electrode EL2 may be a transmissive electrode, a transflective electrode or a reflective electrode. In case the second electrode EL2 is the transmissive electrode, the second electrode EL2 may be formed using transparent metal oxides, for example, ITO, IZO, ZnO, ITZO, etc.

In case the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

In an implementation, the second electrode EL2 may be connected with an auxiliary electrode. In case the second electrode EL2 is connected with the auxiliary electrode, the resistance of the second electrode EL2 may decrease.

In the organic electroluminescence device 10, according to the application of a voltage to each of the first electrode EL1 and the second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to generate excitons, and light may be emitted via the transition of the excitons from an excited state to a ground state.

In case the organic electroluminescence device 10 is a top emission type, the first electrode EL1 may be a reflective electrode, and the second electrode EL2 may be a transmissive electrode or a transflective electrode. In case the organic electroluminescence device 10 is a bottom emission type, the first electrode EL1 may be a transmissive electrode or a transflective electrode, and the second electrode EL2 may be a reflective electrode.

The organic electroluminescence device according to an embodiment may include the above-described monoamine compound, thereby securing improved emission efficiency. Furthermore, in the organic electroluminescence device according to an embodiment including the above-described monoamine compound having a high level of the lowest triplet energy in the hole transport region, the diffusion of triplet excitons generated in the emission layer may be inhibited, thereby attaining high external quantum efficiency.

In an implementation, the organic electroluminescence device according to an embodiment may be a blue light emitting device, a green light emitting device, a red light emitting device or a white light emitting device. In an implementation, the organic electroluminescence device according to an embodiment may have high emission efficiency, when it is a blue light emitting device.

Hereinafter, the monoamine compound according to an embodiment and the organic electroluminescence device including the same will be explained in more detail with reference to Examples and Comparative Examples.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

1. Synthesis of Monoamine Compound

The synthetic method of the monoamine compound according to an embodiment concept will be explained in more detail by illustrating the synthetic method of Compounds 1, 5, and 10 of Compound Group 1. The following synthetic methods of the monoamine compounds are exemplary embodiments.

(Synthesis of Compound 1)

Compound 1, an monoamine compound according to an embodiment, may be synthesized, e.g., by an amination reaction using quaterphenyl and aryl bromide as shown in the following Reaction Scheme 1.

Under an argon atmosphere, xylene (150 mL) was added to Compound A (5.68 g, 17.8 mmol), Compound B (8.24 g, 35.4 mmol), tris(dibenzilidenacetone)dipalladium (810 mg, 0.884 mmol), tris(tert-butyl)phosphine (1.6 M solution, 1.11 mL, 1.77 mmol), and sodium-tert-butoxide (8.05 g, 88.4 mmol), and the mixture was heated to reflux at about 130° C. for about 8 hours. After cooling to ambient temperature, precipitated solid was filtered. The precipitated solid was purified by column chromatography (toluene:hexane 1:1)

and recrystallized with toluene/ethanol to obtain Compound 1 (9.18 g, 14.7 mmol, yield 83%). The structure of product was identified using FAB-MS (m/z=625).

[Reaction Scheme 1]

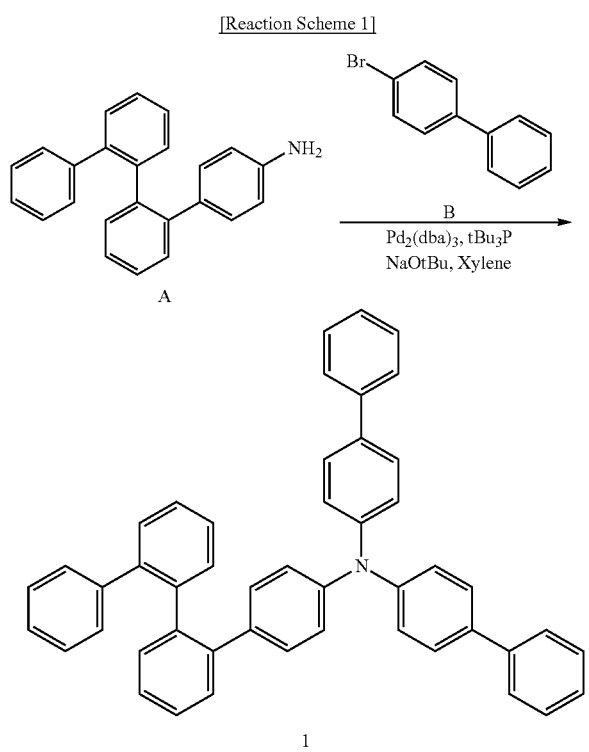

(Synthesis of Compound 5)

Compound 5, a monoamine compound according to an embodiment, may be synthesized, e.g., by an amination reaction as shown in the following Reaction Scheme 2.

Under an argon atmosphere, xylene (150 mL) was added to Compound A (13.5 g, 42.0 mmol), Compound B (9.79 g, 42.0 mmol), tris(dibenzilidenacetone)dipalladium (1.92 g, 2.10 mmol), tris(tert-butyl)phosphine (1.6 M solution, 2.63 mL, 4.20 mmol), and sodium-tert-butoxide (4.04 g, 42.0 mmol), and the mixture was heated to reflux at about 130° C. for about 4 hours. After cooling to ambient temperature, precipitated solid was filtered. The precipitated solid was purified by column chromatography (toluene:hexane 1:1) and recrystallized with toluene/ethanol to obtain Intermediate Compound C (16.9 g, 35.7 mmol, yield 85%).

Next, under an argon atmosphere, xylene (150 mL) was added to Intermediate Compound C (6.78 g, 14.3 mmol), Compound D (3.54 g, 14.3 mmol), tris(dibenzilidenacetone)dipalladium (655 mg, 0.716 mmol), tris(tert-butyl)phosphine (1.6 M solution, 0.895 mL, 1.43 mmol), and sodium-tert-butoxide (4.04 g, 42.0 mmol), and the mixture was heated to reflux at about 130° C. for about 6 hours. After cooling to ambient temperature, precipitated solid was filtered. The precipitated solid was purified by column chromatography (toluene:hexane 1:1) and recrystallized with toluene/ethanol to obtain Compound 5 (7.14 g, 11.2 mmol, yield 78%). The structure of product was identified using FAB-MS (m/z=639).

[Reaction Scheme 2]

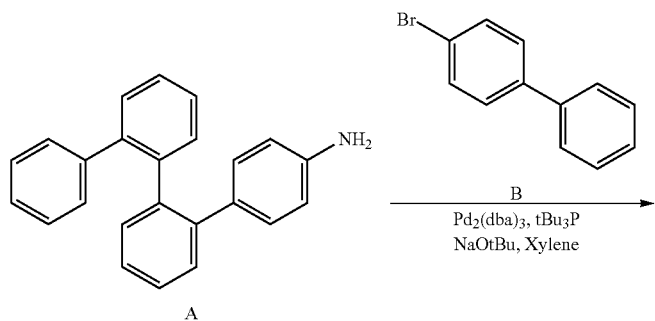

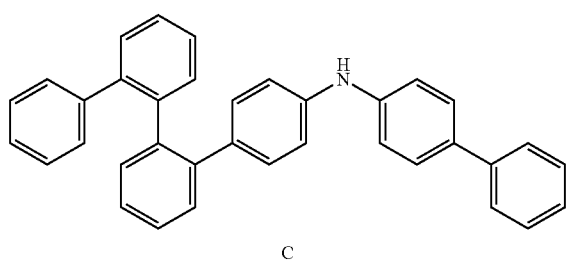

-continued

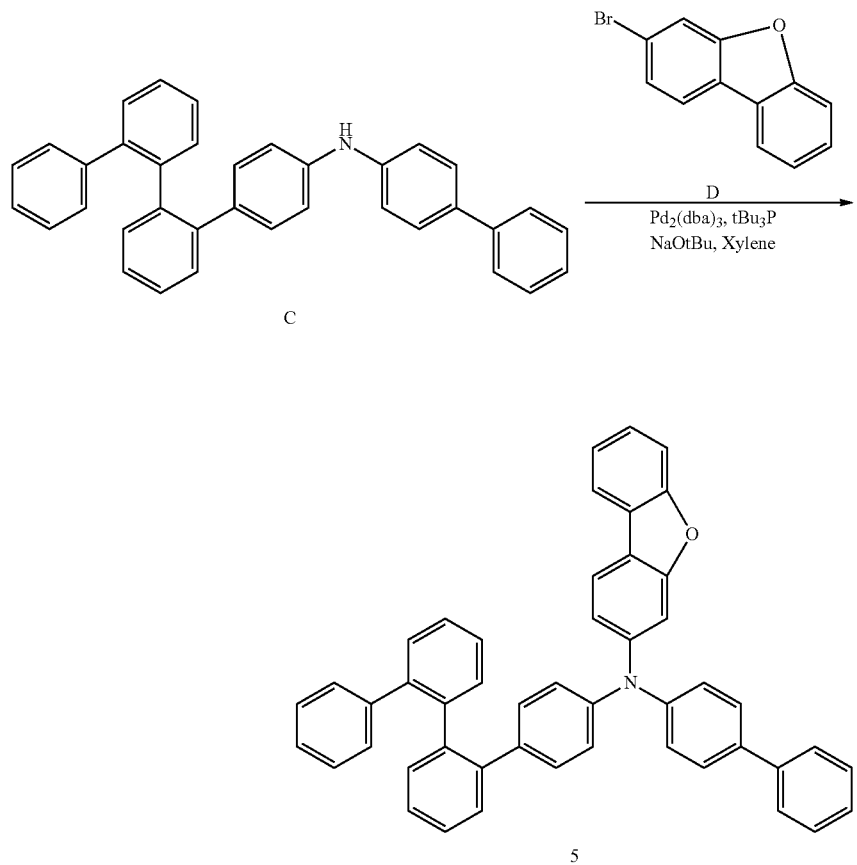

(Synthesis of Compound 10)

Compound 10, a monoamine compound according to an embodiment, may be synthesized, e.g., as shown in the following Reaction Scheme 3.

Under an argon atmosphere, xylene (150 mL) was added to Intermediate Compound C (8.44 g, 17.8 mmol), Compound E (4.58 g, 17.8 mmol), tris(dibenzilidenacetone) dipalladium (815 mg, 0.891 mmol), tris(tert-butyl)phosphine (1.6 M solution, 1.13 mL, 1.78 mmol), and sodium-tert-butoxide (5.13 g, 53.4 mmol), and the mixture was heated to reflux at about 130° C. for about 8 hours. After cooling to ambient temperature, precipitated solid was filtered. The precipitated solid was purified by column chromatography (toluene:hexane 1:1) and recrystallized with toluene/ethanol to obtain Compound 10 (8.33 g, 12.8 mmol, yield 72%). The structure of product was identified using FAB-MS (m/z=649).

[Reaction Scheme 3]

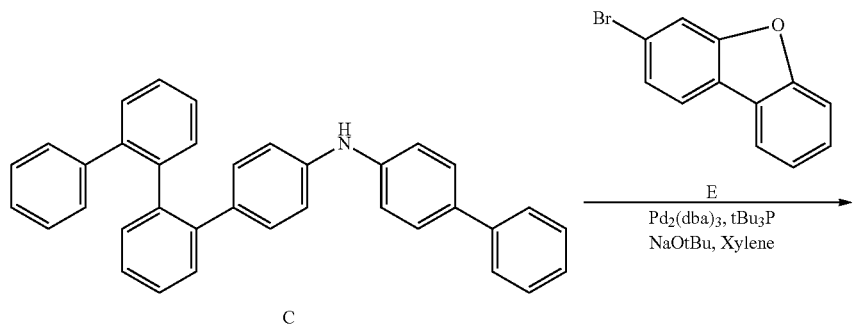

-continued

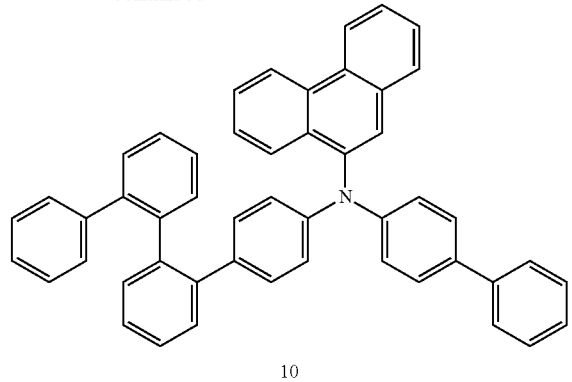

10

2. Manufacturing of Organic Electroluminescence Devices Including Monoamine Compounds and Evaluation Thereof (Manufacturing of Organic Electroluminescence Devices)

Organic electroluminescence devices including the monoamine compounds in the hole transport layer were manufactured by the following method. The organic electroluminescence devices of Examples 1 to 3 were manufactured by using Compounds 1, 5, and 10 as a hole transport material. The organic electroluminescence devices of Comparative Examples 1 to 5 were manufactured by using the following Comparative Compounds C1 to C5 as a hole transport material.

Table 1 shows the compounds used in the hole transport layer for Examples 1 to 3 and Comparative Examples 1 to 5.

TABLE 1

Compound 1　　　　　　　　　　　　　　　　　　1

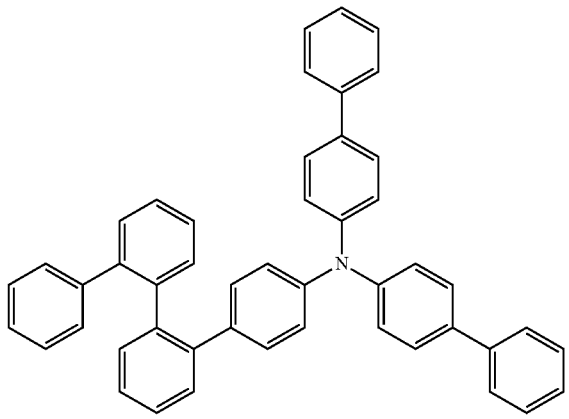 [SMILES: c1ccc(-c2ccc(N(c3ccc(-c4ccccc4)cc3)c3ccc(-c4ccccc4-c4ccccc4-c4ccccc4)cc3)cc2)cc1]

Compound 5　　　　　　　　　　　　　　　　　　5

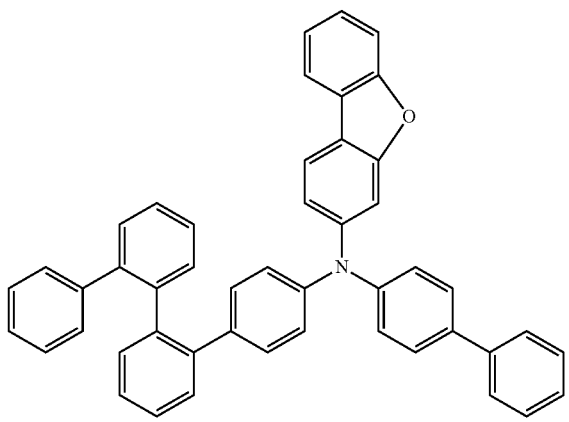 [SMILES: c1ccc(-c2ccc(N(c3ccc(-c4ccccc4-c4ccccc4-c4ccccc4)cc3)c3ccc4c(c3)oc3ccccc34)cc2)cc1]

TABLE 1-continued
| Compound 10 | 10 |
|---|---|
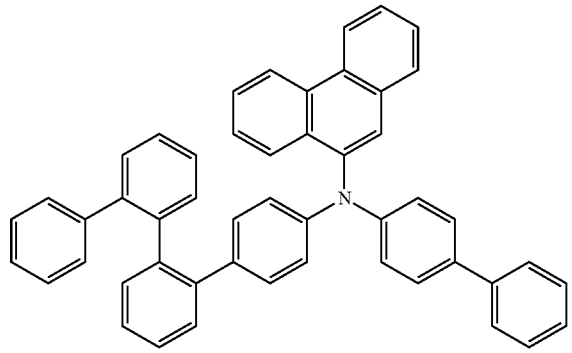 [SMILES: c1ccc(-c2ccc(N(c3ccc(-c4ccccc4-c4ccccc4-c4ccccc4)cc3)c3cc4ccccc4c4ccccc34)cc2)cc1]
| Comparative Compound c1 | c1 |
|---|---|
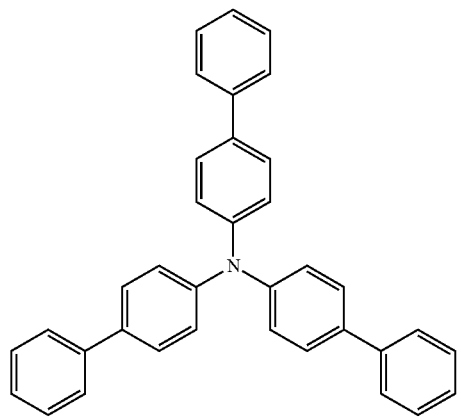 [SMILES: c1ccc(-c2ccc(N(c3ccc(-c4ccccc4)cc3)c3ccc(-c4ccccc4)cc3)cc2)cc1]
| Comparative Compound c2 | c2 |
|---|---|
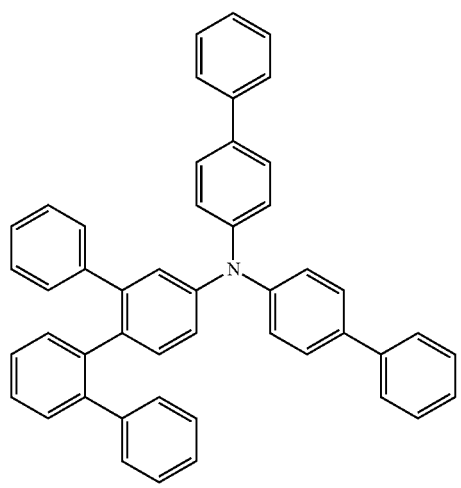 [SMILES: c1ccc(-c2ccc(N(c3ccc(-c4ccccc4)cc3)c3ccc(-c4ccccc4-c4ccccc4)c(-c4ccccc4)c3)cc2)cc1]

TABLE 1-continued

| Comparative Compound c3 | 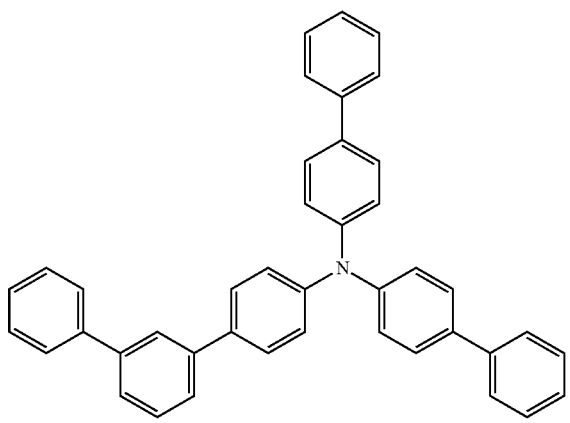 [SMILES: c1ccc(-c2ccc(N(c3ccc(-c4ccccc4)cc3)c3ccc(-c4cccc(-c5ccccc5)c4)cc3)cc2)cc1] | c3 |
| Comparative Compound c4 | 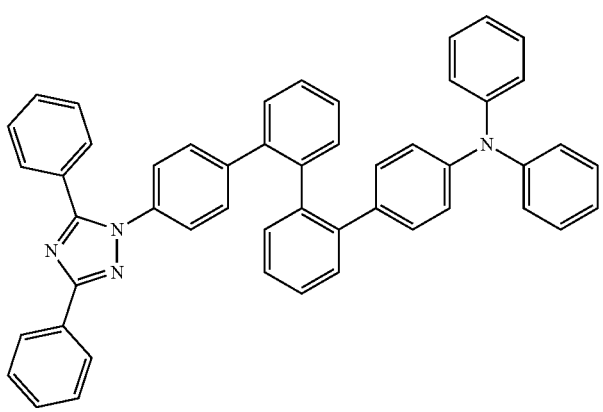 [SMILES: c1ccc(-c2nc(-c3ccccc3)n(-c3ccc(-c4ccccc4-c4ccccc4-c4ccc(N(c5ccccc5)c5ccccc5)cc4)cc3)n2)cc1] | c4 |
| Comparative Compound c5 | 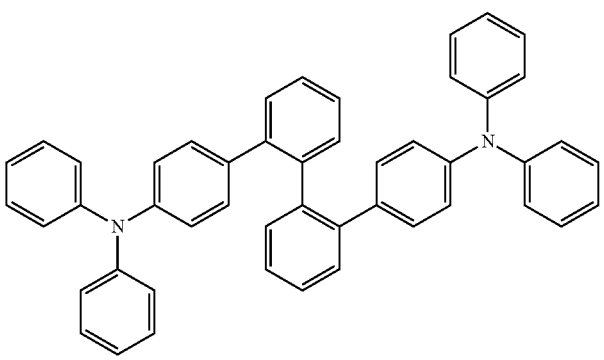 [SMILES: c1ccc(N(c2ccccc2)c2ccc(-c3ccccc3-c3ccccc3-c3ccc(N(c4ccccc4)c4ccccc4)cc3)cc2)cc1] | c5 |

Organic electroluminescence devices of the Examples and Comparative Examples were manufactured by the following method.

ITO was patterned on a glass substrate to a thickness of about 1,500 Å, followed by washing with ultrapure water and performing UV ozone treatment for about 10 minutes. After that, a hole injection layer was formed using 4,4',4"-tris[2-naphthyl(phenyl)amino]triphenylamine (TNATA) to a thickness of about 600 Å, and then a hole transport layer HTL was formed using the Example Compounds and Comparative Compounds to a thickness of about 300 Å.

Next, an emission layer was formed using 9,10-di(naphthalen-2-yl)anthracene (ADN) doped with 3% 2,5,8,11-tetra-t-butylperylene (TBP) to a thickness of about 250 Å.

An electron transport layer was formed using tris(8-hydroxyquinolino)aluminum (Alq3) to a thickness of about 250 Å, and an electron injection layer was formed using LiF to a thickness of about 10 Å. A second electrode was formed using Al to a thickness of about 1,000 Å.

In the Examples and Comparative Examples, the hole injection layer, hole transport layer, emission layer, electron transport layer, electron injection layer and second electrode were formed by using a vacuum deposition apparatus.

(Property Evaluation of Organic Electroluminescence Devices)

Emission efficiency and a half-life at a current density of 10 mA/cm$^2$ were measured to evaluate the properties of the organic electroluminescence devices manufactured in the Examples and Comparative Examples. The voltage and current density of organic electroluminescence devices were measured by using a source meter (Keithley Instruments, 2400 series). The half-life indicates a brightness half time from initial brightness of 1,000 cd/m$^2$.

Property evaluation results of the organic electroluminescence devices are shown in Table 2 below. In Table 2, emission efficiency and life are relative values based on those of Comparative Example 3 (100%)

TABLE 2

| Examples | Hole transport layer | Emission efficiency (%) | Life (%) |
|---|---|---|---|
| Example 1 | Compound 1 | 116 | 125 |
| Example 2 | Compound 5 | 112 | 132 |
| Example 3 | Compound 10 | 118 | 120 |
| Comparative Example 1 | Comparative Compound C1 | 80 | 101 |
| Comparative Example 2 | Comparative Compound C2 | 110 | 88 |
| Comparative Example 3 | Comparative Compound C3 | 100 | 100 |
| Comparative Example 4 | Comparative Compound C4 | 58 | 35 |
| Comparative Example 5 | Comparative Compound C5 | 75 | 65 |

Referring to the results in Table 2, it may be seen that the organic electroluminescence devices of Examples 1 to 3 had enhanced emission efficiency, when compared with those of Comparative Examples 1 to 5.

Furthermore, it may be seen that the organic electroluminescence device of Comparative Example 1 had emission efficiency lower than that of Comparative Example 3, which confirms that emission efficiency decreases with a decrease in the number of aromatic rings. It may also be seen that the organic electroluminescence device of Comparative Example 2 had emission efficiency higher than that of Comparative Example 3, which confirms that an increase of the number of aromatic rings increases emission efficiency while decreasing the device life. For example, an increase of the number of aromatic rings may increase emission efficiency due to the enhanced steric effect in the vicinity of nitrogen, while decreasing the device life resulting from the decreased stability of substituents caused by the position of substituted aromatic rings and the consequential distortion of whole substituents. Accordingly, it may be seen that change of charge balance due to steric effect results in change of device life.

Meanwhile, it may be seen that use of diamine compounds (as in Comparative Examples 4 and 5) decreased device life and emission efficiency. Accordingly, it may be seen that change of the number of nitrogen in molecule results in a great change of energy level for charge transport, and that diamine compounds may not be suitable for materials of a hole transport layer adjacent to an emission layer.

According to the above results, it may be seen that the organic electroluminescence device including the monoamine compound according to an embodiment in the hole transport region may attain high emission efficiency as well as a long life.

By way of summation and review, in an application of an organic electroluminescence device to a display, a driving voltage may be decreased, emission efficiency may be increased, and life for the organic electroluminescence device may be extended, and development of materials which may stably implement these features in the organic electroluminescence device may be considered.

The monoamine compound according to an embodiment may improve emission efficiency and life of an organic electroluminescence device.

The organic electroluminescence device according to an embodiment may attain high efficiency by including the monoamine compound according to an embodiment in an organic layer, e.g., in a hole transport region.

The embodiments may provide a monoamine compound for an organic electroluminescence device with high efficiency.

The embodiments may provide an organic electroluminescence device with high efficiency and long life including a monoamine compound in an organic layer.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and, details may be made without departing from the spirit and scope of the present invention as set forth in the following claims.

What is claimed is:

1. A monoamine compound represented by the following Formula 1:

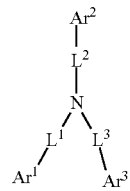

[Formula 1]

wherein, in Formula 1,

Ar$^1$ is a group represented by the following Formula 2,

Ar$^2$ and Ar$^3$ are each independently a group represented by the following Formula 2, a deuterium atom, a halogen atom, a cyano group, a substituted or unsubstituted silyl group, a substituted or unsubstituted aryl group having 6 to 30 ring carbon atoms, or a substituted or unsubstituted heteroaryl group having 2 to 30 ring carbon atoms, L$^1$ to L$^3$ are each independently a direct linkage, a substituted or unsubstituted arylene group having 6 to 30 ring carbon atoms, or a substituted or unsubstituted heteroarylene group having 2 to 30 ring carbon atoms,

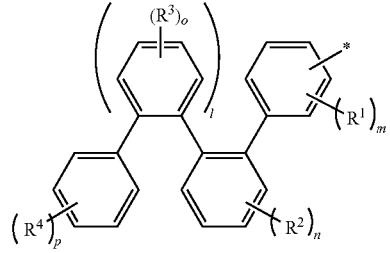

[Formula 2]

wherein, in Formula 2,

R$^1$ to R$^4$ are each independently a hydrogen atom, a deuterium atom, a halogen atom, a cyano group, a substituted or unsubstituted silyl group, a substituted or unsubstituted alkyl group having 1 to 10 carbon atoms, a substituted or unsubstituted alkoxy group having 1 to 10 carbon atoms, a substituted or unsubstituted arylthio group having 1 to 10 carbon atoms, or a substituted or unsubstituted aryl group having 6 to 30 ring carbon atoms, R$^1$ to R$^4$ are separate or form a ring by combining adjacent groups with each other, l is 0 or 1, m, n, and o are each independently an integer of 0 to 4, and p is an integer of 0 to 5, wherein at least one selected from Ar$^1$, Ar$^2$ and Ar$^3$ is different from at least an other one selected from Ar$^1$, Ar$^2$ and Ar$^3$, and wherein when L$^1$ to L$^3$ are each independently a direct linkage, and one selected from Ar$^2$ and Ar$^3$ is a group represented by Ar-18, an other one selected from Ar$^2$ and Ar$^3$ is a deuterium atom, a halogen atom, a cyano group, a substituted or unsubstituted silyl group, a substituted or unsubstituted aryl group derived from an aromatic hydrocarbon ring having 6 to 30 ring carbon atoms, or the group represented by Ar-18,

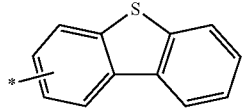

Ar-18 wherein in Ar-18, * is a bonding location, wherein in Ar$^1$ represented by Formula 2, when R$^1$ to R$^4$ are each a hydrogen atom, l is 1, and wherein the monoamine compound represented by Formula 1 is a single amine group compound.

2. The monoamine compound as claimed in claim 1, wherein the compound represented Formula 1 is represented by the following Formula 1-1, 1-2 or 1-6:

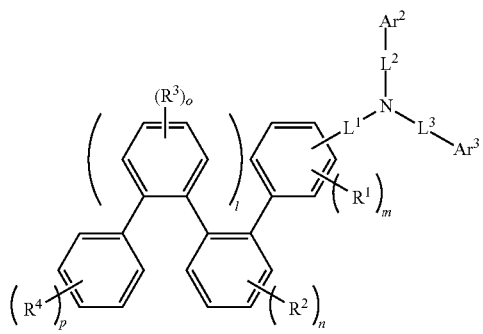

[Formula 1-1]

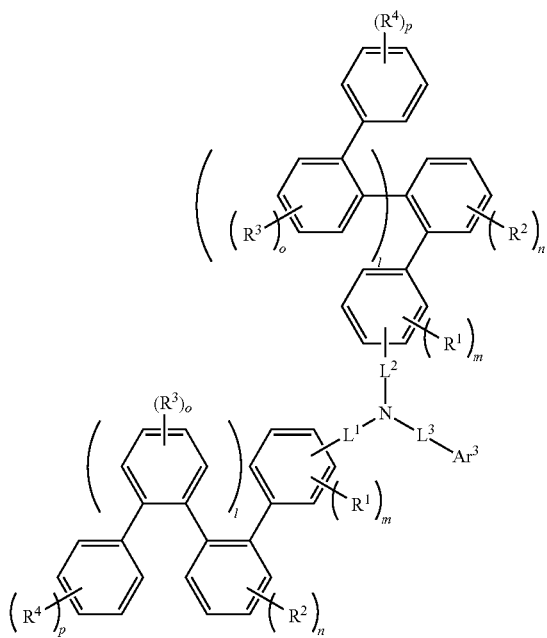

[Formula 1-2]

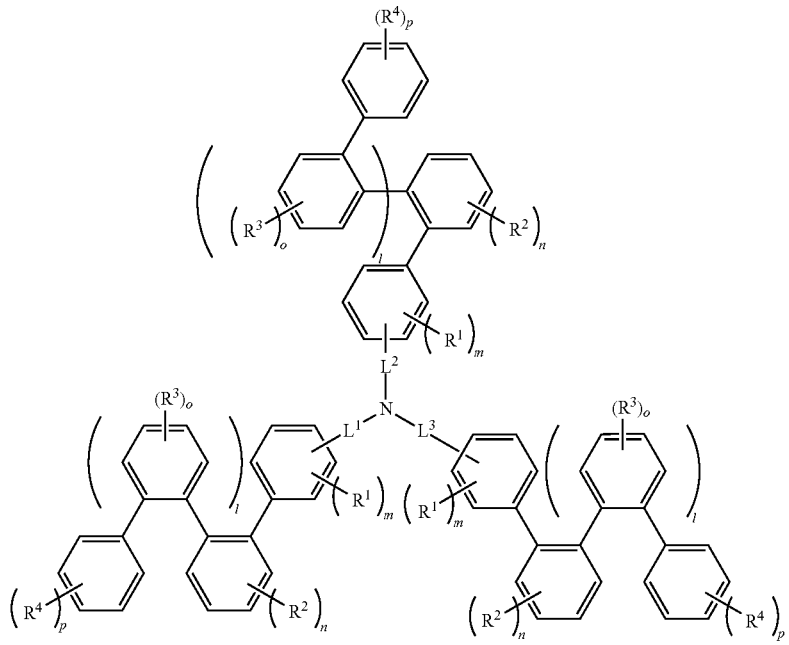

[Formula 1-6]

wherein, in Formulae 1-1, 1-2 and 1-6, Ar², Ar³, L¹ to L³, R¹ to R⁴, and l to p are defined the same as those of Formula 1.

3. The monoamine compound as claimed in claim 1, wherein the compound represented Formula 1 is represented by one of the following Formulae 1-3 to 1-5:

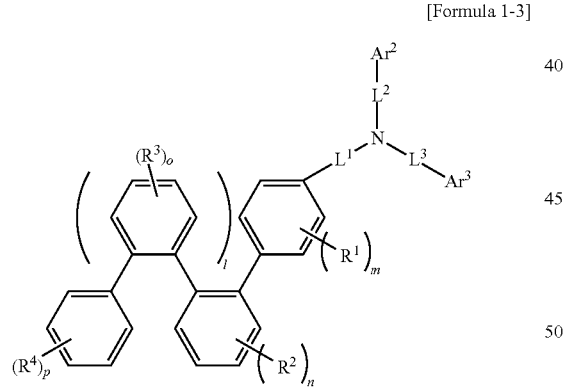

[Formula 1-3]

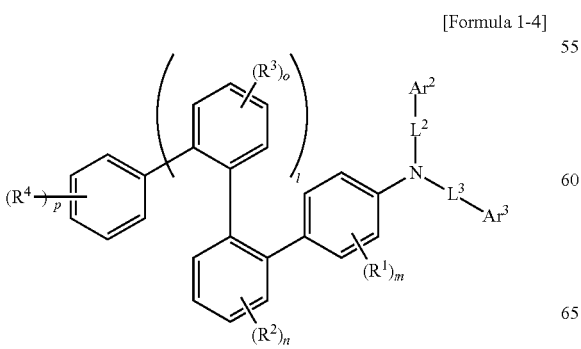

[Formula 1-4]

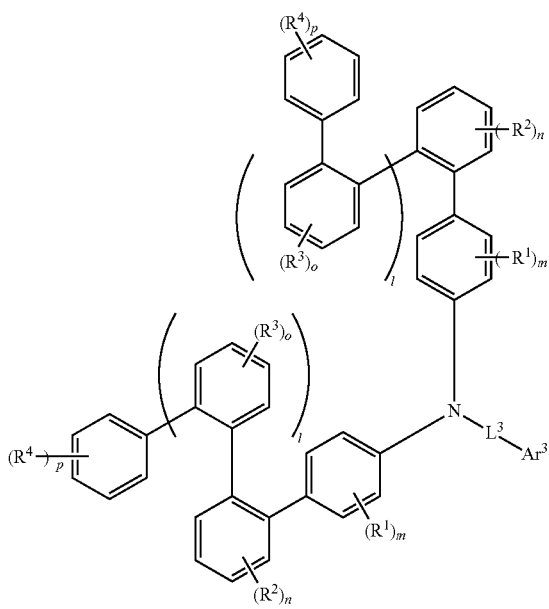

[Formula 1-5]

wherein, in Formulae 1-3 to 1-5, Ar², Ar³, L¹ to L³, R¹ to R⁴, and l to p are defined the same as those of Formula 1.

4. The monoamine compound as claimed in claim 1, wherein the group represented by Formula 2 is a group represented by one of the following Ar-1 to Ar-7 and Ar-9 to Ar-10, in which * is a bonding location:

Ar-1 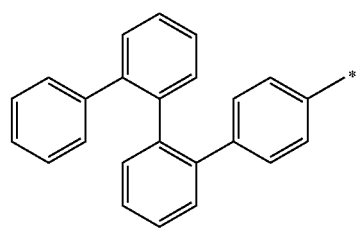

Ar-2 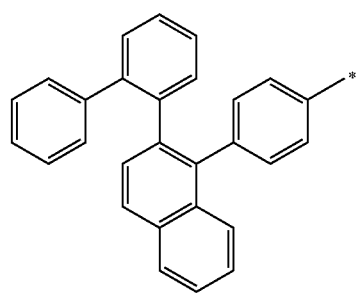

Ar-3 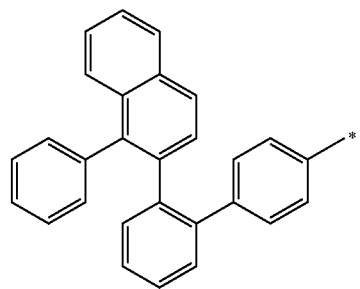

Ar-4 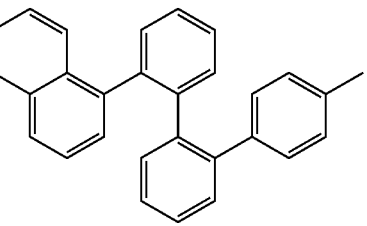

Ar-5 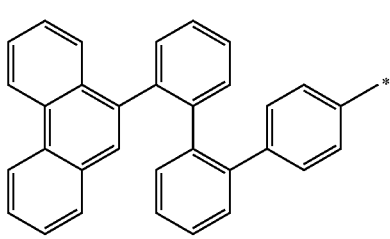

Ar-6 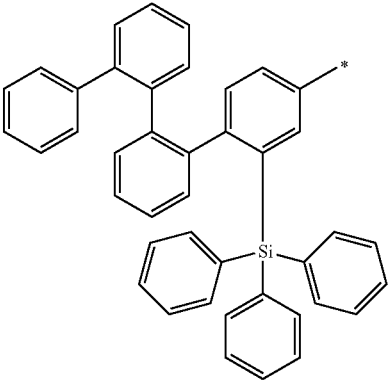

Ar-7 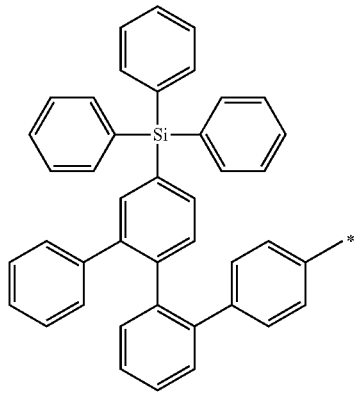

Ar-9 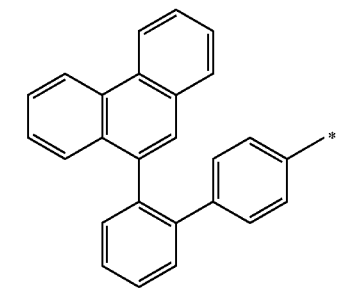

Ar-10 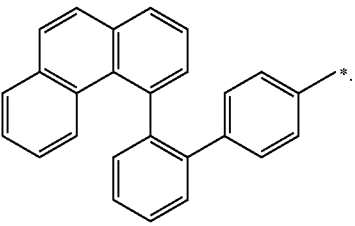

5. The monoamine compound as claimed in claim 1, wherein $Ar^2$ and $Ar^3$ are each independently a substituted or unsubstituted phenyl group, a substituted or unsubstituted biphenyl group, a substituted or unsubstituted terphenyl group, a substituted or unsubstituted naphthyl group, or a substituted or unsubstituted phenanthryl group.

6. The monoamine compound as claimed in claim 1, wherein $Ar^2$ and $Ar^3$ are each independently a group represented by one of the following Ar-11 to Ar-16, in which * is a bonding location:

Ar-11 

Ar-12 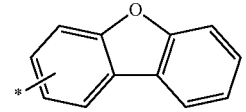

Ar-13 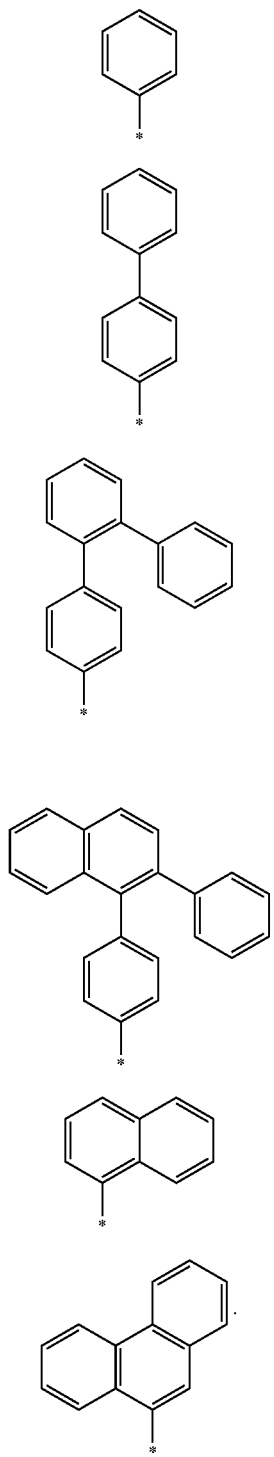

Ar-14

Ar-15

Ar-16

Ar-17 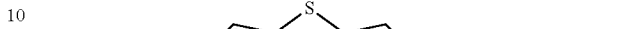

Ar-18 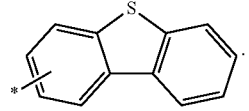

9. The monoamine compound as claimed in claim 1, wherein Ar$^2$ and Ar$^3$ are each independently a substituted or unsubstituted triphenylsilyl group.

10. The monoamine compound as claimed in claim 1, wherein L$^1$ to L$^3$ are each independently a direct linkage or a substituted or unsubstituted phenylene group.

11. A compound of the following Compound Group 1:

[Compound 1]

1
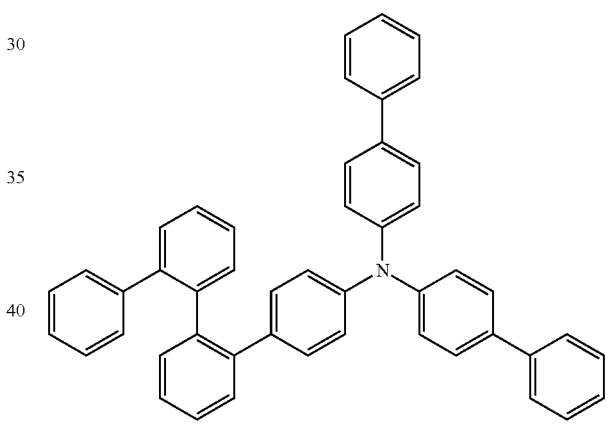

2
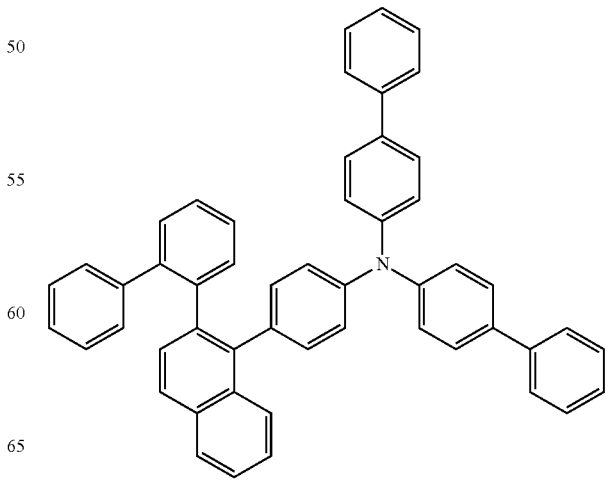

7. The monoamine compound as claimed in claim 1, wherein Ar$^2$ and Ar$^3$ are each independently a substituted or unsubstituted heteroaryl group that includes O or S as a heteroatom.

8. The monoamine compound as claimed in claim 1, wherein Ar$^2$ and Ar$^3$ are each independently a group represented by the following Ar-17 or Ar-18, which * is a bonding location:

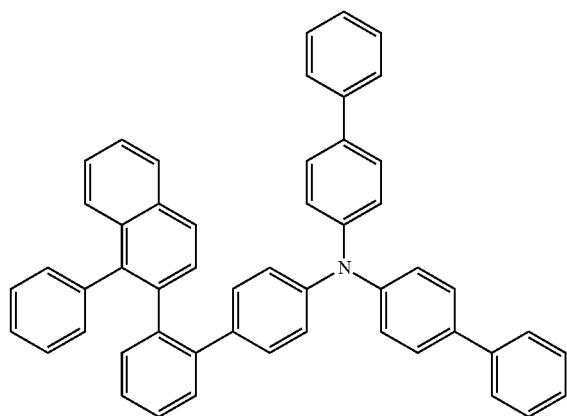
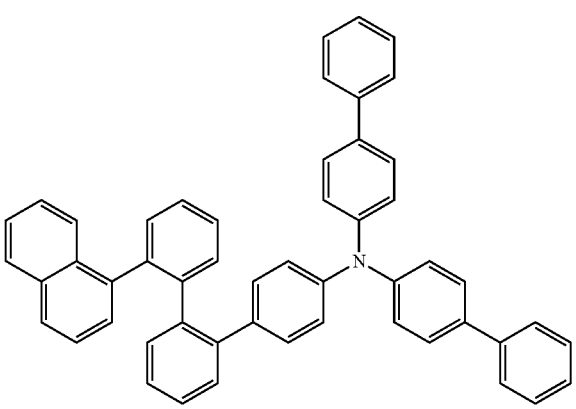
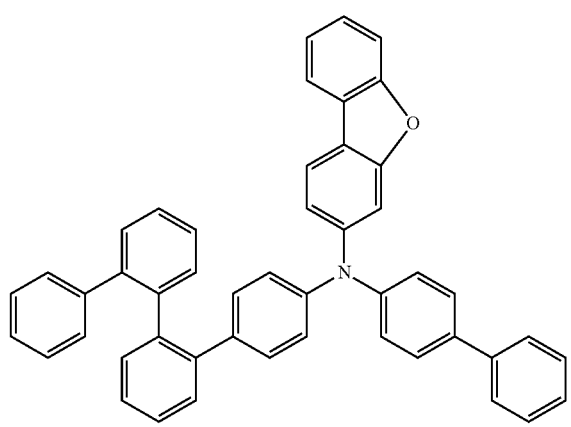
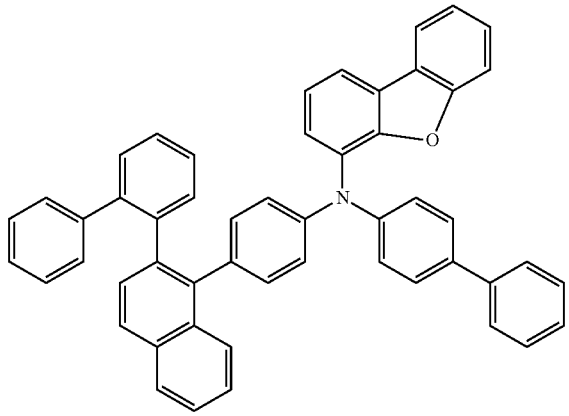
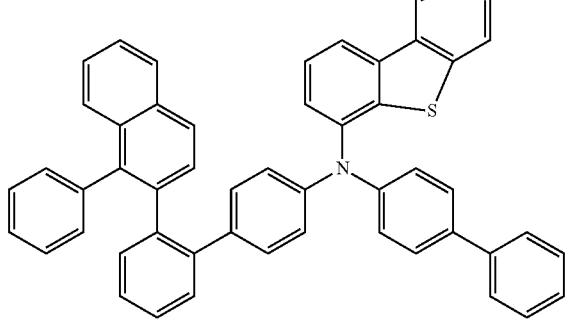
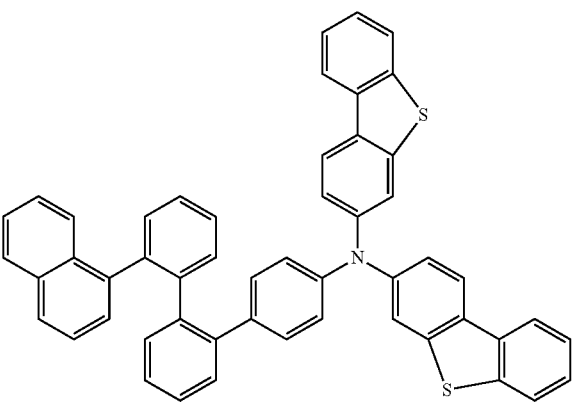
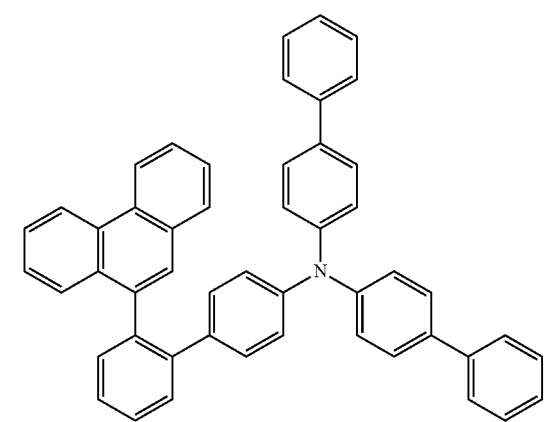

85
-continued
10
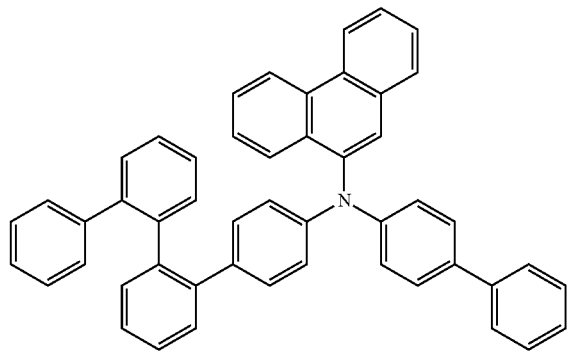
11
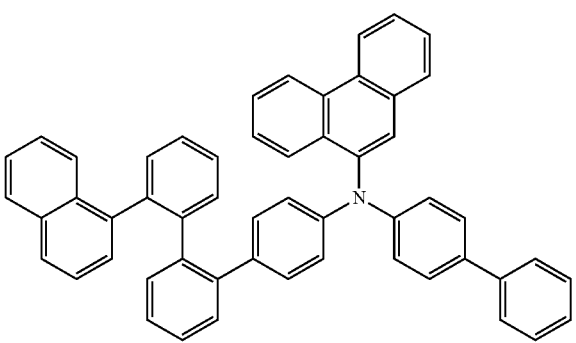
12
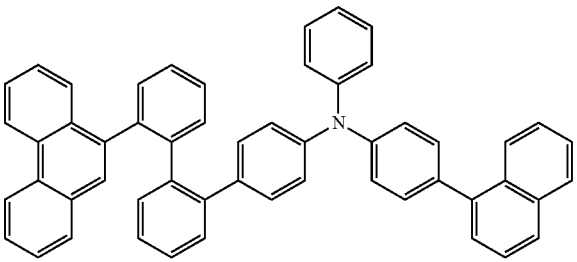
13
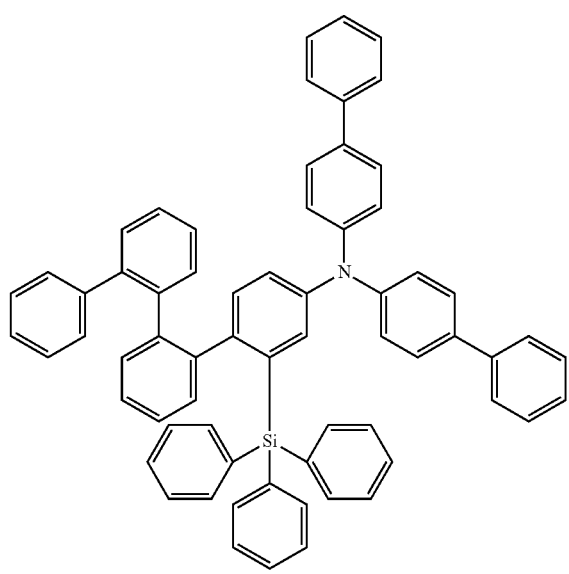
86
-continued
14
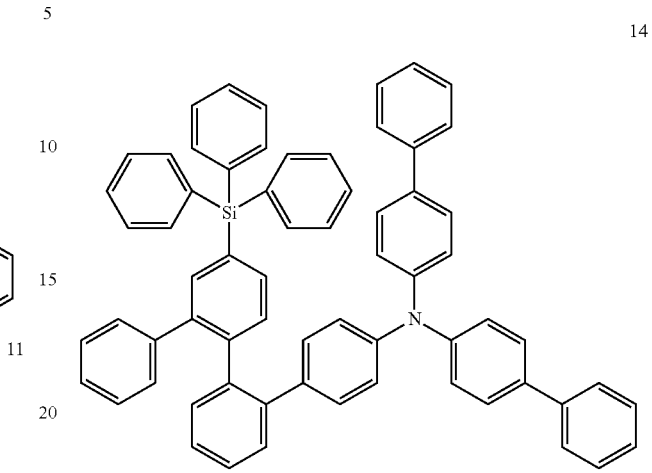
15
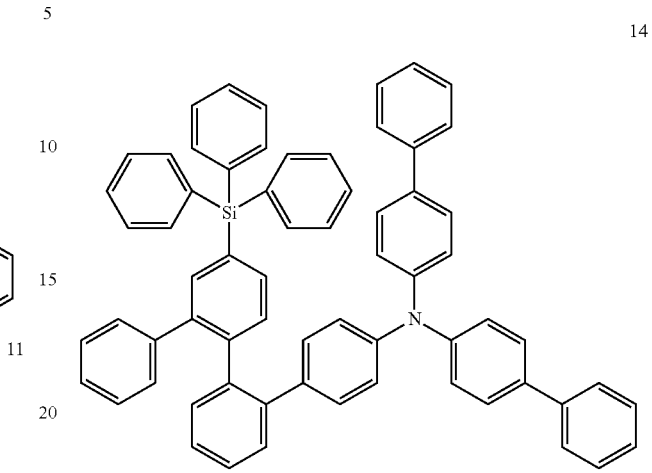
16
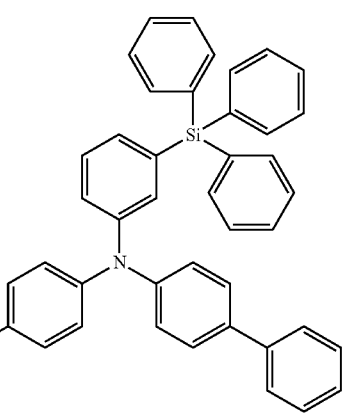

87
-continued
17
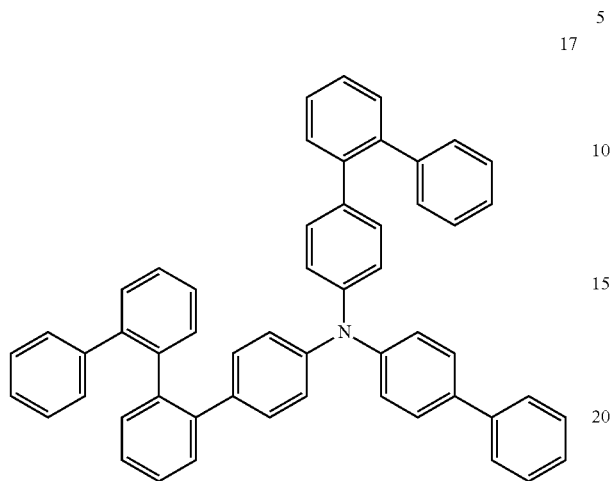
18
20
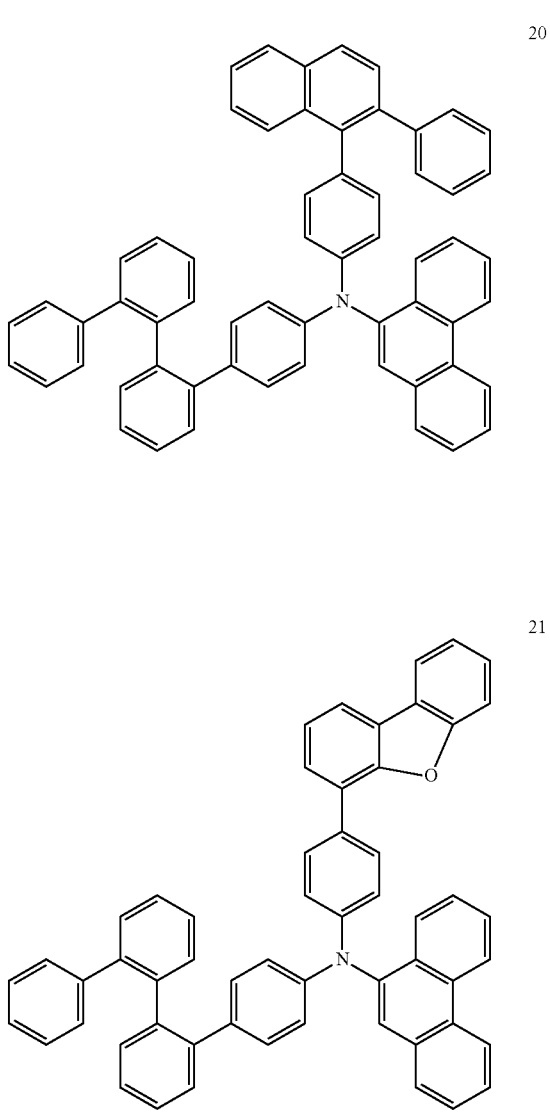
21
19
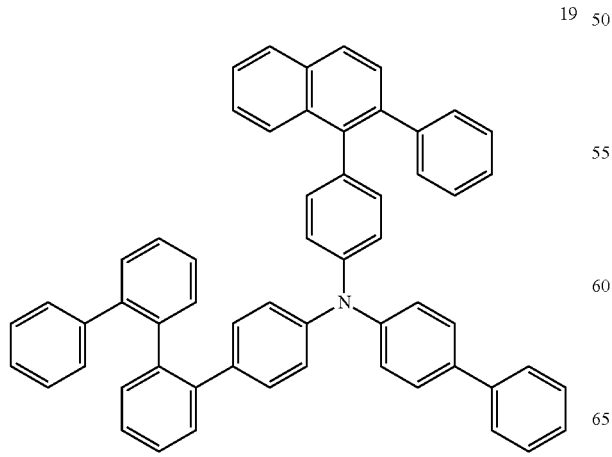
88
-continued
22
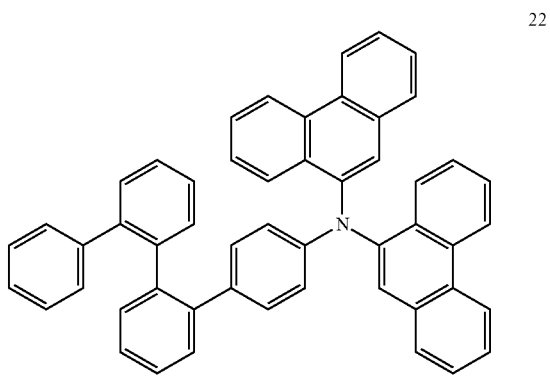

-continued

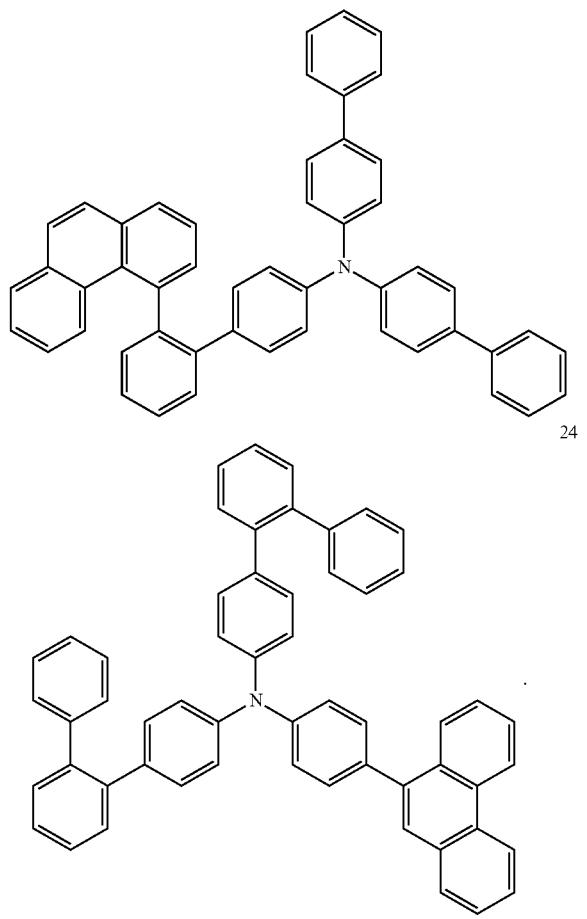

12. An organic electroluminescence device, comprising:
a first electrode;
an organic layer on the first electrode, the organic layer including a hole transport region, an emission layer, and an electron transport region; and
a second electrode on the organic layer,
wherein the organic layer includes a monoamine compound represented by the following Formula 1:

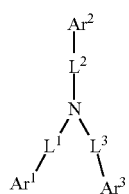

[Formula 1]

wherein, in Formula 1,
Ar$^1$ is a group represented by the following Formula 2,
Ar$^2$ and Ar$^3$ are each independently a group represented by the following Formula 2, a hydrogen atom, a deuterium atom, a halogen atom, a cyano group, a substituted or unsubstituted silyl group, a substituted or unsubstituted aryl group having 6 to 30 ring carbon atoms, or a substituted or unsubstituted heteroaryl group having 2 to 30 ring carbon atoms,
L$^1$ to L$^3$ are each independently a direct linkage, a substituted or unsubstituted arylene group having 6 to 30 ring carbon atoms, or a substituted or unsubstituted heteroarylene group having 2 to 30 ring carbon atoms,

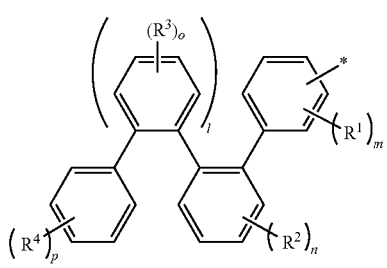

[Formula 2]

wherein, in Formula 2,
R$^1$ to R$^4$ are each independently a hydrogen atom, a deuterium atom, a halogen atom, a cyano group, a substituted or unsubstituted silyl group, a substituted or unsubstituted alkyl group having 1 to 10 carbon atoms, a substituted or unsubstituted alkoxy group having 1 to 10 carbon atoms, a substituted or unsubstituted arylthio group having 1 to 10 carbon atoms, or a substituted or unsubstituted aryl group having 6 to 30 ring carbon atoms,
R$^1$ to R$^4$ are separate or form a ring by combining adjacent groups with each other,
l is 0 or 1,
m, n, and o are each independently an integer of 0 to 4, and
p is an integer of 0 to 5,
wherein at least one selected from Ar$^1$, Ar$^2$ and Ar$^3$ is different from at least an other one selected from Ar$^1$, Ar$^2$ and Ar$^3$, and
wherein when L$^1$ to L$^3$ are each independently a direct linkage, and one selected from Ar$^2$ and Ar$^3$ is a group represented by Ar-18, an other one selected from Ar$^2$ and Ar$^3$ is a deuterium atom, a halogen atom, a cyano group, a substituted or unsubstituted silyl group, a substituted or unsubstituted aryl group derived from an aromatic hydrocarbon ring having 6 to 30 ring carbon atoms, or the group represented by Ar-18,

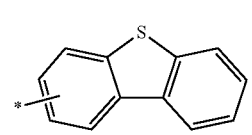

Ar-18 wherein in Ar-18, * is a bonding location,
wherein in Ar$^1$ represented by Formula 2, when R$^1$ to R$^4$ are each a hydrogen atom, l is 1, and
wherein the monoamine compound represented by Formula 1 is a single amine group compound.
13. The organic electroluminescence device as claimed in claim 12, wherein the hole transport region includes the monoamine compound represented by Formula 1.
14. The organic electroluminescence device as claimed in claim 12, wherein the emission layer emits blue light.
15. The organic electroluminescence device as claimed in claim 12, wherein the compound represented Formula 1 is represented by the following Formula 1-1, 1-2 or 1-6:

[Formula 1-1]
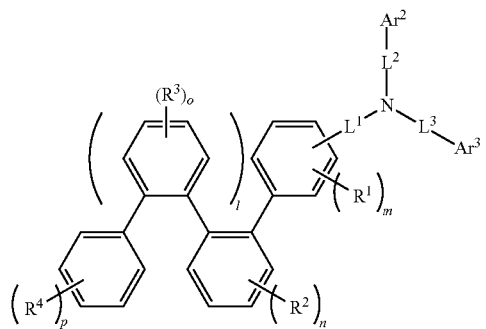
[Formula 1-2]
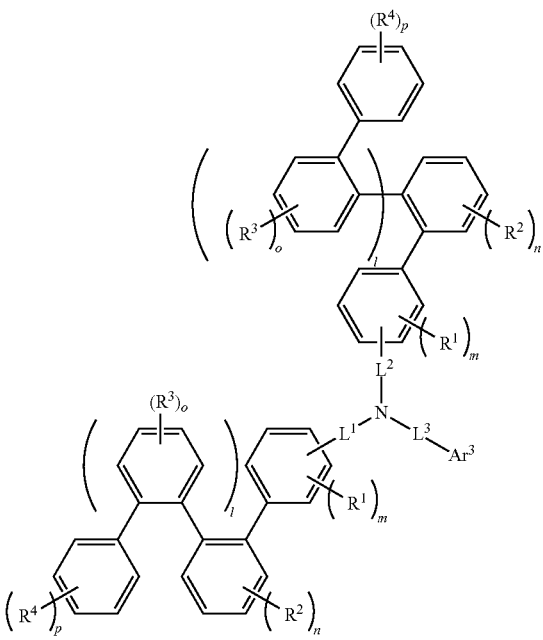
[Formula 1-6]
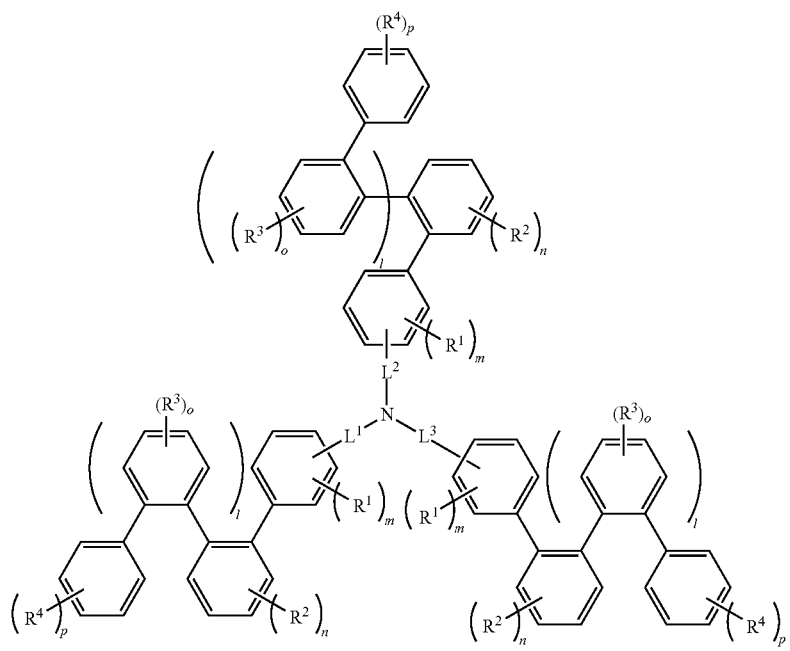
wherein, in Formulae 1-1, 1-2 and 1-6, $Ar^2$, $Ar^3$, $L^1$ to $L^3$, $R^1$ to $R^4$, and l to p are defined the same as those of Formula 1.

16. The organic electroluminescence device as claimed in claim 12, wherein the compound represented Formula 1 is represented by one of the following Formulae 1-3 to 1-5:

[Formula 1-3]

[Formula 1-4]

[Formula 1-5]

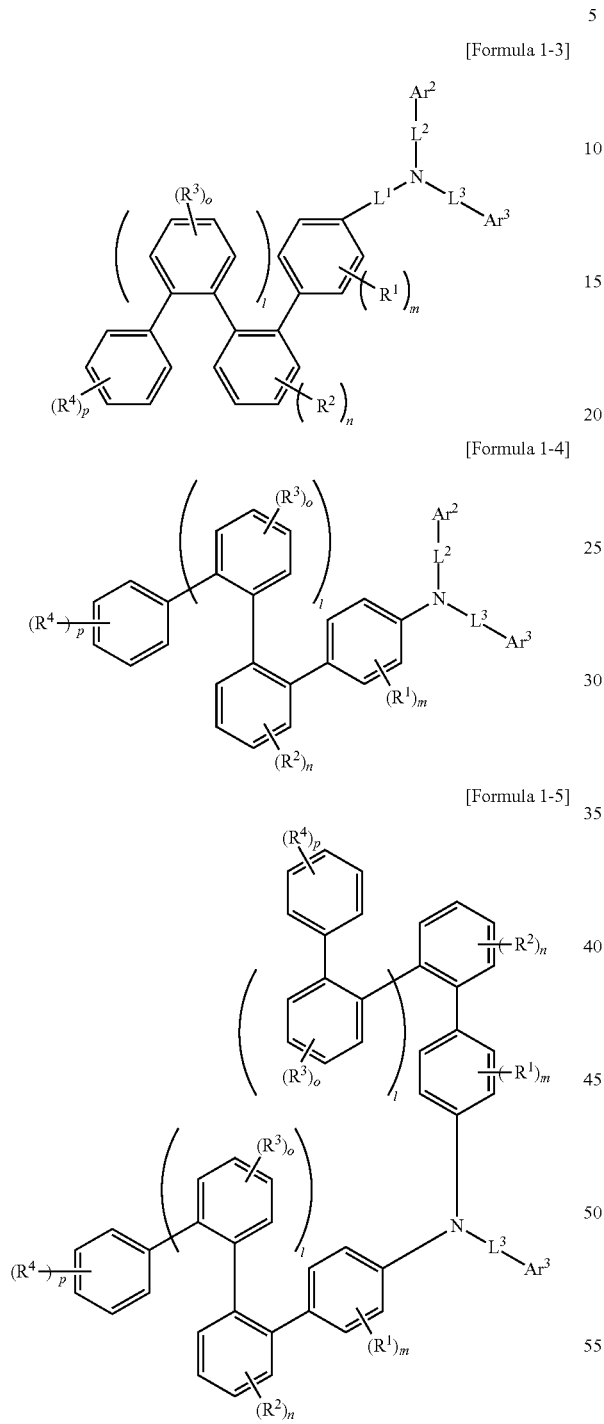

wherein, in Formulae 1-3 to 1-5, $Ar^2$, $Ar^3$, $L^1$ to $L^3$, $R^1$ to $R^4$, and l to p are defined the same as those of Formula 1.

17. The organic electroluminescence device as claimed in claim 12, wherein the group represented by Formula 2 is a group represented by one of the following Ar-1 to Ar-7 and Ar-9 to Ar-10, in which * is a bonding location:

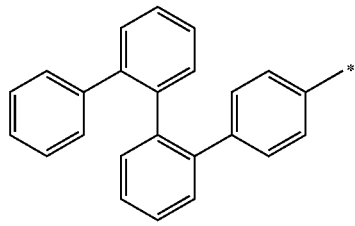
Ar-1

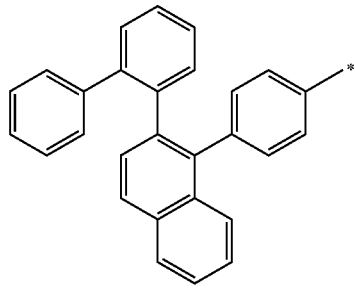
Ar-2

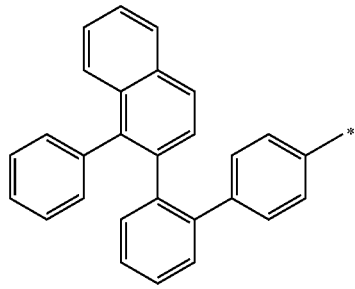
Ar-3

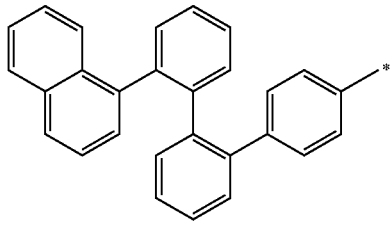
Ar-4

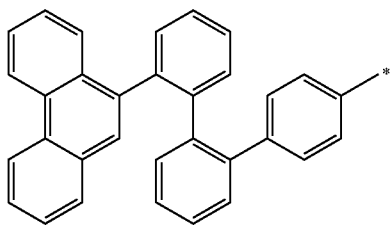
Ar-5

-continued

Ar-6
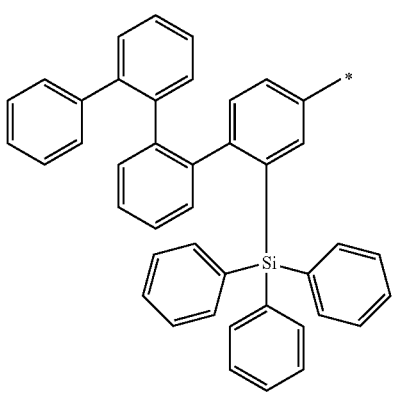

Ar-7
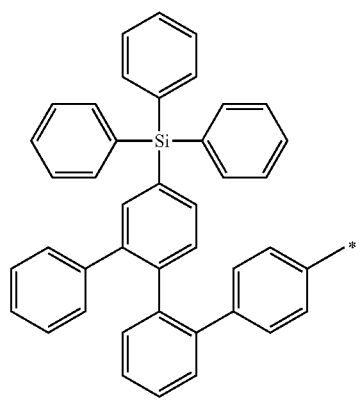

Ar-9
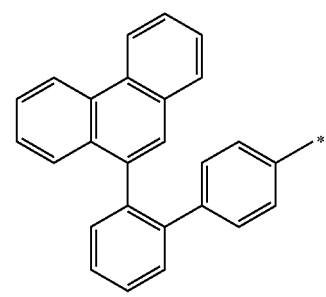

Ar-10
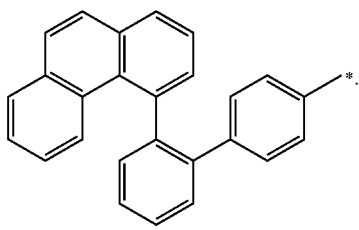

18. The organic electroluminescence device as claimed in claim 12, wherein $Ar^2$ and $Ar^3$ are each independently a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, or a substituted or unsubstituted heteroaryl group that includes O or S as a heteroatom.

19. The organic electroluminescence device as claimed in claim 12, wherein $L^1$ to $L^3$ are each independently a direct linkage or a substituted or unsubstituted phenylene group.

20. An organic electroluminescence device, comprising:
a first electrode;
an organic layer on the first electrode, the organic layer including a hole transport region, an emission layer, and an electron transport region; and
a second electrode on the organic layer,
wherein the organic layer includes a monoamine compound,
the hole transport region includes the monoamine compound, and
the monoamine compound is a compound of the following Compound Group 1:

[Compound 1]

1
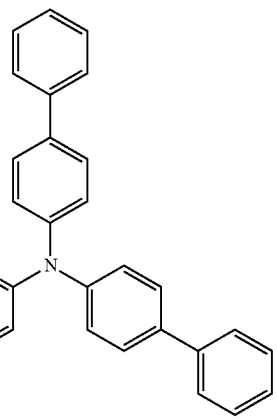

2
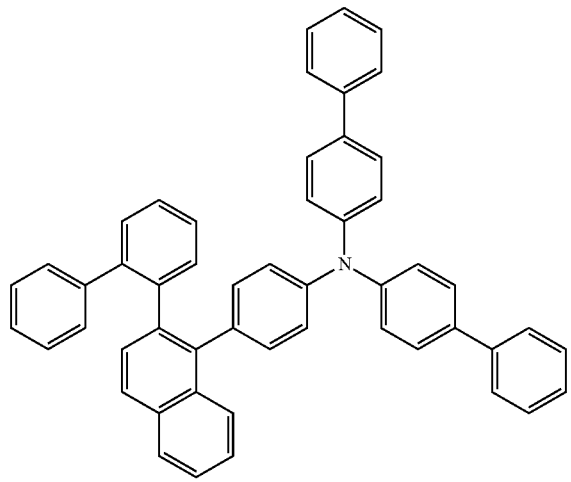

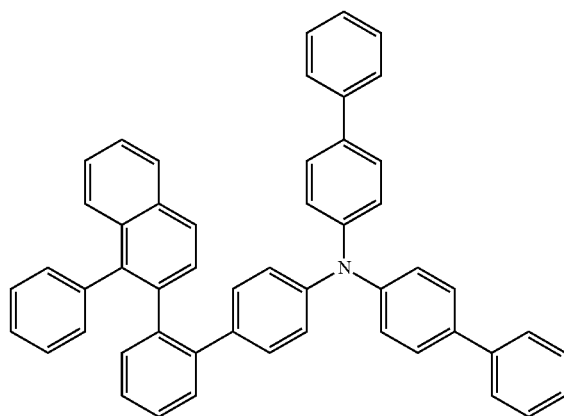
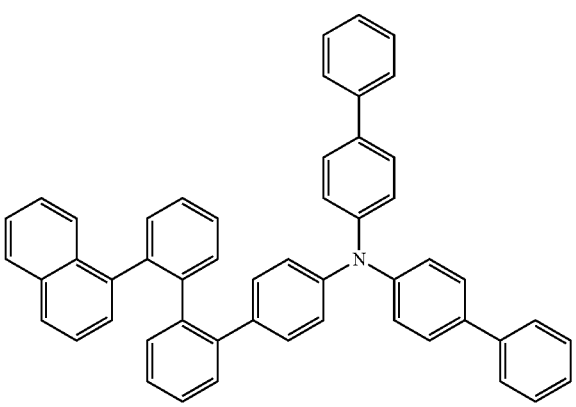
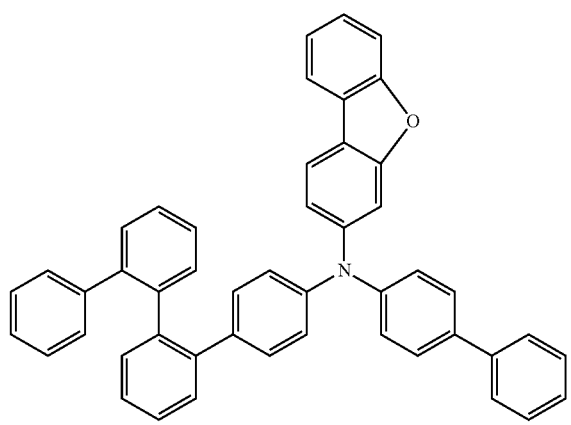
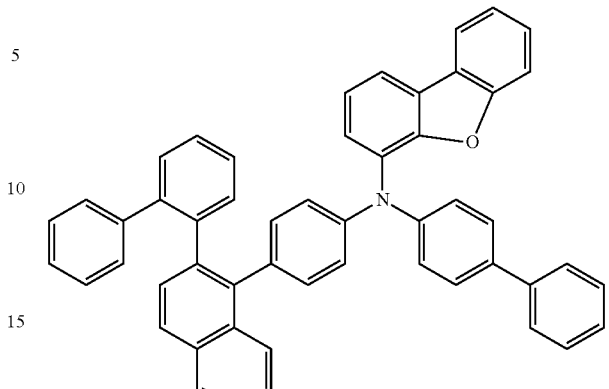
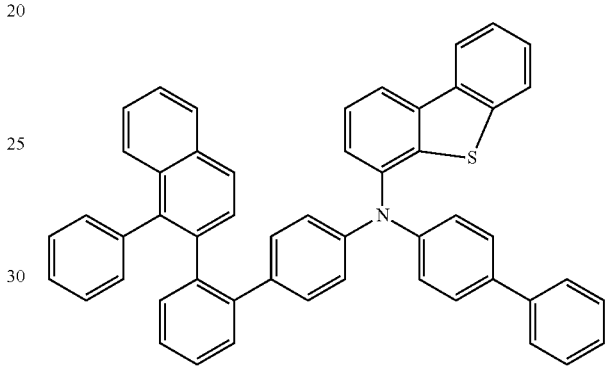
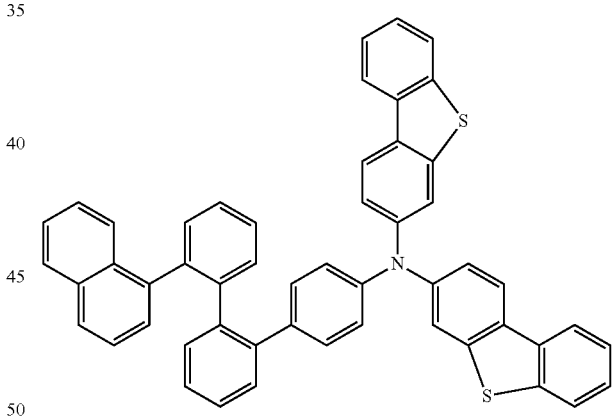
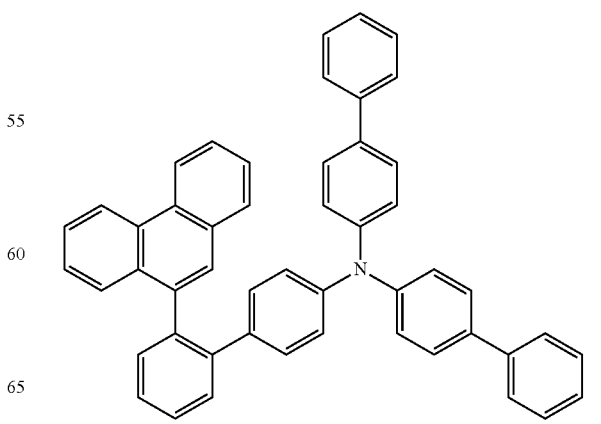

10
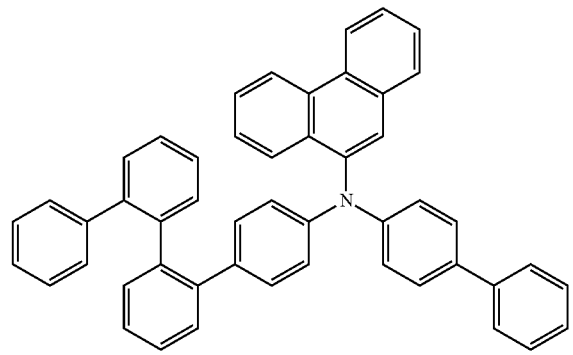
11
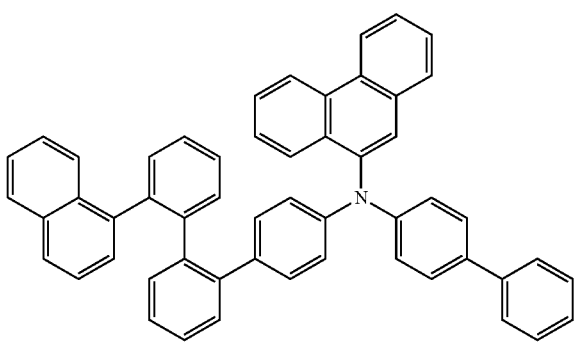
12
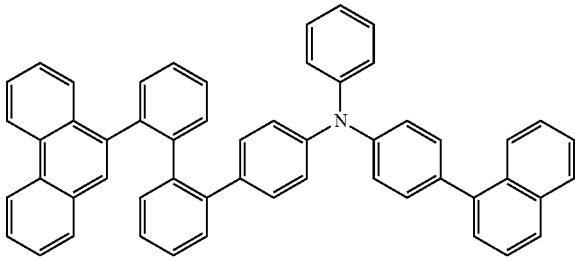
13
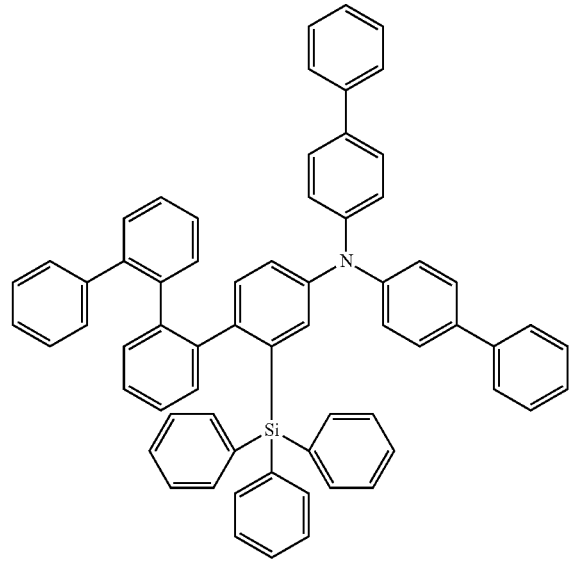
14
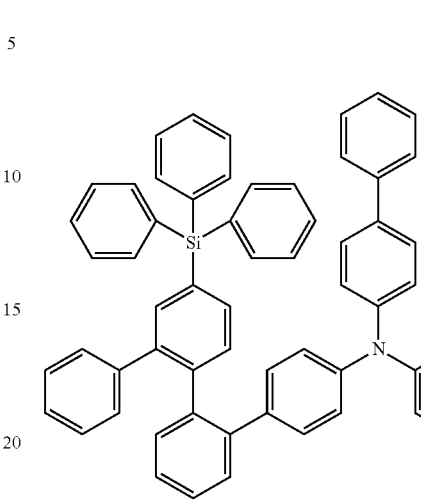
15
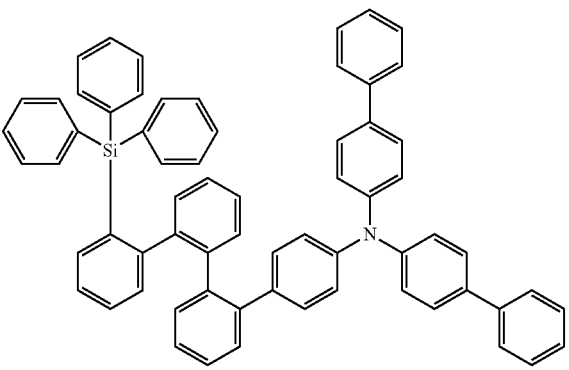
16
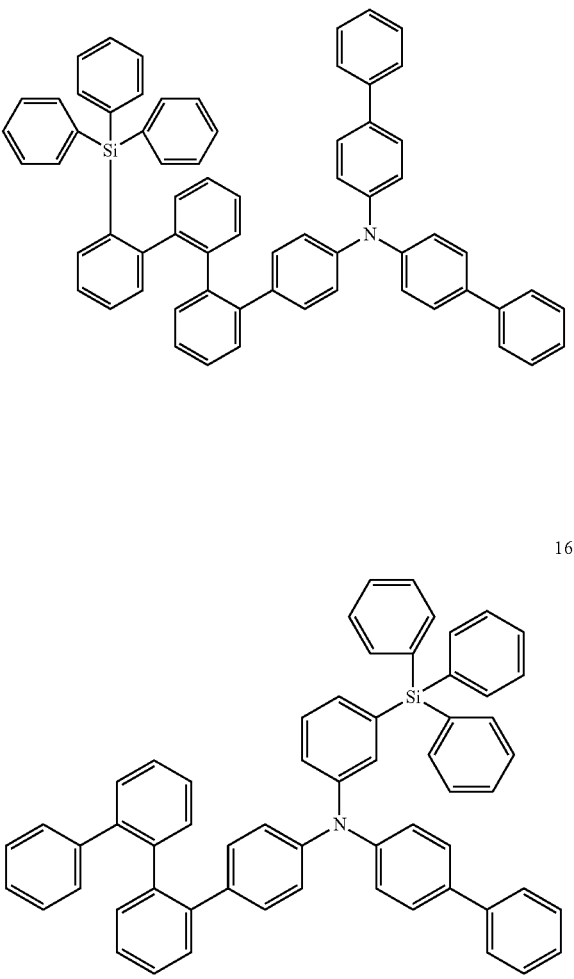

101
-continued
102
-continued
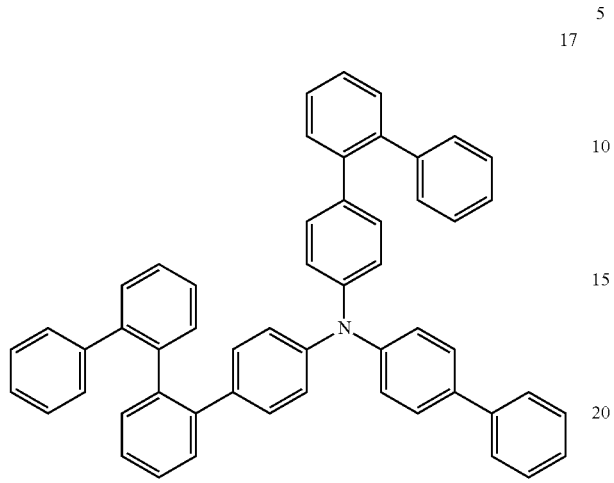
17
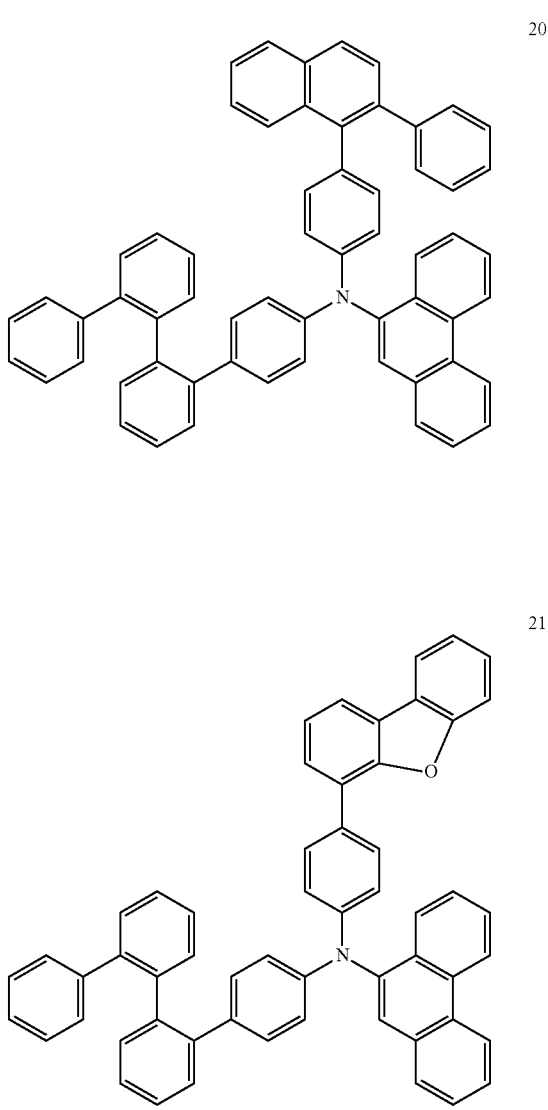
20
18
21
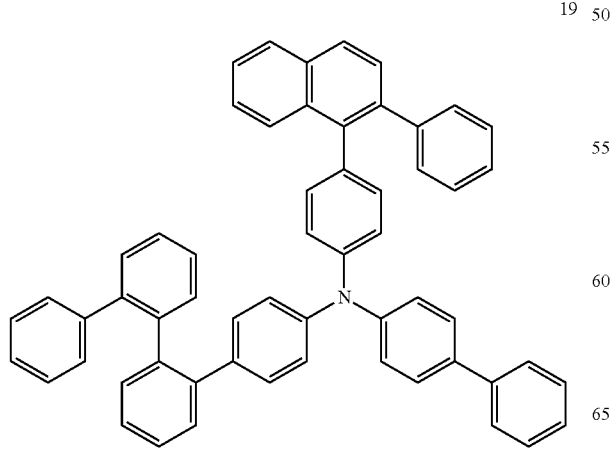
19
22

103
-continued
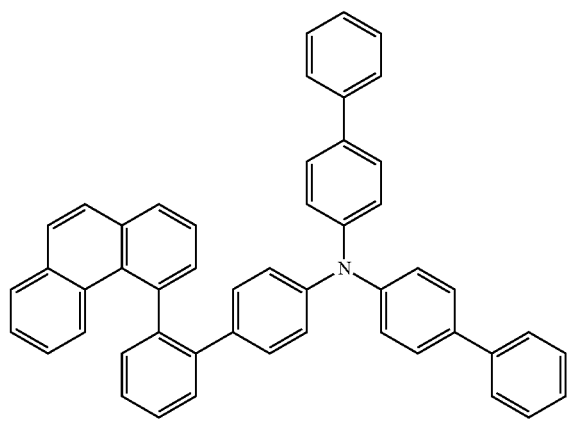
104
-continued
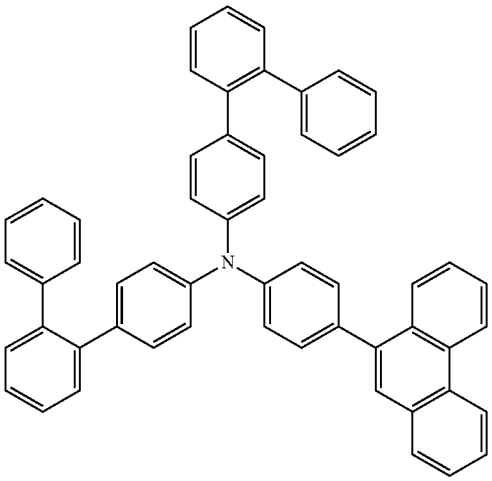
* * * * *